United States Patent
Kordes et al.

(10) Patent No.: US 8,211,924 B2
(45) Date of Patent: Jul. 3, 2012

(54) 1-(AZOLIN-2-YL)AMINO-1,2-DIPHENYLETHANE COMPOUNDS FOR COMBATING ANIMAL PESTS

(75) Inventors: Markus Kordes, Bobenheim-Roxheim (DE); Christopher Koradin, Ludwigshafen (DE); Ronan Le Vezouet, Mannheim (DE); Ernst Baumann, Dudenhofen (DE); Deborah L. Culbertson, Fuquay Varina, NC (US); Douglas D. Anspaugh, Apex, NC (US); Hassan Oloumi-Sadeghi, Raleigh, NC (US); Cecille Ebuenga, Laguna (PH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/667,299

(22) PCT Filed: Jul. 2, 2008

(86) PCT No.: PCT/EP2008/058517
§ 371 (c)(1), (2), (4) Date: Apr. 30, 2010

(87) PCT Pub. No.: WO2009/004032
PCT Pub. Date: Jan. 8, 2009

(65) Prior Publication Data
US 2010/0280078 A1 Nov. 4, 2010

Related U.S. Application Data

(60) Provisional application No. 60/958,134, filed on Jul. 3, 2007.

(51) Int. Cl.
A01N 43/78 (2006.01)
A01N 43/76 (2006.01)
A61K 31/425 (2006.01)
A61K 31/42 (2006.01)
C07D 277/00 (2006.01)
C07D 263/00 (2006.01)

(52) U.S. Cl. ........ 514/370; 514/377; 548/194; 548/200; 548/233

(58) Field of Classification Search .............. 514/370, 514/377; 548/194, 200, 233
See application file for complete search history.

(56) References Cited

U.S. PATENT DOCUMENTS

| 7,268,095 | B2 | 9/2007 | Preishuber-Pflügl et al. |
| 7,652,023 | B2 | 1/2010 | Wang et al. |
| 7,655,600 | B2 * | 2/2010 | Kordes et al. ............... 504/266 |
| 7,871,960 | B2 | 1/2011 | Kordes et al. |

FOREIGN PATENT DOCUMENTS

| WO | WO 2005/063724 | * | 6/2005 |
| WO | WO 2005/063724 | | 7/2005 |
| WO | WO 2006/125748 | | 11/2006 |
| WO | WO 2006/127426 | | 11/2006 |
| WO | WO 2007/071585 | | 6/2007 |
| WO | WO 2008/000834 | | 1/2008 |
| WO | WO 2008/104503 | * | 9/2008 |

OTHER PUBLICATIONS

International Search Report for International Application No. PCT/EP2008/058517.
International Preliminary Report on Patentability for International Application No. PCT/EP2008/058517.
Hirashima et al., "Synthesis and octopaminergic agonist activity of 2-(Substituted benzylamino)-2-thiazolines", Biosci. Biotech, Biochem., 56(7); 1062-1065 (1992).
Jennings et al., "A biorationally synthesized octopaminergic insecticide: 2-(4-Chloro-o-toluidino)-2-oxazoline", Pesticide Biochemistry and Physiology 30, 190-197 (1988).

* cited by examiner

*Primary Examiner* — Noble Jarrell
*Assistant Examiner* — Valerie Rodriguez-Garcia
(74) *Attorney, Agent, or Firm* — Brinks Hofer Gilson & Lione

(57) ABSTRACT

The present invention relates to 1-(azolin-2-yl)amino-1,2-diphenylethane compounds of the formula I and to their salts which are useful for combating animal pests. The invention also relates to a method for controlling animal pests by using these compounds, to seed and to an agricultural and veterinary composition comprising said compounds.

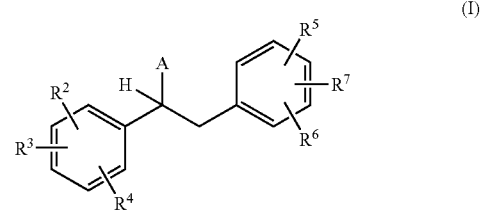

wherein A is a radical of formulae A.1 or A.2

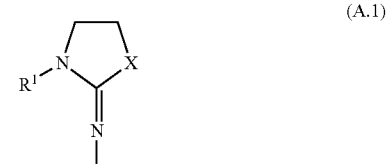

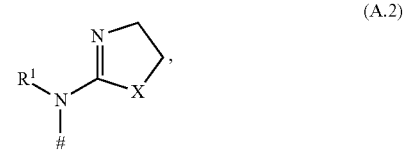

wherein # denotes the bond to the remaining compound of formula I, X is selected from O, S and $NR^X$,
$R^1$ is selected from the group consisting of $-OR^A$, $-NR^{B1}R^{B2}$, —C(=O)—R$^C$, —C(=O)—OR$^D$, —C(=O)—SR$^E$, —C(=O)—NR$^{B1}$R$^{B2\prime}$, —C(=S)—R$^{C\prime}$, —C(=S)—OR$^{D\prime}$, —C(=S)—SR$^{E\prime}$, —C(=S)—NR$^{B1}$R$^{B2}$, —C(=NR$^{1a}$)—R$^{C\prime}$, —C(=NR$^{1b}$)—OR$^{D\prime}$, —C(=NR$^{1c}$)—SR$^{E\prime}$, —C(=NR$^{1d}$)—NR$^{B1}$R$^{B2}$, —S(=O)—R$^F$, —S(=O)$_2$—R$^G$, —S(=O)$_2$—NR$^{B1}$R$^{B2\prime}$, —P(=O)R$^{H1}$R$^{H2}$, —P(=S)R$^{H1}$R$^{H2}$, —B—C(=O)—R$^I$, —B—O—C(=O)—R$^I$, —B—S—C(=O)—R$^I$, —B—N(R$^J$)—C(=O)—R$^K$, —B—C(=S)—R$^K$, —B—O—C(=S)—R$^K$, —B—S—C(=S)—R$^K$, —B—N(R$^J$)—C(=S)—R$^K$, C$_1$-C$_8$-alkenyl, C$_1$-C$_8$-alkynyl, C$_3$-C$_8$-cycloalkyl, which is unsubstituted or may carry 1 to 4 substituents R$^{1e}$, naphthyl, which is unsubstituted or may carry 1 to 4 substituents R$^{1f}$, a saturated or partially unsaturated heterocycle, which is unsubstituted or may carry 1 to 4 substituents R$^{1g}$, hetaryl, which is unsubstituted or may carry 1 to 4 substituents R$^{1h}$, and C$_1$-C$_6$-alkyl, which carries a radical selected from the group consisting of —NR$^{1i}$R$^{1j}$, C$_1$-C$_4$-alkoxycarbonyl, C$_3$-C$_8$-cycloalkyl, aryl, aryloxy, arylthio, heterocyclyl, heterocyclyloxy and heterocyclylthio, R$^2$, R$^3$, R$^4$, R$^5$, R$^6$ and R$^7$ are each independently hydrogen, halogen, OH, SH, NH$_2$, SO$_3$H, COOH, cyano, nitro, C$_1$-C$_6$-alkyl, C$_1$-C$_6$-alkoxy, C$_1$-C$_6$-alkylamino etc.

24 Claims, No Drawings

1-(AZOLIN-2-YL)AMINO-1,2-DIPHENYLETHANE COMPOUNDS FOR COMBATING ANIMAL PESTS

This application is a National Stage application of International Application No. PCT/EP2008/058517 filed Jul. 2, 2008, which claims the benefit of U.S. Provisional Application No. 60/958,134, filed Jul. 3, 2007, the entire contents of which is hereby incorporated herein by reference.

The present invention relates to 1-(azolin-2-yl)amino-1,2-diphenylethane compounds which are useful for combating animal pests. The invention also relates to a method for controlling animal pests by using these compounds, to seed and to an agricultural and veterinary composition comprising said compounds.

Animal pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating insects, arachnids and nematodes. It is therefore an object of the present invention to provide compounds having a good pesticidal activity and showing a broad activity spectrum against a large number of different animal pests, especially against difficult to control insects, arachnids and nematodes.

Jennings et al. Pesticide Biochemistry and Physiology 30, 1988, p. 190-197 describe several 2-phenylamino oxazolines and 2-benzylamino oxazolines which have insecticidal activity. Biosci. Biotech. Biochem. 1992, 56 (7), 1062-1065 discloses phenyl-, benzyl- and phenethyl thiazolines having insecticidal activity. However, these compounds are limited in their activity or with regard to breadth of their activity spectrum.

The WO 2005/063724 describes 1-(azolin-2-yl)amino-1,2-diphenylethane compounds of the general formulae C.1 and C.2,

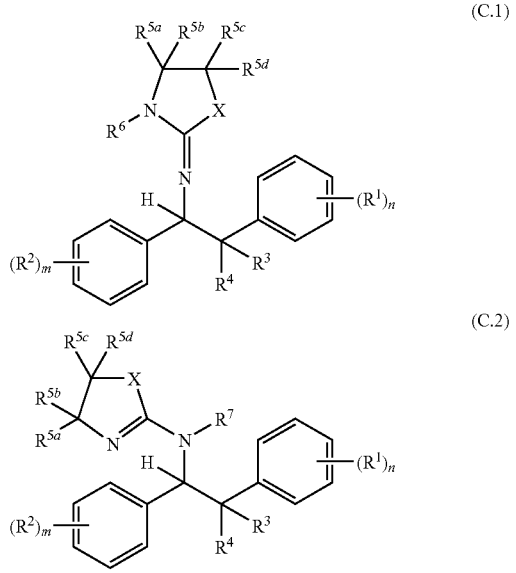

wherein X is sulfur or oxygen, which are useful for combating insects, arachnids and nematodes.

It is an object of the present invention to provide compounds that have a good pesticidal activity, in particular insecticidal activity, and show a broad activity spectrum against a large number of different animal pests, especially against difficult to control insects.

It has been found that these objectives can be achieved by compounds of the formula I below.

Therefore, in a first aspect, the invention relates to compounds of formula I

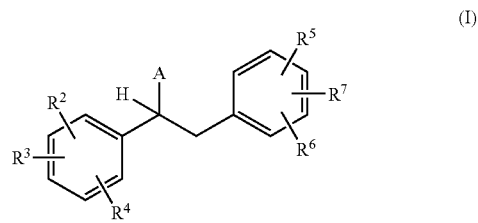

wherein
A is a radical of formulae A.1 or A.2

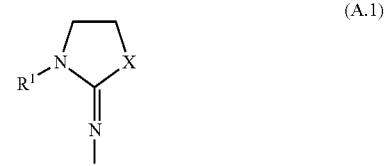

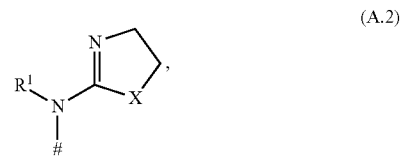

wherein # denotes the bond to the remaining compound of formula I

X is selected from O, S and $NR^X$, wherein
$R^X$ is selected from hydrogen, cyano, nitro, $C_1$-$C_3$-alkyl, $C_1$-$C_3$-alkoxy, $C_1$-$C_3$-haloalkyl, $C_1$-$C_3$-haloalkoxy, formyl, $C_1$-$C_6$-alkylcarbonyl and $C_1$-$C_6$-alkoxycarbonyl;

$R^1$ is selected from the group consisting of —$OR^A$, —$NR^{B1}R^{B2}$,
—C(=O)—$R^C$, —C(=O)—$OR^D$, —C(=O)—$SR^E$,
—C(=O)—$NR^{B1}R^{B2}$, —C(=S)—$R^{C\prime}$, —C(=S)—$OR^{D\prime}$, —C(=S)—$SR^{E\prime}$, —C(=S)—$NR^{B1}R^{B2}$,
—C(=$NR^{1a}$)—$R^{C\prime}$, —C(=$NR^{1b}$)—$OR^{D\prime}$,
—C(=$NR^{1c}$)—$SR^{E\prime}$, —C(=$NR^{1d}$)—$NR^{B1}R^{B2}$,
—S(=O)—$R^F$, —S(=O)$_2$—$R^G$, —S(=O)$_2$—$NR^{B1}R^{B2}$,
—P(=O)$R^{H1}R^{H2}$, —P(=S)$R^{H1}R^{H2}$, —B—C(=O)—$R^I$, —B—O—C(=O)—$R^I$, —B—S—C(=O)—$R^I$,
—B—N($R^J$)—C(=O)—$R^K$, —B—C(=S)—$R^K$,
—B—O—C(=S)—$R^K$, —B—S—C(=S)—$R^K$,
—B—N($R^J$)—C(=S)—$R^K$,
$C_1$-$C_8$-alkenyl, $C_1$-$C_8$-alkynyl, $C_3$-$C_8$-cycloalkyl, which is unsubstituted or may carry 1 to 4 substituents $R^{1e}$,
naphthyl, which is unsubstituted or may carry 1 to 4 substituents $R^{1f}$,
a saturated or partially unsaturated heterocycle, which is unsubstituted or may carry 1 to 4 substituents $R^{1g}$,
hetaryl, which is unsubstituted or may carry 1 to 4 substituents $R^{1h}$, and
$C_1$-$C_6$-alkyl, which carries a radical selected from the group consisting of —$NR^{1i}R^{1j}$, $C_1$-$C_4$-alkoxycarbonyl, $C_3$-$C_8$-cycloalkyl, aryl, aryloxy, arylthio, heterocyclyl, heterocyclyloxy and heterocyclylthio, wherein the alkyl, cycloalkyl, aryl or heterocyclyl moieties of the last 8 mentioned radicals may carry 1, 2, 3 or four radicals selected from CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_8$-cycloalkyl, wherein B is linear or branched $C_1$-$C_4$-alkylene, which is unsubstituted or may carry 1, 2, 3 or 4 radicals selected from halogen and $C_1$-$C_3$-alkoxy, $R^A$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^{B1}$, $R^{B2}$ are selected independently from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^{B2'}$ is selected from the group consisting of $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^C$ is selected from, $C_1$-$C_6$-alkyl which carries 1, 2, 3 or 4 radicals selected from C(=O)OH, aryloxy, hetaryloxy, arylthio, hetarylthio or $C_1$-$C_4$-alkoxy-carbonyl, wherein the five last mentioned radicals are unsubstituted or may carry 1, 2, 3 or 4 groups selected independently from CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_8$-cycloalkyl, $R^{C'}$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^D$, $R^E$ are selected from the group consisting of $C_2$-$C_6$-alkenyl, $C_2$-$C_6$-alkynyl, wherein the last two mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^{D'}$, $R^{E'}$, $R^{E1}$, $R^G$, $R^{H1}$, $R^{H2}$ have one of the meanings given for $R^D$, $R^E$ or are selected from hydrogen or $C_1$-$C_6$-alkyl, which is unsubstitued or carries 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $R^I$, $R^K$ are selected from the group consisting of $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^J$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$, $R^{1a}$, $R^{1b}$, $R^{1c}$ and $R^{1d}$ is selected from hydrogen $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy, $R^{1e}$, $R^{1g}$ are independently of one another selected from $C_1$-$C_3$-alkyl, $C_1$-$C_3$-alkoxy, $C_1$-$C_3$-haloalkyl and $C_1$-$C_3$-haloalkoxy, $R^{1f}$, $R^{1h}$ are independently of one another selected from CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_8$-cycloalkyl, $R^{1i}$ is selected from hydrogen, $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy, and $R^{1j}$ is selected from $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy, and $R^2$, $R^3$, $R^4$, $R^5$, $R^6$ and $R^7$ are each independently hydrogen, halogen, OH, SH, $NH_2$, $SO_3H$, COOH, cyano, nitro, $C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, formyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, $C_2$-$C_6$-alkenyloxycarbonyl, $C_2$-$C_6$-alkynyloxycarbonyl, carbonyloxy, $C_1$-$C_6$-alkylcarbonyloxy, $C_1$-$C_6$-alkenylcarbonyloxy, $C_1$-$C_6$-alkynylcarbonyloxy, wherein the carbon atoms in the aliphatic radicals of the aforementioned groups may carry any combination of 1, 2 or 3 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, C(O)$NR^LR^M$, (SC$_2$)$NR^LR^M$, wherein $R^L$ and $R^M$ are each independently hydrogen, $C_1$-$C_6$-alkyl, $C_2$-$C_6$-alkenyl, or $C_2$-$C_6$-alkynyl, wherein the carbon atoms in these groups may carry any combination of 1, 2 or 3 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, a radical Y—Ar or a radical Y-Cy, wherein Y is a single bond, oxygen, sulfur, $C_1$-$C_6$-alkanediyl or $C_1$-$C_6$-alkanediyloxy, Ar is phenyl, naphthyl or a mono- or bicyclic 5- to 10-membered heteroaromatic ring, which contains 1,2, 3 or 4 heteroatoms se-lected from oxygen, sulfur and nitrogen as ring members, wherein Ar is unsubstituted or may carry any combination of 1, 2, 3, 4 or 5 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; and Cy is $C_3$-$C_{12}$-cycloalkyl, which is unsubstituted or substituted with any combination of 1, 2, 3, 4 or 5 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

and wherein two radicals $R^2$, $R^3$, $R^4$, $R^5$ or $R^6$ that are bound to adjacent carbon atoms of the phenyl rings may form together with said carbon atoms a fused benzene ring, a fused saturated or partially un-saturated 5-, 6-, or 7-membered carbocycle or a fused 5-, 6-, or 7-membered heterocycle, which contains 1, 2, 3 or 4 heteroatoms selected from O, S and N as ring members, and wherein the fused ring is unsubstituted or may carry any combination of 1, 2, 3, or 4 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

or the enantiomers, diastereomers or salts thereof.

Another object of the present invention is the use of the compounds of formula I as defined above or of a salt thereof for combating animal pests.

Another object of the present invention is an agricultural composition containing at least one compound of the formula I as defined above and/or an agriculturally acceptable salt thereof and at least one liquid or solid carrier.

Another object of the present invention is a veterinary composition containing at least one compound of the formula I as defined above and/or a veterinarily acceptable salt thereof and at least one veterinarily acceptable liquid or solid carrier.

The present invention also provides a method for controlling animal pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from pest attack or infestation with a pesticidally effective amount of a com-pound of the formula I or a salt thereof or a composition as defined above.

The invention further related to a method for treating or protecting an animal from infestation or infection by parasites which comprises bringing the animal in contact with a parasiticidally effective amount of a compound of the formula I or a veterinarily acceptable salt thereof as defined above. Bringing the animal in contact with the compound I, its salt or the veterinary composition of the invention means applying or administering it to the animal.

A further object of the present invention is plant propagation material, in particular seed, comprising at least one compound of formula I and/or an agriculturally acceptable salt thereof.

In the compounds of formula I, the carbon atom which carries the radical A creates a center of chirality. Thus, the compound of formula I may be present in the form of different enantiomers or if another center of chirality is present in any of the radicals $R^2$ to $R^7$, it may exist in the form of diastereomers. In case that A is a radical of the formula A.2, the compound I may also exist as a cis- or trans-isomer with respect to the N=C axis. The present invention relates to every possible stereoisomer of the compounds of formula I, i.e. to single enantiomers or diastereomers, as well as to mixtures thereof.

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "plant propagation material" includes any parts of a plant which are propagable. In general, a plant propagation material is the product of the ripened ovule of gymnosperm and angiosperm plants which occurs after fertilization and some growth within the mother plant and includes seed, fruits, spurious fruits, infructescences and also rhizomes (rootstocks), corms, tubers, bulbs and scions. In particular, the term "plant propagation material" has to be understood as seed.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

Examples of other meanings are:

The term "$C_1$-$C_6$-alkyl" as used herein and in the alkyl moieties of $C_1$-$C_6$-alkoxy, $C_1$-$C_6$-alkylamino, di($C_1$-$C_6$-alkyl)amino, $C_1$-$C_6$-alkylthio, $C_1$-$C_6$-alkylsulfonyl, $C_1$-$C_6$-alkylsulfoxyl, $C_1$-$C_6$-alkylcarbonyl, $C_1$-$C_6$-alkoxycarbonyl, $C_1$-$C_6$-alkylthio and $C_1$-$C_6$-alkylcarbonyloxy refers to a saturated straight-chain or branched hydrocarbon group having 1 to 6 carbon atoms, especially 1 to 3 carbon groups (=$C_1$-$C_3$-alkyl). Examples for $C_1$-$C_3$-alkyl are methyl, ethyl, propyl and 1-methylethyl(isopropyl). Examples for $C_1$-$C_6$-alkyl further encompass, butyl, 1-methylpropyl(sec-butyl, 2-butyl), 2-methylpropyl(iso-butyl), 1,1-dimethylethyl(tert-butyl), pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methyl pentyl, 2-methylpentyl, 3 methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methyl propyl.

The term "$C_1$-$C_6$-haloalkyl" as used herein refers to a straight-chain or branched saturated alkyl group having 1 to 6 carbon atoms (as mentioned above), where some or all of the hydrogen atoms in these groups may be replaced by halogen atoms as men-tioned above, for example $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1 fluoroethyl, 2-fluoroethyl, 2,2-difluoroethyl, 2,2,2-trifluoroethyl, 2-chloro-2-fluoroethyl, 2 chloro-2,2-difluoroethyl, 2,2-dichloro-2-fluoroethyl, 2,2,2-trichloroethyl, pentafluoroethyl and the like.

The term "$C_1$-$C_6$-alkoxy" as used herein and in the term $C_1$-$C_6$-alkoxycarbonyl refers to a straight-chain or branched saturated alkyl group having 1 to 6 carbon atoms, preferably 1 to 3 carbon atoms ($C_1$-$C_3$-alkoxy) (as mentioned above) which is attached via an oxygen atom. Examples for $C_1$-$C_3$-alkoxy include methoxy, ethoxy, $OCH_2$—$C_2H_5$ (propoxy) and $OCH(CH_3)_2$ (isopropoxy). Examples for $C_1$-$C_6$-alkoxy further encompass n-butoxy, $OCH(CH_3)C_2H_5$ (sec-butoxy), $OCH_2CH(CH_3)_2$ (isobutoxy), $OC(CH_3)_3$ (tert-butoxy), n-pentoxy, 1-methylbutoxy, 2-methylbutoxy, 3-methylbutoxy, 1,1-dimethyl-propoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethyl-butoxy, 1,2-dimethylbutoxy, 1,3-dimethylbutoxy, 2,2-dimethylbutoxy, 2,3-dimethyl-butoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "$C_1$-$C_6$-haloalkoxy" as used herein refers to a $C_1$-$C_6$-alkoxy group as mentioned above wherein the hydrogen atoms are partially or fully substituted by fluorine, chlorine, bromine and/or iodine. Preferred are $C_1$-$C_3$-haloalkoxy groups, i.e. $C_1$-$C_3$-alkoxy groups as mentioned above wherein the hydrogen atoms are partially or fully substituted by fluorine, chlorine, bromine and/or iodine, for example chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy and 1-(bromomethyl)-2-bromo-ethoxy. Examples for $C_1$-$C_6$-haloalkoxy further encompass 4-fluorobutoxy, 4-chloro-butoxy, 4-bromobutoxy, nonafluorobutoxy, 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy and dodecafluorohexoxy. Particularly preferred are chloromethoxy, fluorometh-oxy, difluoromethoxy, trifluoromethoxy, 2-fluoroethoxy, 2-chloroethoxy and 2,2,2-trifluoroethoxy.

The term "$C_1$-$C_6$-alkylcarbonyl" as used herein refers to a straight-chain or branched saturated alkyl group having 1 to 6 carbon atoms, preferably 1 to 4 carbon atoms (=$C_1$-$C_4$-alkylcarbonyl) (as mentioned above) bonded via the carbon atom of the carbonyl group at any bond in the alkyl group. Examples for $C_1$-$C_4$-alkylcarbonyl include $C(O)CH_3$, $C(O)C_2H_5$, n-propylcarbonyl, 1-methylethylcarbonyl, n-butylcarbonyl, 1-methyl propylcarbonyl, 2-methylpropylcarbonyl and 1,1-dimethylethylcarbonyl. Examples for $C_1$-$C_6$-alkylcarbonyl further encompass n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methyl pentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethyl butylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl and the like.

The term "$C_1$-$C_6$-alkoxycarbonyl" as used herein refers to a straight-chain or branched alkoxy group (as mentioned above) having 1 to 6 carbon atoms, preferably 1 to 4 carbon atoms (=$C_1$-$C_4$-alkoxycarbonyl) attached via the carbon atom of the carbonyl group (R—O—C(O)—; R=alkyl). Examples for $C_1$-$C_4$-alkoxycarbonyl include $C(O)OCH_3$, $C(O)OC_2H_5$, $C(O)O$—$CH_2$—$C_2H_5$, $C(O)OCH(CH_3)_2$, n-butoxycarbonyl, $C(O)OCH(CH_3)$—$C_2H_5$, $C(O)OCH_2CH(CH_3)_2$ and $C(O)OC(CH_3)_3$. Examples for $C_1$-$C_6$-alkoxycarbonyl further encompass n-pentoxycarbonyl, 1-methylbutoxycarbonyl, 2-methylbutoxycarbonyl, 3 methylbutoxycarbonyl, 2,2-dimethylpropoxycarbonyl, 1-ethylpropoxycarbonyl, n hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3 dimethylbutoxycarbonyl, 2,2-dimethylbutoxycarbonyl, 2,3-dimethylbutoxycarbonyl, 3,3-dimethyl butoxycarbonyl, 1-ethylbutoxycarbonyl, 2-ethylbutoxycarbonyl, 1,1,2 trimethylpropoxycarbonyl, 1,2,2-trimethylpropoxycarbonyl, 1-ethyl-1-methylpropoxycarbonyl or 1-ethyl-2-methylpropoxycarbonyl.

The term "$C_1$-$C_6$-alkylcarbonyloxy" as used herein refers to a straight-chain or branched saturated alkyl group having 1 to 6 carbon atoms, preferably 1 to 4 carbon atoms (=$C_1$-$C_4$-alkylcarbonyloxy) (as mentioned above) bonded via the carbon atom of the carbonyloxy group at any bond in the alkyl group. Examples for $C_1$-$C_4$-alkylarbonyloxy include O—CO—$CH_3$, O—CO—$C_2H_5$, n-propylcarbonyloxy, 1-methylethylcarbonyloxy, n-butylcarbonyloxy, 1-methylpropylcarbonyloxy, 2-ethylpropylcarbonyloxy and 1,1-dimethylethylcarbonyloxy. Examples for $C_1$-$C_6$-alkylcarbonyloxy further encompass n-pentylcarbonyloxy, 1-methylbutylcarbonyloxy, 2-methyl butylcarbonyloxy, 3-methylbutylcarbonyloxy, 1,1-dimethylpropylcarbonyloxy or 1,2-dimethylpropylcarbonyloxy.

The term "$C_1$-$C_6$-alkylthio "($C_1$-$C_6$-alkylsulfanyl: $C_1$-$C_6$-alkyl-S—)" as used herein refers to a straight-chain or branched saturated alkyl group having 1 to 6 carbon atoms, preferably 1 to 3 carbon atoms (=$C_1$-$C_3$-alkylthio) (as mentioned above) which is attached via a sulfur atom. Examples for $C_1$-$C_3$-alkylthio include methylthio, ethylthio, propylthio and 1-methylethylthio. Examples for $C_1$-$C_6$-alkylthio further encompass butylthio, 1-methylpropylthio, 2-methylpropylthio and 1,1-dimethylethylthio. n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutythio, 2,2-dimethylbutylthio, 2,3-dimethylbutylthio, 3,3-dimethylbutylthio, 1-ethylbutlthio, 2-ethylbutylthio, 1,1,2-trimethylpropylthio, 1,2,2-trimethylpropylthio, 1-ethyl-1-methylpropylthio and 1-ethyl-2-methylpropylthio.

The term "$C_1$-$C_6$-haloalkylthio" as used herein refers to a $C_1$-$C_6$-alkylthio group as mentioned above wherein the hydrogen atoms are partially or fully substituted by fluorine, chlorine, bromine and/or iodine. Preferred are $C_1$-$C_3$-haloalkylthio groups, i.e. $C_1$-$C_3$-alkylthio groups as mentioned above wherein the hydrogen atoms are partially or fully substituted by fluorine, chlorine, bromine and/or iodine, for example chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethyl-thio, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio or 1-(bromomethyl)-2-bromoethylthio. Examples for $C_1$-$C_6$-haloalkylthio further encompass 4-fluorobutylthio, 4-chlorobutylthio, 4-bromobutylthio, nonafluorobutylthio, 5-fluoro-1-pentylthio, 5-chloro-1-pentylthio, 5-bromo-1-pentylthio, 5-iodo-1-pentylthio, 5,5,5-trichloro-1-pentylthio, undecafluoropentylthio, 6-fluoro-1-hexylthio, 6-chloro-1-hexylthio, 6-bromo-1-hexylthio, 6-iodo-1-hexylthio, 6,6,6-trichloro-1-hexylthio and dodecafluorohexylthio. Particularly preferred are chloromethyl-thio, fluoromethylthio, difluoromethylthio, trifluoromethylthio, 2-fluoroethylthio, 2-chloroethylthio and 2,2,2-trifluoroethylthio.

The term "$C_1$-$C_6$-alkylsulfoxyl" ($C_1$-$C_6$-alkylsulfinyl: $C_1$-$C_6$-alkyl-S(=O)—), as used herein refers to a straight-chain or branched saturated alkyl group (as mentioned above) having 1 to 6 carbon atoms, preferably 1 to 4 carbon atoms (=$C_1$-$C_4$-alkylsulfoxyl) bonded through the sulfur atom of the sulfoxyl group at any position in the alkyl group. Examples for $C_1$-$C_4$-alkylsulfoxyl include S(O)$CH_3$, S(O)$C_2H_5$, n-propylsulfinyl, 1-methylethylsulfinyl, n-butylsulfinyl, 1-methylpropylsulfinyl, 2-methylpropylsulfinyl and 1,1-dimethylethylsulfinyl. Examples for $C_1$-$C_6$-alkylsulfinyl further encompass n-pentylsulfinyl, 1-methylbutylsulfinyl, 2-methylbutylsulfinyl, 3 methylbutylsulfinyl, 1,1-dimethylpropylsulfinyl, 1,2-dimethylpropylsulfinyl, 2,2 dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2 dimethylbutylsulfinyl, 2,3-dimethylbutylsulfinyl, 3,3-dimethylbutylsulfinyl, 1 ethylbutylsulfinyl, 2-ethylbutylsulfinyl, 1,1,2-trimethylpropylsulfinyl, 1,2,2 trimethylpropylsulfinyl, 1-ethyl-1-methyl propylsulfinyl and 1-ethyl-2-methyl propylsulfinyl.

The term "$C_1$-$C_6$-alkylsulfonyl" ($C_1$-$C_6$-alkyl-S(=O)$_2$—) as used herein refers to a straight-chain or branched saturated alkyl group having 1 to 6 carbon atoms, preferably 1 to 4 carbon atoms (=$C_1$-$C_4$-alkylsulfonyl) (as mentioned above) which is bonded via the sulfur atom of the sulfonyl group at any position in the alkyl group. Examples for $C_1$-$C_4$-alkylsulfonyl include $SC_2$—$CH_3$, $SC_2$—$C_2H_5$, n-propylsulfonyl, $SC_2$—CH($CH_3$)$_2$, n-butylsulfonyl, 1-methylpropylsulfonyl, 2-methylpropylsulfonyl and $SO_2$—C($CH_3$)$_3$. Examples for $C_1$-$C_6$-alkylsulfonyl further encompass n pentylsulfonyl, 1-methylbutyl-sulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2 dimethylbutylsulfonyl, 1,3-dimethylbutylsulfonyl, 2,2-dimethylbutylsulfonyl, 2,3 dimethylbutylsulfonyl, 3,3-dimethylbutylsulfonyl, 1-ethylbutylsulfonyl, 2 ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

The term "$C_1$-$C_6$-alkylamino" refers to a secondary amino group carrying one alkyl group as defined above, e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino.

The term "di($C_1$-$C_6$-alkyl)amino)" refers to a tertiary amino group carrying two alkyl radicals as defined above, e.g. dimethylamino, diethylamino, di-n-propylamino, diisopropylamino, N-ethyl-N-methylamino, N-(n-propyl)-N-methylamino, N-(isopropyl)-N-methylamino, N-(n-butyl)-N-methylamino, N-(n-pentyl)-N-methylamino, N-(2-butyl)-N-methylamino, N-(isobutyl)-N-methylamino, N-(n-pentyl)-N-methylamino, N-(n-propyl)-N-ethylamino, N-(isopropyl)-N-ethylamino, N-(n-butyl)-N-ethylamino, N-(n-pentyl)-N-ethylamino, N-(2-butyl)-N-ethylamino, N-(isobutyl)-N-ethylamino and the like.

The term "$C_2$-$C_6$-alkenyl" as used herein and in the alkenyl moieties of $C_2$-$C_6$-alkenyloxy, $C_2$-$C_6$-alkenylamino, $C_2$-$C_6$-alkenylthio, $C_2$-$C_6$-alkenylsulfonyl, $C_2$-$C_6$-alkenylcarbonyl, $C_2$-$C_6$-alkenyloxycarbonyl and $C_2$-$C_6$-alkenylcarbonyloxy refers to a straight-chain or branched unsaturated hydrocarbon group having 2 to 6 carbon atoms and a double bond in any position, such as ethenyl, 1-propenyl, 2 propenyl, 1-methyl-ethenyl, 1-butenyl, 2-butenyl, 3-butenyl, 1-methyl-1-propenyl, 2 methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1 methyl-2-butenyl, 2-methyl-2-butenyl, 3-methyl-2-butenyl, 1-methyl-3-butenyl, 2 methyl-3-butenyl, 3-methyl-3-butenyl, 1,1-dimethyl-2-propenyl, 1,2-dimethyl-1 propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3 methyl-2-pentenyl, 4-methyl-2-pentenyl, 1-methyl-3-pentenyl, 2-methyl-3-pentenyl, 3 methyl-3-pentenyl, 4-methyl-3-pentenyl, 1-methyl-4-pentenyl, 2-methyl-4-pentenyl, 3 methyl-4-pentenyl, 4-methyl-4-pentenyl, 1,1-dimethyl-2-butenyl, 1,1-dimethyl-3 butenyl, 1,2-dimethyl-1-butenyl, 1,2-dimethyl-2-butenyl, 1,2-dimethyl-3-butenyl, 1,3 dimethyl-1-butenyl, 1,3-dimethyl-2-butenyl, 1,3-dimethyl-3-butenyl, 2,2-dimethyl-3 butenyl, 2,3-dimethyl-1-butenyl, 2,3-dimethyl-2-butenyl, 2,3-dimethyl-3-butenyl, 3,3 dimethyl-1-butenyl, 3,3-dimethyl-2-butenyl, 1-ethyl-1-butenyl, 1-ethyl-2-butenyl, 1 ethyl-3-butenyl, 2-ethyl-1-butenyl, 2-ethyl-2-butenyl, 2-ethyl-3-butenyl, 1,1,2 trimethyl-2-propenyl, 1-ethyl-1-methyl-2-propenyl, 1-ethyl-2-methyl-1-propenyl and 1-ethyl-2-methyl-2-propenyl.

The term, "$C_2$-$C_6$-alkenyloxy" as used herein refers to a straight-chain or branched alkenyl group having 2 to 6 carbon atoms (as mentioned above) which is attached via an oxygen atom, such as vinyloxy, allyloxy (propen-3-yloxy), methallyloxy, buten-4-yloxy and the like.

The term "$C_2$-$C_6$-alkenylthio" as used herein refers to a straight-chain or branched alkenyl group having 2 to 6 carbon atoms (as mentioned above) which is attached via a sulfur atom, for example vinylsulfanyl, allylsulfanyl (propen-3-ylthio), methallylsufanyl, buten-4-ylsulfanyl and the like.

The term "$C_2$-$C_6$-alkenylcarbonyl" as used herein refers to a straight-chain or branched alkenyl group having 2 to 6 carbon atoms (as mentioned above) which is bonded via the carbon atom of the carbonyl group at any bond in the alkenyl group, for example vinylcarbonyl, allylcarbonyl (propen-3-ylcarbonyl), methallylcarbonyl, buten-4-yl-carbonyl and the like.

The term "$C_2$-$C_6$-alkenyloxycarbonyl" as used herein refers to a straight-chain or branched alkenyl group having 2 to 6 carbon atoms (as mentioned above) which is bonded via the carbon atom of the oxycarbonyl group (RO—C(O)—; R=$C_2$-$C_6$-alkenyl), for example vinyloxycarbonyl, allyloxycarbonyl (propen-3-yloxycarbonyl), methallyloxycarbonyl, buten-4-yloxycarbonyl and the like.

The term "$C_2$-$C_6$-alkenylcarbonyloxy" as used herein refers to a straight-chain or branched alkenyl group having 2 to 6 carbon atoms (as mentioned above) which is bonded via the oxygen atom of the carbonyloxy group (R—C(O)—O—; R=$C_2$-$C_6$-alkenyl), for example vinylcarbonyloxy, allylcarbonyloxy (propen-3-ylcarbonyloxy), methallylcarbonyloxy, buten-4-ylcarbonyloxy and the like.

The term "$C_2$-$C_6$-alkenylamino" as used herein refers to a straight-chain or branched alkenyl group having 2 to 6 carbon atoms (as mentioned above) which is attached via a sulfur atom, for example vinylamino, allylamino (propen-3-ylamino), methallylamino, buten-4-ylamino and the like.

The term "$C_2$-$C_6$-alkenylsulfonyl" as used herein refers to a straight-chain or branched alkenyl group having 2 to 6 carbon atoms (as mentioned above) which is attached via a sulfonyl group ($SO_2$), for example vinylsulfonyl, allylsulfonyl(propen-3-ylsulfonyl), methallylsufonyl, buten-4-ylsulfonyl and the like.

The term "$C_2$-$C_6$-alkynyl" as used herein and in the alkynyl moieties of $C_2$-$C_6$-alkynyloxy, $C_2$-$C_6$-alkynylamino, $C_2$-$C_6$-alkynylthio, $C_2$-$C_6$-alkynylsulfonyl, $C_2$-$C_6$-alkynylcarbonyl, $C_2$-$C_6$-alkynyloxycarbonyl and $C_2$-$C_6$-alkynylcarbonyloxy refers to a straight-chain or branched unsaturated hydrocarbon group having 2 to 6 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2 yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methyl pent-2-yn-4-yl or 4-methyl pent-2-yn-5-yl and the like.

The term, "$C_2$-$C_6$-alkynyloxy" as used herein refers to a straight-chain or branched alkynyl group having 2 to 6 carbon atoms (as mentioned above) which is attached via an oxygen atom, such as propargyloxy(propyn-3-yloxy), butyn-3-yloxy, butyn-4-yloxy and the like.

The term "$C_2$-$C_6$-alkynylthio" as used herein refers to a straight-chain or branched alkynyl group having 2 to 6 carbon atoms (as mentioned above) which is attached via a sulfur atom, such as propargylsulfanyl(propyn-3-ylthio), butyn-3-ylsufanyl, butyn-4-ylsulfanyl and the like.

The term "$C_2$-$C_6$-alkynylcarbonyl" as used herein refers to a straight-chain or branched alkynyl group having 2 to 6 carbon atoms (as mentioned above) which is bonded via the carbon atom of the carbonyl group at any bond in the alkynyl group, for example propargylcarbonyl(propyn-3-ylcarbonyl), butyn-3-ylcarbonyl, butyn-4-ylcarbonyl and the like.

The term "$C_2$-$C_6$-alkynyloxycarbonyl" as used herein refers to a straight-chain or branched alkynyl group having 2 to 6 carbon atoms (as mentioned above) which is bonded via the carbon atom of the oxycarbonyl group (RO—C(O)—; R=$C_2$-$C_6$-alkynyl), for example propargyloxycarbonyl(propyn-3-yloxycarbonyl), butyn-3-yloxycarbonyl, butyn-4-yloxycarbonyl and the like.

The term "$C_2$-$C_6$-alkynylcarbonyloxy" as used herein refers to a straight-chain or branched alkynyl group having 2 to 6 carbon atoms (as mentioned above) which is bonded via the oxygen atom of the carbonyloxy group (R—C(O)—O—; R=$C_2$-$C_6$-alkynyl), for example propargylcarbonyloxy (propyn-3-ylcarbonyloxy), butyn-3-ylcarbonyloxy, butyn-4-ylcarbonyloxy and the like.

The term "$C_2$-$C_6$-alkynylamino" as used herein refers to a straight-chain or branched alkynyl group having 2 to 6 carbon atoms (as mentioned above) which is attached via a sulfur atom, such as propargylamino(propyn-3-ylamino), butyn-3-amino, butyn-4-ylamino and the like.

The term "$C_2$-$C_6$-alkynylsulfonyl" as used herein refers to a straight-chain or branched alkynyl group having 2 to 6 carbon atoms (as mentioned above) which is attached via a sulfonyl ($SO_2$) group, such as propargylsulfonyl(propin-3-yltsulfonyl), butyn-3-ylsufonyl butyn-4-ylsulfonyl and the like.

The term "$C_3$-$C_{12}$-cycloalkyl" as used herein refers to a mono- or bi- or polycyclic hydrocarbon radical having 3 to 12 (=$C_3$-$C_{12}$-cycloalkyl), frequently 3 to 8 carbon atoms (=$C_3$-$C_8$-cycloalkyl), in particular 3 to 6 carbon atoms (=$C_3$-$C_6$-cycloalkyl). Examples of monocyclic radicals comprise cyclo-propyl, cyclobutyl, cyclopentyl, cyclohexyl, cycloheptyl, cyclooctyl, cyclononyl and cyclodecyl. Examples of bicyclic radicals comprise bicyclo[2.2.1]heptyl, bicyclo[3.1.1]heptyl, bicyclo[2.2.2]octyl and bicyclo[3.2.1]octyl.

The term "aryl" as used herein refers to a $C_6$-$C_{14}$ carboaromatic group, such as phenyl, naphthyl, anthracenyl and phenanthrenyl. Preferably, aryl is phenyl.

The term "aryloxy" refers to aryl as defined above which is bound via an oxygen atom to the remainder of the molecule. Examples are phenoxy and naphthoxy.

The term "arylthio" refers to aryl as defined above which is bound via a sulfur atom to the remainder of the molecule. Examples are phenoxy and naphthoxy.

Phenyl fused to phenyl is naphthyl.

Phenyl fused to a 5- or 6-membered non-aromatic (i.e. saturated or partially unsaturated) heterocyclic ring is for example 2,3-dihydrobenzofuranyl, benzoxolanyl, 2,3-dihydrobenzothienyl, indolinyl, chromanyl, chromenyl, benzodioxanyl and the like. Ex-amples for phenyl fused to a 5- or 6-membered aromatic heterocyclic ring (=fused to a 5- or 6-membered heteroaromatic ring) are given below.

The term "hetaryl" ("momo or bicyclic 5- to 10-membered heteroaromatic ring") as used herein refers to a monocyclic heteroaromatic radical which has 5 or 6 ring members, which may be fused to a carbocyclic or heterocyclic 5, 6 or 7 membered ring thus having a total number of ring members from 8 to 10, wherein in each case 1, 2, 3 or 4, preferably 1, 2 or 3, of these ring members are heteroatoms selected, independently from each other, from the group consisting of oxygen, nitrogen and sulfur. The heteraryl radical may be attached to the remainder of the molecule via a carbon ring member or via a nitrogen ring member. The carbocyclic or heterocyclic fused ring is selected from $C_5$-$C_7$-cycloalkyl, 5 to 7 membered heterocyclyl and phenyl.

Examples for monocyclic 5- to 6-membered heteroaromatic rings include triazinyl, pyrazinyl, pyrimidyl, pyridazinyl, pyridyl, thienyl, furyl, pyrrolyl, pyrazolyl, imidazolyl, triazolyl, tetrazolyl, thiazolyl, oxazolyl, thiadiazolyl, oxadiazolyl, isothiazolyl and isoxazolyl.

Examples for 5- to 6-membered heteroaromatic rings being fused to a phenyl ring (or for a phenyl ring fused to a 5- to 6-membered heteroaromatic ring) are quinolinyl, isoquinolinyl, indolyl, indolizinyl, isoindolyl, indazolyl, benzofuryl, benzthienyl, benzo[b]thiazolyl, benzoxazolyl, benzthiazolyl, benzoxazolyl, and benzimidazolyl. Examples for 5- to 6-membered heteroaromatic rings being fused to a cycloalkenyl ring are dihydroindolyl, dihydroindolizinyl, dihydroisoindolyl, dihydrochinolinyl, dihydroisochinolinyl, chromenyl, chromanyl and the like.

The term "hetaryloxy" refers to hetaryl as defined above which is bound via an oxygen atom to the remainder of the molecule.

The term "hetarylthio" refers to hetaryl as defined above which is bound via a sulfur atom to the remainder of the molecule.

The term "heterocyclyl" ("saturated or partially unsaturated heterocycle") comprises nonaromatic saturated or partially unsaturated heterocyclic rings having 5 or 6 ring members and 1, 2, 3 or 4, preferably 1, 2 or 3 heteroatoms as ring members. The heterocyclic radical may be attached to the remainder of the molecule via a carbon ring member or via a nitrogen ring member. Examples for non-aromatic rings include pyrrolidinyl, pyrazolinyl, imidazolinyl, pyrrolinyl, pyrazolinyl, imidazolinyl, tetrahydrofuranyl, dihydrofuranyl, 1,3-dioxolanyl, dioxolenyl, thiolanyl, dihydrothienyl, oxazolidinyl, isoxazolidinyl, oxazolinyl, isoxazolinyl, thiazolinyl, isothiazolinyl, thiazolidinyl, isothiazolidinyl, oxathiolanyl, piperidinyl, piperazinyl, pyranyl, dihydropyranyl, tetrahydropyranyl, 1,3- and 1,4-dioxanyl, thiopyranyl, dihydrothiopyranyl, tetrahydrothiopyranyl, morpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "heterocyclyloxy" refers to heterocyclyl as defined above which is bound via an oxygen atom to the remainder of the molecule.

The term "heterocyclylthio" refers to heterocyclyl as defined above which is bound via a sulfur atom to the remainder of the molecule.

The term "linear or branched $C_1$-$C_6$-alkanediyl" as used herein refers to a straight-chain or branched saturated alkyl group having 1 to 6 carbon atoms (as mentioned above), where one of the hydrogen atoms in these groups is replaced by a further bonding position. Examples for linear $C_1$-$C_6$-alkanediyl comprise methyldiyl, ethane-1,2-diyl, propane-1,3-diyl, butane-1,4-diyl, pentane-1,5-diyl, hexane-1,6-diyl. Examples for branched $C_1$-$C_6$-alkanediyl comprise ethyl-1,1-diyl, propyl-1,1-diyl, butyl-1,1-diyl, 1-methylethane-1,2-diyl, 1,2-dimethylethane-1,2-diyl, 1-ethylethane-1,2-diyl, 1-methylpropane-1,3-diyl, 2-methylpropan-1,3-diyl and the like.

The group of compounds of formula I includes compounds, wherein A is a radical of formula A.1, referred to as compounds of formula I.1, and compounds, wherein A is a radical of formula A.2, referred to as compounds of formula I.2.

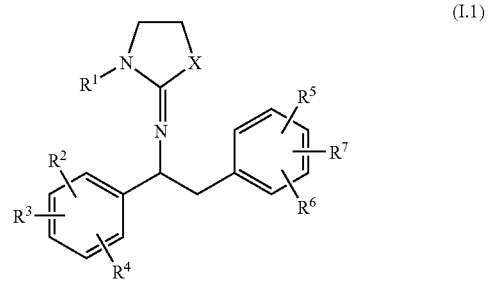

(I.1)

-continued

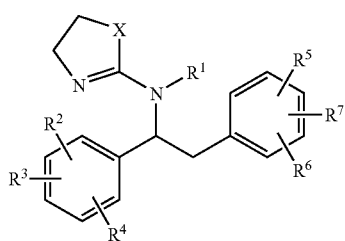

(I.2)

A preferred embodiment of the invention relates to compounds of the formula I.1, as shown herein.

The remarks made below concerning preferred embodiments of the variables of the compounds of formula I as well as of formulae I.1 and I.2, of the features of the use and method according to the invention and of the composition of the invention are valid on their own as well as preferably in combination with each other.

The group X is preferably a sulfur atom.

Preferably, $R^1$ is selected from the group consisting of —C(=O)—$R^C$, —C(=O)—$OR^D$, —C(=O)—$SR^E$, —C(=O)—$NR^{B1}R^{Bt}$, —C(=S)—$R^{C'}$, —C(=S)—$OR^{D'}$, —C(=S)—$SR^{E'}$, —C(=S)—$NR^{B1}R^{B2}$, —C(=$NR^{1e}$)—$R^{C'}$, —C(=$NR^{1f}$)—$OR^{Dt}$, —C(=$NR^{1g}$)—$SR^{Et}$, —C(=$NR^{1h}$)—$NR^{B1}R^{B2}$, wherein $R^{B1}$, $R^{B2}$, $R^{B2t}$, $R^C$, $R^{Ct}$, $R^D$, $R^{Dt}$, $R^e$, $R^{Et}$, $R^{1e}$, $R^{1f}$, $R^{1g}$ and $R^{1h}$ have one of the meanings given before. More preferably $R^1$ is —C(=S)—$NR^{B1}R^{B2}$, wherein $R^{B1}$ and $R^{B2}$ have one of the meanings given before.

The radicals $R^{B1}$ and $R^{B2}$ are preferably selected, independently of each other, from the group consisting of hydrogen, $C_1$-$C_3$-alkyl, $C_2$-$C_3$-alkenyl, $C_2$-$C_3$-alkynyl, wherein the last three mentioned radicals may carry 1 or 2 substituents selected independently from halogen, $C_1$-$C_3$-alkoxy and $C_1$-$C_3$-haloalkoxy, $C_3$-$C_6$-cycloalkyl which is unsubstituted or may carry 1, 2 or 3 substituents $R^{1e}$, phenyl which is unsubstituted or may carry 1, 2 or 3 substituents $R^{1f}$, pyridyl which is unsubstituted or may carry 1, 2 or 3 substituents $R^h$, wherein $R^{1e}$, $R^{1f}$ and $R^{1h}$ have one of the meanings given before.

The radical $R^{B2t}$ is preferably selected from the group consisting of $C_3$-$C_6$-cycloalkyl which is unsubstituted or may carry 1, 2 or 3 substituents $R^{1e}$, phenyl which is unsubstituted or may carry 1, 2 or 3 substituents $R^f$, and pyridyl which is unsubstituted or may carry 1, 2 or 3 substituents $R^h$, wherein $R^{1e}$, $R^{1f}$ and $R^{1h}$ have one of the meanings given before.

The radical $R^C$ is preferably selected from, $C_1$-$C_3$-alkyl which carries 1 or 2 radicals selected from C(=O)OH, aryloxy, arylthio or $C_1$-$C_4$-alkoxycarbonyl, wherein the three last mentioned radicals are unsubstituted or may carry 1 or 2 groups selected independently from CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_6$-cycloalkyl.

The radical $R^{Ct}$ is preferably selected from the group consisting of hydrogen, $C_1$-$C_3$-alkyl, $C_2$-$C_3$-alkenyl, $C_2$-$C_3$-alkynyl, wherein the last three mentioned radicals may carry 1 or 2 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_6$-cycloalkyl, $C_3$-$C_6$-cycloalkyl which is unsubstituted or may carry 1, 2 or 3 substituents $R^{1e}$, phenyl which is unsubstituted or may carry 1, 2 or 3 substituents $R^{1f}$, and pyridyl which is unsubstituted or may carry 1, 2 or 3 substituents $R^{1h}$, wherein $R^{1e}$, $R^{1f}$ and $R^{1h}$ have one of the meanings given before.

The radicals $R^D$, $R^E$, independently of each other, are preferably selected from the group consisting of $C_2$-$C_3$-alkenyl, $C_2$-$C_3$-alkynyl, wherein the last two mentioned radicals may carry 1, 2 or 3 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_6$-cycloalkyl, $C_3$-$C_6$-cycloalkyl which is unsubstituted or may carry 1, 2 or 3 substituents $R^{1e}$, phenyl which is unsubstituted or may carry 1, 2 or 3 substituents $R^{1f}$, and pyridyl which is unsubstituted or may carry 1, 2 or 3 substituents $R^{1h}$, wherein $R^{1e}$, $R^{1f}$ and $R^{1h}$ have one of the meanings given before.

The radicals $R^{Dt}$, $R^{Et}$, independently of each other, preferably have one of the preferred meanings given for $R^D$, $R^E$ or are selected from hydrogen or $C_1$-$C_3$-alkyl which is unsubstituted or carries 1, 2 or 3 substituents selected independently from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_6$-cycloalkyl.

Also preferred are compounds of formula I, wherein $R^1$ is selected from the group consisting of $C_1$-$C_8$-alkenyl, $C_1$-$C_8$-alkynyl and $C_3$-$C_8$-cycloalkyl, which is unsubstituted or may carry 1 to 4 substituents $R^{1e}$ as defined before.

Also preferred are compounds of formula I, wherein $R^1$ is selected from the group consisting of —S(=O)—$R^F$, —S(=O)$_2$—$R^G$, —S(=O)$_2$—$NR^{B1}R^{B2t}$, —P(=O)$R^{H1}R^{H2}$, —P(=S)$R^{H1}R^{H2}$, wherein $R^{B1}$, $R^{B2t}$, $R^F$, $R^G$, $R^{H1}$ and $R^{H2}$ have one of the meanings given before.

The radicals $R^F$, $R^G$, $R^{H1}$ and $R^{H2}$, independently of each other, are preferably selected from the group consisting of hydrogen $C_1$-$C_3$-alkyl, $C_2$-$C_3$-alkenyl, $C_2$-$C_3$-alkynyl, wherein the last three mentioned radicals may carry 1, 2 or 3 substituents selected, independently of each other, from halogen, $C_1$-$C_3$-alkoxy, $C_1$-$C_3$-haloalkoxy, $C_1$-$C_3$-alkylthio, $C_1$-$C_3$-haloalkylthio and $C_3$-$C_6$-cycloalkyl, $C_3$-$C_6$-cycloalkyl which is unsubstituted or may carry 1, 2 or 3 substituents $R^{1e}$, phenyl which is unsubstituted or may carry 1, 2 or 3 substituents $R^{1f}$, and pyridyl which is unsubstituted or may carry 1, 2 or 3 substituents $R^{1h}$, wherein $R^{1e}$, $R^{1f}$ and $R^{1h}$ have one of the meanings given before.

The radical $R^2$ preferably is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy. More preferably $R^2$ is selected from hydrogen, fluoro, chloro, bromo, methyl, methoxy, difluoromethyl, trifluoromethyl, difluoromethoxy and trifluoromethoxy.

The radical $R^3$ preferably is selected from hydrogen, halogen, $C_1$-$C_3$-alkyl and $C_1$-$C_3$-haloalkyl. More preferably $R^2$ is selected from hydrogen, fluoro, chloro, bromo, methyl, difluoromethyl and trifluoromethyl.

Also preferred are compounds of formula I, wherein $R^2$ together with $R^3$ forms a bivalent radical selected from —O—$CH_2$—O—, —O—$CH_2$—$CH_2$— or —O—$CF_2$—O—.

The radical $R^4$ preferably is selected from hydrogen, halogen, $C_1$-$C_3$-alkyl, $C_1$-$C_3$-alkoxy, $C_1$-$C_3$-haloalkyl and $C_1$-$C_3$-haloalkoxy. More preferably $R^4$ is selected from hydrogen, fluoro, chloro, bromo, methyl, methoxy, difluoromethyl, difluoromethoxy and trifluoromethoxy.

In one preferred embodiment of the invention $R^2$ and $R^3$ are different from hydrogen.

In another preferred embodiment of the invention $R^2$ and $R^4$ are different from hydrogen.

The radical $R^5$ preferably is selected from hydrogen, halogen, $C_1$-$C_3$-alkyl, $C_1$-$C_3$-alkoxy, $C_1$-$C_3$-haloalkyl and $C_1$-$C_3$-haloalkoxy. More preferably $R^5$ is selected from hydrogen, fluoro, chloro, bromo, methyl, methoxy, difluoromethyl, trifluoromethyl, difluoromethoxy and trifluoromethoxy.

The radical $R^6$ preferably is selected from halogen, $C_1$-$C_3$-alkyl, $C_1$-$C_3$-alkoxy, $C_1$-$C_3$-haloalkyl and $C_1$-$C_3$-haloalkoxy. More preferably $R^6$ is selected from fluoro, chloro, bromo, methyl, methoxy, difluoromethyl, trifluoromethyl, difluoromethoxy and trifluoromethoxy.

The radical $R^7$ is preferably hydrogen. Likewise preferred are compounds wherein $R^7$ is halogen, $C_1$-$C_3$-alkyl, $C_1$-$C_3$-alkoxy, $C_1$-$C_3$-haloalkyl or $C_1$-$C_3$-haloalkoxy. In particular, $R^7$ is selected from hydrogen, fluoro, chloro, bromo, methyl, methoxy, difluoromethyl, trifluoromethyl, difluoromethoxy and trifluoromethoxy.

Preferably the aromatic moiety

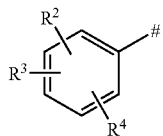

in the formulae I, I.1. and I.2, wherein the radicals $R^2$, $R^3$ and $R^4$ have one of the meanings given before and # denotes the bonding position of formula I, is selected from aromatic moieties, wherein $R^2$ is attached at the carbon atom in ortho-position relative to the bonding position of the remainder of the compound of formula I, $R^3$ is attached at the carbon atom next to the group $CR^2$ and in meta-position relative to the bonding position and $R^4$ is attached at the carbon atom in para-position to the group $CR^2$, as shown in the following formula Ar 1:

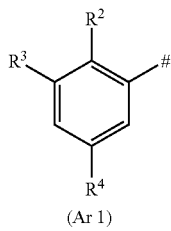

(Ar 1)

wherein the radicals $R^2$, $R^3$ and $R^4$ have one of the meanings given before, in particular one of the preferred meanings and # each time denotes the bonding position of the remainder of formula I.

In the moiety Ar 1 the radical $R^2$ is preferably selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy. More preferably, $R^2$ is selected from hydrogen, fluoro, chloro, bromo, methyl, methoxy, difluoromethyl, trifluoromethyl, difluoromethoxy and trifluoromethoxy.

In the moiety Ar 1 the radical $R^3$ is preferably selected from hydrogen, halogen, $C_1$-$C_3$-alkyl and $C_1$-$C_3$-haloalkyl. More preferably $R^2$ is selected from hydrogen, fluoro, chloro, bromo, methyl, difluoromethyl and trifluoromethyl.

Also preferred are compounds of formula I, where in the moiety Ar 1 the radical $R^2$ together with $R^3$ forms a bivalent radical selected from —O—$CH_2$—O—, —O—$CH_2$—$CH_2$— or —O—$CF_2$—O—.

In the moiety Ar 1 the radical $R^4$ is preferably selected from hydrogen, halogen, $C_1$-$C_3$-alkyl, $C_1$-$C_3$-alkoxy, $C_1$-$C_3$-haloalkyl and $C_1$-$C_3$-haloalkoxy. More preferably $R^4$ is selected from hydrogen, fluoro, chloro, bromo, methyl, methoxy, difluoromethyl, trifluoromethyl, difluoromethoxy and trifluoromethoxy.

In one preferred embodiment of the invention the radicals $R^2$ and $R^3$ in the moiety Ar 1 are different from hydrogen.

In another preferred embodiment of the invention the radicals $R^2$ and $R^4$ in the moiety Ar 1 are different from hydrogen.

Preferably the aromatic moiety,

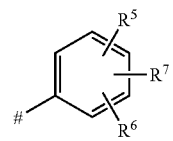

wherein the radicals $R^5$ and $R^6$ have one of the meaning given before and # denotes the bonding position of the remainder formula I, is selected from aromatic moieties, wherein $R^5$ is attached at the carbon atom in meta-position relative to the bonding position of the remainder of the compound of formula I, $R^6$ is attached at the carbon atom in the remaining meta-position relative to the bonding position and $R^7$ is hydrogen, as shown in the following formula Ar 2:

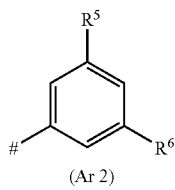

(Ar 2)

wherein the radicals $R^5$ and $R^6$ have one of the meaning given before and # denotes the bonding position of the remainder of formula I.

In the above moiety Ar 2 the radical $R^5$ is preferably selected from hydrogen, halogen, $C_1$-$C_3$-alkyl, $C_1$-$C_3$-alkoxy, $C_1$-$C_3$-haloalkyl and $C_1$-$C_3$-haloalkoxy. More preferably $R^5$ is selected from hydrogen, fluoro, chloro, bromo, methyl, methoxy, difluoromethyl, trifluoromethyl, difluoromethoxy and trifluoromethoxy.

In the above moiety Ar 2 radical $R^6$ is preferably selected from halogen, $C_1$-$C_3$-alkyl, $C_1$-$C_3$-alkoxy, $C_1$-$C_3$-haloalkyl and $C_1$-$C_3$-haloalkoxy. More preferably $R^6$ is selected from fluoro, chloro, bromo, methyl, methoxy, difluoromethyl, trifluoromethyl, difluoromethoxy and trifluoromethoxy.

A preferred embodiment of the invention relates to the compounds of formula I'

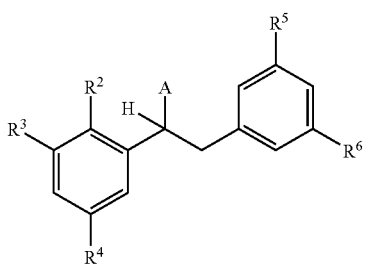

(I')

wherein A, $R^2$, $R^3$, $R^4$, $R^5$ and $R^6$ have one of the meanings given before.

The group of compounds of formula I' includes compounds, wherein A is a radical of formula A.1, referred to hereinafter as compounds of formula I'.1, and compounds, wherein A is a radical of formula A.2, referred to hereinafter as compounds of formula I'.2.

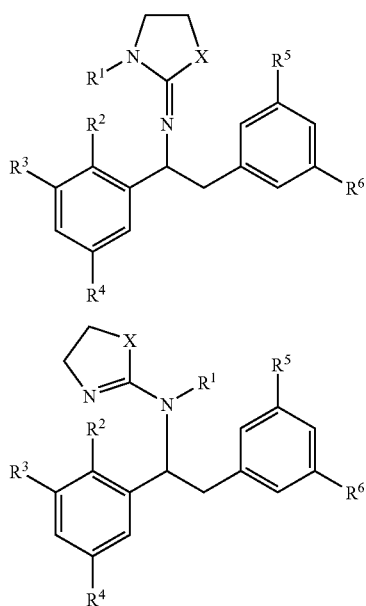

(I'.1)

(I'.2)

A very preferred embodiment of the invention relates to the compounds of formula I'.1, as shown herein.

In formulae I'.1 and I'.2 $R^1$ preferably has one of the meanings which are given above as a preferred meaning. X is in particular a sulfur atom.

In a more preferred embodiment the invention relates to compounds of formula I, especially compounds of formulae I.1, I.2, I', I'.1 and I'.2, wherein $R^2$ is selected from hydrogen, halogen, $C_1$-$C_3$-alkyl, $C_1$-$C_3$-alkoxy, $C_1$-$C_3$-haloalkyl and $C_1$-$C_3$-haloalkoxy, in particular hydrogen, fluoro, chloro, bromo, methyl, methoxy, difluoromethyl, trifluoromethyl, difluoromethoxy and trifluoromethoxy;

$R^3$ is selected from hydrogen, halogen, $C_1$-$C_3$-alkyl and $C_1$-$C_3$-haloalkyl, in particular hydrogen, fluoro, chloro, bromo, methyl, difluoromethyl and trifluoromethyl; or $R^2$ together with $R^3$ forms a bivalent radical selected from —O—$CH_2$—$CH_2$-, —O—$CH_2$—O— or —O—$CF_2$—O—;

$R^4$ is selected from hydrogen, halogen, $C_1$-$C_3$-alkyl, $C_1$-$C_3$-alkoxy, $C_1$-$C_3$-haloalkyl and $C_1$-$C_3$-haloalkoxy, in particular hydrogen, fluoro, chloro, bromo, methyl, methoxy, difluoromethyl, trifluoromethyl, difluoromethoxy and trifluoromethoxy;

$R^5$ is selected from hydrogen, halogen, $C_1$-$C_3$-alkyl, $C_1$-$C_3$-alkoxy, $C_1$-$C_3$-haloalkyl and $C_1$-$C_3$-haloalkoxy, in particular hydrogen, fluoro, chloro, bromo, methyl, methoxy, difluoromethyl, trifluoromethyl, difluoromethoxy and trifluoromethoxy; and $R^6$ is selected from halogen, $C_1$-$C_3$-alkyl, $C_1$-$C_3$-alkoxy, $C_1$-$C_3$-haloalkyl and $C_1$-$C_3$-haloalkoxy, in particular fluoro, chloro, bromo, methyl, methoxy, difluoromethyl, trifluoromethyl, difluoromethoxy and trifluoromethoxy;

or the enantiomers, diastereomers or salts thereof.

In one preferred embodiment of the invention the radicals $R^2$ and $R^3$ in the formulae I.1, I. 2, I',I'.1 and I'.2 are different from hydrogen.

In another preferred embodiment of the invention the radicals $R^2$ and $R^4$ in the formulae I.1, I.2, I', I'.1 and I'.2 are different from hydrogen.

Examples of particularly preferred compounds of the general formula I are the compounds compiled in Tables A to Q below. Moreover, the meanings mentioned for the individual variables in the tables are per se, independently of the combination in which they are mentioned, a particularly preferred embodiment of the substituents in question.

Table A: Examples of preferred compounds of formula I'.1 are the compounds of formula I'.1-A,

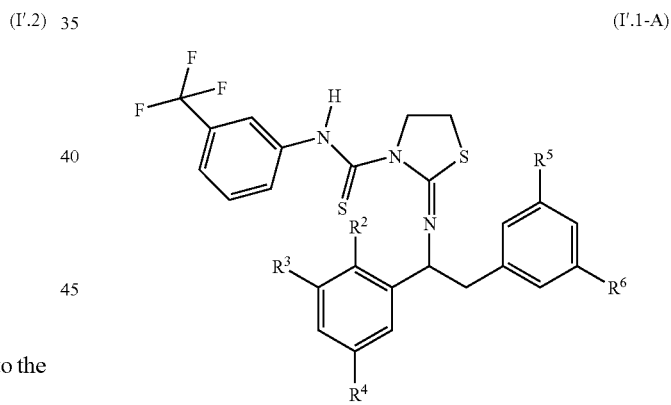

(I'.1-A)

wherein $R^2$, $R^3$, $R^4$, $R^5$ and $R^6$ have the meanings corresponding to one line of the following table 1 (compounds I'.1-A.1 to I'.1-A.2500).

TABLE 1

| | $R^2$ | $R^3$ | $R^4$ | $R^5$ | $R^6$ |
|---|---|---|---|---|---|
| A-1 | F | H | H | H | F |
| A-2 | Cl | H | H | H | F |
| A-3 | $CH_3$ | H | H | H | F |
| A-4 | $CF_3$ | H | H | H | F |
| A-5 | $OCH_3$ | H | H | H | F |
| A-6 | F | F | H | H | F |
| A-7 | Cl | F | H | H | F |
| A-8 | $CH_3$ | F | H | H | F |
| A-9 | $CF_3$ | F | H | H | F |
| A-10 | $OCH_3$ | F | H | H | F |

TABLE 1-continued

|  | R² | R³ | R⁴ | R⁵ | R⁶ |
|---|---|---|---|---|---|
| A-11 | F | Cl | H | H | F |
| A-12 | Cl | Cl | H | H | F |
| A-13 | CH₃ | Cl | H | H | F |
| A-14 | CF₃ | Cl | H | H | F |
| A-15 | OCH₃ | Cl | H | H | F |
| A-16 | F | CH₃ | H | H | F |
| A-17 | Cl | CH₃ | H | H | F |
| A-18 | CH₃ | CH₃ | H | H | F |
| A-19 | CF₃ | CH₃ | H | H | F |
| A-20 | OCH₃ | CH₃ | H | H | F |
| A-21 | F | CF₃ | H | H | F |
| A-22 | Cl | CF₃ | H | H | F |
| A-23 | CH₃ | CF₃ | H | H | F |
| A-24 | CF₃ | CF₃ | H | H | F |
| A-25 | OCH₃ | CF₃ | H | H | F |
| A-26 | F | H | F | H | F |
| A-27 | Cl | H | F | H | F |
| A-28 | CH₃ | H | F | H | F |
| A-29 | CF₃ | H | F | H | F |
| A-30 | OCH₃ | H | F | H | F |
| A-31 | F | F | F | H | F |
| A-32 | Cl | F | F | H | F |
| A-33 | CH₃ | F | F | H | F |
| A-34 | CF₃ | F | F | H | F |
| A-35 | OCH₃ | F | F | H | F |
| A-36 | F | Cl | F | H | F |
| A-37 | Cl | Cl | F | H | F |
| A-38 | CH₃ | Cl | F | H | F |
| A-39 | CF₃ | Cl | F | H | F |
| A-40 | OCH₃ | Cl | F | H | F |
| A-41 | F | CH₃ | F | H | F |
| A-42 | Cl | CH₃ | F | H | F |
| A-43 | CH₃ | CH₃ | F | H | F |
| A-44 | CF₃ | CH₃ | F | H | F |
| A-45 | OCH₃ | CH₃ | F | H | F |
| A-46 | F | CF₃ | F | H | F |
| A-47 | Cl | CF₃ | F | H | F |
| A-48 | CH₃ | CF₃ | F | H | F |
| A-49 | CF₃ | CF₃ | F | H | F |
| A-50 | OCH₃ | CF₃ | F | H | F |
| A-51 | F | H | Cl | H | F |
| A-52 | Cl | H | Cl | H | F |
| A-53 | CH₃ | H | Cl | H | F |
| A-54 | CF₃ | H | Cl | H | F |
| A-55 | OCH₃ | H | Cl | H | F |
| A-56 | F | F | Cl | H | F |
| A-57 | Cl | F | Cl | H | F |
| A-58 | CH₃ | F | Cl | H | F |
| A-59 | CF₃ | F | Cl | H | F |
| A-60 | OCH₃ | F | Cl | H | F |
| A-61 | F | Cl | Cl | H | F |
| A-62 | Cl | Cl | Cl | H | F |
| A-63 | CH₃ | Cl | Cl | H | F |
| A-64 | CF₃ | Cl | Cl | H | F |
| A-65 | OCH₃ | Cl | Cl | H | F |
| A-66 | F | CH₃ | Cl | H | F |
| A-67 | Cl | CH₃ | Cl | H | F |
| A-68 | CH₃ | CH₃ | Cl | H | F |
| A-69 | CF₃ | CH₃ | Cl | H | F |
| A-70 | OCH₃ | CH₃ | Cl | H | F |
| A-71 | F | CF₃ | Cl | H | F |
| A-72 | Cl | CF₃ | Cl | H | F |
| A-73 | CH₃ | CF₃ | Cl | H | F |
| A-74 | CF₃ | CF₃ | Cl | H | F |
| A-75 | OCH₃ | CF₃ | Cl | H | F |
| A-76 | F | H | CH₃ | H | F |
| A-77 | Cl | H | CH₃ | H | F |
| A-78 | CH₃ | H | CH₃ | H | F |
| A-79 | CF₃ | H | CH₃ | H | F |
| A-80 | OCH₃ | H | CH₃ | H | F |
| A-81 | F | F | CH₃ | H | F |
| A-82 | Cl | F | CH₃ | H | F |
| A-83 | CH₃ | F | CH₃ | H | F |
| A-84 | CF₃ | F | CH₃ | H | F |
| A-85 | OCH₃ | F | CH₃ | H | F |
| A-86 | F | Cl | CH₃ | H | F |
| A-87 | Cl | Cl | CH₃ | H | F |
| A-88 | CH₃ | Cl | CH₃ | H | F |
| A-89 | CF₃ | Cl | CH₃ | H | F |
| A-90 | OCH₃ | Cl | CH₃ | H | F |
| A-91 | F | CH₃ | CH₃ | H | F |
| A-92 | Cl | CH₃ | CH₃ | H | F |
| A-93 | CH₃ | CH₃ | CH₃ | H | F |
| A-94 | CF₃ | CH₃ | CH₃ | H | F |
| A-95 | OCH₃ | CH₃ | CH₃ | H | F |
| A-96 | F | CF₃ | CH₃ | H | F |
| A-97 | Cl | CF₃ | CH₃ | H | F |
| A-98 | CH₃ | CF₃ | CH₃ | H | F |
| A-99 | CF₃ | CF₃ | CH₃ | H | F |
| A-100 | OCH₃ | CF₃ | CH₃ | H | F |
| A-101 | F | H | CF₃ | H | F |
| A-102 | Cl | H | CF₃ | H | F |
| A-103 | CH₃ | H | CF₃ | H | F |
| A-104 | CF₃ | H | CF₃ | H | F |
| A-105 | OCH₃ | H | CF₃ | H | F |
| A-106 | F | F | CF₃ | H | F |
| A-107 | Cl | F | CF₃ | H | F |
| A-108 | CH₃ | F | CF₃ | H | F |
| A-109 | CF₃ | F | CF₃ | H | F |
| A-110 | OCH₃ | F | CF₃ | H | F |
| A-111 | F | Cl | CF₃ | H | F |
| A-112 | Cl | Cl | CF₃ | H | F |
| A-113 | CH₃ | Cl | CF₃ | H | F |
| A-114 | CF₃ | Cl | CF₃ | H | F |
| A-115 | OCH₃ | Cl | CF₃ | H | F |
| A-116 | F | CH₃ | CF₃ | H | F |
| A-117 | Cl | CH₃ | CF₃ | H | F |
| A-118 | CH₃ | CH₃ | CF₃ | H | F |
| A-119 | CF₃ | CH₃ | CF₃ | H | F |
| A-120 | OCH₃ | CH₃ | CF₃ | H | F |
| A-121 | F | CF₃ | CF₃ | H | F |
| A-122 | Cl | CF₃ | CF₃ | H | F |
| A-123 | CH₃ | CF₃ | CF₃ | H | F |
| A-124 | CF₃ | CF₃ | CF₃ | H | F |
| A-125 | OCH₃ | CF₃ | CF₃ | H | F |
| A-126 | F | H | H | F | F |
| A-127 | Cl | H | H | F | F |
| A-128 | CH₃ | H | H | F | F |
| A-129 | CF₃ | H | H | F | F |
| A-130 | OCH₃ | H | H | F | F |
| A-131 | F | F | H | F | F |
| A-132 | Cl | F | H | F | F |
| A-133 | CH₃ | F | H | F | F |
| A-134 | CF₃ | F | H | F | F |
| A-135 | OCH₃ | F | H | F | F |
| A-136 | F | Cl | H | F | F |
| A-137 | Cl | Cl | H | F | F |
| A-138 | CH₃ | Cl | H | F | F |
| A-139 | CF₃ | Cl | H | F | F |
| A-140 | OCH₃ | Cl | H | F | F |
| A-141 | F | CH₃ | H | F | F |
| A-142 | Cl | CH₃ | H | F | F |
| A-143 | CH₃ | CH₃ | H | F | F |
| A-144 | CF₃ | CH₃ | H | F | F |
| A-145 | OCH₃ | CH₃ | H | F | F |
| A-146 | F | CF₃ | H | F | F |
| A-147 | Cl | CF₃ | H | F | F |
| A-148 | CH₃ | CF₃ | H | F | F |
| A-149 | CF₃ | CF₃ | H | F | F |
| A-150 | OCH₃ | CF₃ | H | F | F |
| A-151 | F | H | F | F | F |
| A-152 | Cl | H | F | F | F |
| A-153 | CH₃ | H | F | F | F |
| A-154 | CF₃ | H | F | F | F |
| A-155 | OCH₃ | H | F | F | F |
| A-156 | F | F | F | F | F |
| A-157 | Cl | F | F | F | F |
| A-158 | CH₃ | F | F | F | F |
| A-159 | CF₃ | F | F | F | F |
| A-160 | OCH₃ | F | F | F | F |
| A-161 | F | Cl | F | F | F |
| A-162 | Cl | Cl | F | F | F |
| A-163 | CH₃ | Cl | F | F | F |
| A-164 | CF₃ | Cl | F | F | F |
| A-165 | OCH₃ | Cl | F | F | F |
| A-166 | F | CH₃ | F | F | F |

TABLE 1-continued

| | $R^2$ | $R^3$ | $R^4$ | $R^5$ | $R^6$ |
|---|---|---|---|---|---|
| A-167 | Cl | $CH_3$ | F | F | F |
| A-168 | $CH_3$ | $CH_3$ | F | F | F |
| A-169 | $CF_3$ | $CH_3$ | F | F | F |
| A-170 | $OCH_3$ | $CH_3$ | F | F | F |
| A-171 | F | $CF_3$ | F | F | F |
| A-172 | Cl | $CF_3$ | F | F | F |
| A-173 | $CH_3$ | $CF_3$ | F | F | F |
| A-174 | $CF_3$ | $CF_3$ | F | F | F |
| A-175 | $OCH_3$ | $CF_3$ | F | F | F |
| A-176 | F | H | Cl | F | F |
| A-177 | Cl | H | Cl | F | F |
| A-178 | $CH_3$ | H | Cl | F | F |
| A-179 | $CF_3$ | H | Cl | F | F |
| A-180 | $OCH_3$ | H | Cl | F | F |
| A-181 | F | F | Cl | F | F |
| A-182 | Cl | F | Cl | F | F |
| A-183 | $CH_3$ | F | Cl | F | F |
| A-184 | $CF_3$ | F | Cl | F | F |
| A-185 | $OCH_3$ | F | Cl | F | F |
| A-186 | F | Cl | Cl | F | F |
| A-187 | Cl | Cl | Cl | F | F |
| A-188 | $CH_3$ | Cl | Cl | F | F |
| A-189 | $CF_3$ | Cl | Cl | F | F |
| A-190 | $OCH_3$ | Cl | Cl | F | F |
| A-191 | F | $CH_3$ | Cl | F | F |
| A-192 | Cl | $CH_3$ | Cl | F | F |
| A-193 | $CH_3$ | $CH_3$ | Cl | F | F |
| A-194 | $CF_3$ | $CH_3$ | Cl | F | F |
| A-195 | $OCH_3$ | $CH_3$ | Cl | F | F |
| A-196 | F | $CF_3$ | Cl | F | F |
| A-197 | Cl | $CF_3$ | Cl | F | F |
| A-198 | $CH_3$ | $CF_3$ | Cl | F | F |
| A-199 | $CF_3$ | $CF_3$ | Cl | F | F |
| A-200 | $OCH_3$ | $CF_3$ | Cl | F | F |
| A-201 | F | H | $CH_3$ | F | F |
| A-202 | Cl | H | $CH_3$ | F | F |
| A-203 | $CH_3$ | H | $CH_3$ | F | F |
| A-204 | $CF_3$ | H | $CH_3$ | F | F |
| A-205 | $OCH_3$ | H | $CH_3$ | F | F |
| A-206 | F | F | $CH_3$ | F | F |
| A-207 | Cl | F | $CH_3$ | F | F |
| A-208 | $CH_3$ | F | $CH_3$ | F | F |
| A-209 | $CF_3$ | F | $CH_3$ | F | F |
| A-210 | $OCH_3$ | F | $CH_3$ | F | F |
| A-211 | F | Cl | $CH_3$ | F | F |
| A-212 | Cl | Cl | $CH_3$ | F | F |
| A-213 | $CH_3$ | Cl | $CH_3$ | F | F |
| A-214 | $CF_3$ | Cl | $CH_3$ | F | F |
| A-215 | $OCH_3$ | Cl | $CH_3$ | F | F |
| A-216 | F | $CH_3$ | $CH_3$ | F | F |
| A-217 | Cl | $CH_3$ | $CH_3$ | F | F |
| A-218 | $CH_3$ | $CH_3$ | $CH_3$ | F | F |
| A-219 | $CF_3$ | $CH_3$ | $CH_3$ | F | F |
| A-220 | $OCH_3$ | $CH_3$ | $CH_3$ | F | F |
| A-221 | F | $CF_3$ | $CH_3$ | F | F |
| A-222 | Cl | $CF_3$ | $CH_3$ | F | F |
| A-223 | $CH_3$ | $CF_3$ | $CH_3$ | F | F |
| A-224 | $CF_3$ | $CF_3$ | $CH_3$ | F | F |
| A-225 | $OCH_3$ | $CF_3$ | $CH_3$ | F | F |
| A-226 | F | H | $CF_3$ | F | F |
| A-227 | Cl | H | $CF_3$ | F | F |
| A-228 | $CH_3$ | H | $CF_3$ | F | F |
| A-229 | $CF_3$ | H | $CF_3$ | F | F |
| A-230 | $OCH_3$ | H | $CF_3$ | F | F |
| A-231 | F | F | $CF_3$ | F | F |
| A-232 | Cl | F | $CF_3$ | F | F |
| A-233 | $CH_3$ | F | $CF_3$ | F | F |
| A-234 | $CF_3$ | F | $CF_3$ | F | F |
| A-235 | $OCH_3$ | F | $CF_3$ | F | F |
| A-236 | F | Cl | $CF_3$ | F | F |
| A-237 | Cl | Cl | $CF_3$ | F | F |
| A-238 | $CH_3$ | Cl | $CF_3$ | F | F |
| A-239 | $CF_3$ | Cl | $CF_3$ | F | F |
| A-240 | $OCH_3$ | Cl | $CF_3$ | F | F |
| A-241 | F | $CH_3$ | $CF_3$ | F | F |
| A-242 | Cl | $CH_3$ | $CF_3$ | F | F |
| A-243 | $CH_3$ | $CH_3$ | $CF_3$ | F | F |
| A-244 | $CF_3$ | $CH_3$ | $CF_3$ | F | F |
| A-245 | $OCH_3$ | $CH_3$ | $CF_3$ | F | F |
| A-246 | F | $CF_3$ | $CF_3$ | F | F |
| A-247 | Cl | $CF_3$ | $CF_3$ | F | F |
| A-248 | $CH_3$ | $CF_3$ | $CF_3$ | F | F |
| A-249 | $CF_3$ | $CF_3$ | $CF_3$ | F | F |
| A-250 | $OCH_3$ | $CF_3$ | $CF_3$ | F | F |
| A-251 | F | H | H | Cl | F |
| A-252 | Cl | H | H | Cl | F |
| A-253 | $CH_3$ | H | H | Cl | F |
| A-254 | $CF_3$ | H | H | Cl | F |
| A-255 | $OCH_3$ | H | H | Cl | F |
| A-256 | F | F | H | Cl | F |
| A-257 | Cl | F | H | Cl | F |
| A-258 | $CH_3$ | F | H | Cl | F |
| A-259 | $CF_3$ | F | H | Cl | F |
| A-260 | $OCH_3$ | F | H | Cl | F |
| A-261 | F | Cl | H | Cl | F |
| A-262 | Cl | Cl | H | Cl | F |
| A-263 | $CH_3$ | Cl | H | Cl | F |
| A-264 | $CF_3$ | Cl | H | Cl | F |
| A-265 | $OCH_3$ | Cl | H | Cl | F |
| A-266 | F | $CH_3$ | H | Cl | F |
| A-267 | Cl | $CH_3$ | H | Cl | F |
| A-268 | $CH_3$ | $CH_3$ | H | Cl | F |
| A-269 | $CF_3$ | $CH_3$ | H | Cl | F |
| A-270 | $OCH_3$ | $CH_3$ | H | Cl | F |
| A-271 | F | $CF_3$ | H | Cl | F |
| A-272 | Cl | $CF_3$ | H | Cl | F |
| A-273 | $CH_3$ | $CF_3$ | H | Cl | F |
| A-274 | $CF_3$ | $CF_3$ | H | Cl | F |
| A-275 | $OCH_3$ | $CF_3$ | H | Cl | F |
| A-276 | F | H | F | Cl | F |
| A-277 | Cl | H | F | Cl | F |
| A-278 | $CH_3$ | H | F | Cl | F |
| A-279 | $CF_3$ | H | F | Cl | F |
| A-280 | $OCH_3$ | H | F | Cl | F |
| A-281 | F | F | F | Cl | F |
| A-282 | Cl | F | F | Cl | F |
| A-283 | $CH_3$ | F | F | Cl | F |
| A-284 | $CF_3$ | F | F | Cl | F |
| A-285 | $OCH_3$ | F | F | Cl | F |
| A-286 | F | Cl | F | Cl | F |
| A-287 | Cl | Cl | F | Cl | F |
| A-288 | $CH_3$ | Cl | F | Cl | F |
| A-289 | $CF_3$ | Cl | F | Cl | F |
| A-290 | $OCH_3$ | Cl | F | Cl | F |
| A-291 | F | $CH_3$ | F | Cl | F |
| A-292 | Cl | $CH_3$ | F | Cl | F |
| A-293 | $CH_3$ | $CH_3$ | F | Cl | F |
| A-294 | $CF_3$ | $CH_3$ | F | Cl | F |
| A-295 | $OCH_3$ | $CH_3$ | F | Cl | F |
| A-296 | F | $CF_3$ | F | Cl | F |
| A-297 | Cl | $CF_3$ | F | Cl | F |
| A-298 | $CH_3$ | $CF_3$ | F | Cl | F |
| A-299 | $CF_3$ | $CF_3$ | F | Cl | F |
| A-300 | $OCH_3$ | $CF_3$ | F | Cl | F |
| A-301 | F | H | Cl | Cl | F |
| A-302 | Cl | H | Cl | Cl | F |
| A-303 | $CH_3$ | H | Cl | Cl | F |
| A-304 | $CF_3$ | H | Cl | Cl | F |
| A-305 | $OCH_3$ | H | Cl | Cl | F |
| A-306 | F | F | Cl | Cl | F |
| A-307 | Cl | F | Cl | Cl | F |
| A-308 | $CH_3$ | F | Cl | Cl | F |
| A-309 | $CF_3$ | F | Cl | Cl | F |
| A-310 | $OCH_3$ | F | Cl | Cl | F |
| A-311 | F | Cl | Cl | Cl | F |
| A-312 | Cl | Cl | Cl | Cl | F |
| A-391 | F | $CH_3$ | H | $CH_3$ | F |
| A-392 | Cl | $CH_3$ | H | $CH_3$ | F |
| A-393 | $CH_3$ | $CH_3$ | H | $CH_3$ | F |
| A-394 | $CF_3$ | $CH_3$ | H | $CH_3$ | F |
| A-395 | $OCH_3$ | $CH_3$ | H | $CH_3$ | F |
| A-396 | F | $CF_3$ | H | $CH_3$ | F |
| A-397 | Cl | $CF_3$ | H | $CH_3$ | F |
| A-398 | $CH_3$ | $CF_3$ | H | $CH_3$ | F |
| A-399 | $CF_3$ | $CF_3$ | H | $CH_3$ | F |
| A-400 | $OCH_3$ | $CF_3$ | H | $CH_3$ | F |

TABLE 1-continued

|   | R² | R³ | R⁴ | R⁵ | R⁶ |
|---|---|---|---|---|---|
| A-401 | F | H | F | CH₃ | F |
| A-402 | Cl | H | F | CH₃ | F |
| A-403 | CH₃ | H | F | CH₃ | F |
| A-404 | CF₃ | H | F | CH₃ | F |
| A-405 | OCH₃ | H | F | CH₃ | F |
| A-406 | F | F | F | CH₃ | F |
| A-407 | Cl | F | F | CH₃ | F |
| A-408 | CH₃ | F | F | CH₃ | F |
| A-409 | CF₃ | F | F | CH₃ | F |
| A-410 | OCH₃ | F | F | CH₃ | F |
| A-411 | F | Cl | F | CH₃ | F |
| A-412 | Cl | Cl | F | CH₃ | F |
| A-413 | CH₃ | Cl | F | CH₃ | F |
| A-414 | CF₃ | Cl | F | CH₃ | F |
| A-415 | OCH₃ | Cl | F | CH₃ | F |
| A-416 | F | CH₃ | F | CH₃ | F |
| A-417 | Cl | CH₃ | F | CH₃ | F |
| A-418 | CH₃ | CH₃ | F | CH₃ | F |
| A-419 | CF₃ | CH₃ | F | CH₃ | F |
| A-420 | OCH₃ | CH₃ | F | CH₃ | F |
| A-421 | F | CF₃ | F | CH₃ | F |
| A-422 | Cl | CF₃ | F | CH₃ | F |
| A-423 | CH₃ | CF₃ | F | CH₃ | F |
| A-424 | CF₃ | CF₃ | F | CH₃ | F |
| A-425 | OCH₃ | CF₃ | F | CH₃ | F |
| A-426 | F | H | Cl | CH₃ | F |
| A-427 | Cl | H | Cl | CH₃ | F |
| A-428 | CH₃ | H | Cl | CH₃ | F |
| A-429 | CF₃ | H | Cl | CH₃ | F |
| A-430 | OCH₃ | H | Cl | CH₃ | F |
| A-431 | F | F | Cl | CH₃ | F |
| A-432 | Cl | F | Cl | CH₃ | F |
| A-433 | CH₃ | F | Cl | CH₃ | F |
| A-434 | CF₃ | F | Cl | CH₃ | F |
| A-435 | OCH₃ | F | Cl | CH₃ | F |
| A-436 | F | Cl | Cl | CH₃ | F |
| A-437 | Cl | Cl | Cl | CH₃ | F |
| A-438 | CH₃ | Cl | Cl | CH₃ | F |
| A-439 | CF₃ | Cl | Cl | CH₃ | F |
| A-440 | OCH₃ | Cl | Cl | CH₃ | F |
| A-441 | F | CH₃ | Cl | CH₃ | F |
| A-442 | Cl | CH₃ | Cl | CH₃ | F |
| A-443 | CH₃ | CH₃ | Cl | CH₃ | F |
| A-444 | CF₃ | CH₃ | Cl | CH₃ | F |
| A-445 | OCH₃ | CH₃ | Cl | CH₃ | F |
| A-446 | F | CF₃ | Cl | CH₃ | F |
| A-447 | Cl | CF₃ | Cl | CH₃ | F |
| A-448 | CH₃ | CF₃ | Cl | CH₃ | F |
| A-449 | CF₃ | CF₃ | Cl | CH₃ | F |
| A-450 | OCH₃ | CF₃ | Cl | CH₃ | F |
| A-451 | F | H | CH₃ | CH₃ | F |
| A-452 | Cl | H | CH₃ | CH₃ | F |
| A-453 | CH₃ | H | CH₃ | CH₃ | F |
| A-454 | CF₃ | H | CH₃ | CH₃ | F |
| A-455 | OCH₃ | H | CH₃ | CH₃ | F |
| A-456 | F | F | CH₃ | CH₃ | F |
| A-457 | Cl | F | CH₃ | CH₃ | F |
| A-458 | CH₃ | F | CH₃ | CH₃ | F |
| A-459 | CF₃ | F | CH₃ | CH₃ | F |
| A-460 | OCH₃ | F | CH₃ | CH₃ | F |
| A-461 | F | Cl | CH₃ | CH₃ | F |
| A-462 | Cl | Cl | CH₃ | CH₃ | F |
| A-463 | CH₃ | Cl | CH₃ | CH₃ | F |
| A-464 | CF₃ | Cl | CH₃ | CH₃ | F |
| A-465 | OCH₃ | Cl | CH₃ | CH₃ | F |
| A-466 | F | CH₃ | CH₃ | CH₃ | F |
| A-467 | Cl | CH₃ | CH₃ | CH₃ | F |
| A-468 | CH₃ | CH₃ | CH₃ | CH₃ | F |
| A-469 | CF₃ | CH₃ | CH₃ | CH₃ | F |
| A-470 | OCH₃ | CH₃ | CH₃ | CH₃ | F |
| A-471 | F | CF₃ | CH₃ | CH₃ | F |
| A-472 | Cl | CF₃ | CH₃ | CH₃ | F |
| A-473 | CH₃ | CF₃ | CH₃ | CH₃ | F |
| A-474 | CF₃ | CF₃ | CH₃ | CH₃ | F |
| A-475 | OCH₃ | CF₃ | CH₃ | CH₃ | F |
| A-476 | F | H | CF₃ | CH₃ | F |
| A-477 | Cl | H | CF₃ | CH₃ | F |
| A-478 | CH₃ | H | CF₃ | CH₃ | F |
| A-479 | CF₃ | H | CF₃ | CH₃ | F |
| A-480 | OCH₃ | H | CF₃ | CH₃ | F |
| A-481 | F | F | CF₃ | CH₃ | F |
| A-482 | Cl | F | CF₃ | CH₃ | F |
| A-483 | CH₃ | F | CF₃ | CH₃ | F |
| A-484 | CF₃ | F | CF₃ | CH₃ | F |
| A-485 | OCH₃ | F | CF₃ | CH₃ | F |
| A-486 | F | Cl | CF₃ | CH₃ | F |
| A-487 | Cl | Cl | CF₃ | CH₃ | F |
| A-488 | CH₃ | Cl | CF₃ | CH₃ | F |
| A-489 | CF₃ | Cl | CF₃ | CH₃ | F |
| A-490 | OCH₃ | Cl | CF₃ | CH₃ | F |
| A-491 | F | CH₃ | CF₃ | CH₃ | F |
| A-492 | Cl | CH₃ | CF₃ | CH₃ | F |
| A-493 | CH₃ | CH₃ | CF₃ | CH₃ | F |
| A-494 | CF₃ | CH₃ | CF₃ | CH₃ | F |
| A-495 | OCH₃ | CH₃ | CF₃ | CH₃ | F |
| A-496 | F | CF₃ | CF₃ | CH₃ | F |
| A-497 | Cl | CF₃ | CF₃ | CH₃ | F |
| A-498 | CH₃ | CF₃ | CF₃ | CH₃ | F |
| A-499 | CF₃ | CF₃ | CF₃ | CH₃ | F |
| A-500 | OCH₃ | CF₃ | CF₃ | CH₃ | F |
| A-501 | F | H | H | CF₃ | F |
| A-502 | Cl | H | H | CF₃ | F |
| A-503 | CH₃ | H | H | CF₃ | F |
| A-504 | CF₃ | H | H | CF₃ | F |
| A-505 | OCH₃ | H | H | CF₃ | F |
| A-506 | F | F | H | CF₃ | F |
| A-507 | Cl | F | H | CF₃ | F |
| A-508 | CH₃ | F | H | CF₃ | F |
| A-509 | CF₃ | F | H | CF₃ | F |
| A-510 | OCH₃ | F | H | CF₃ | F |
| A-511 | F | Cl | H | CF₃ | F |
| A-512 | Cl | Cl | H | CF₃ | F |
| A-513 | CH₃ | Cl | H | CF₃ | F |
| A-514 | CF₃ | Cl | H | CF₃ | F |
| A-515 | OCH₃ | Cl | H | CF₃ | F |
| A-516 | F | CH₃ | H | CF₃ | F |
| A-517 | Cl | CH₃ | H | CF₃ | F |
| A-518 | CH₃ | CH₃ | H | CF₃ | F |
| A-519 | CF₃ | CH₃ | H | CF₃ | F |
| A-520 | OCH₃ | CH₃ | H | CF₃ | F |
| A-521 | F | CF₃ | H | CF₃ | F |
| A-522 | Cl | CF₃ | H | CF₃ | F |
| A-523 | CH₃ | CF₃ | H | CF₃ | F |
| A-524 | CF₃ | CF₃ | H | CF₃ | F |
| A-525 | OCH₃ | CF₃ | H | CF₃ | F |
| A-526 | F | H | F | CF₃ | F |
| A-527 | Cl | H | F | CF₃ | F |
| A-528 | CH₃ | H | F | CF₃ | F |
| A-529 | CF₃ | H | F | CF₃ | F |
| A-530 | OCH₃ | H | F | CF₃ | F |
| A-531 | F | F | F | CF₃ | F |
| A-532 | Cl | F | F | CF₃ | F |
| A-533 | CH₃ | F | F | CF₃ | F |
| A-534 | CF₃ | F | F | CF₃ | F |
| A-535 | OCH₃ | F | F | CF₃ | F |
| A-536 | F | Cl | F | CF₃ | F |
| A-537 | Cl | Cl | F | CF₃ | F |
| A-538 | CH₃ | Cl | F | CF₃ | F |
| A-539 | CF₃ | Cl | F | CF₃ | F |
| A-540 | OCH₃ | Cl | F | CF₃ | F |
| A-541 | F | CH₃ | F | CF₃ | F |
| A-542 | Cl | CH₃ | F | CF₃ | F |
| A-543 | CH₃ | CH₃ | F | CF₃ | F |
| A-544 | CF₃ | CH₃ | F | CF₃ | F |
| A-545 | OCH₃ | CH₃ | F | CF₃ | F |
| A-546 | F | CF₃ | F | CF₃ | F |
| A-547 | Cl | CF₃ | F | CF₃ | F |
| A-548 | CH₃ | CF₃ | F | CF₃ | F |
| A-549 | CF₃ | CF₃ | F | CF₃ | F |
| A-550 | OCH₃ | CF₃ | F | CF₃ | F |
| A-551 | F | H | Cl | CF₃ | F |
| A-552 | Cl | H | Cl | CF₃ | F |
| A-553 | CH₃ | H | Cl | CF₃ | F |
| A-554 | CF₃ | H | Cl | CF₃ | F |
| A-555 | OCH₃ | H | Cl | CF₃ | F |
| A-556 | F | F | Cl | CF₃ | F |

TABLE 1-continued

| | R² | R³ | R⁴ | R⁵ | R⁶ |
|---|---|---|---|---|---|
| A-557 | Cl | F | Cl | CF₃ | F |
| A-558 | CH₃ | F | Cl | CF₃ | F |
| A-559 | CF₃ | F | Cl | CF₃ | F |
| A-560 | OCH₃ | F | Cl | CF₃ | F |
| A-561 | F | Cl | Cl | CF₃ | F |
| A-562 | Cl | Cl | Cl | CF₃ | F |
| A-563 | CH₃ | Cl | Cl | CF₃ | F |
| A-564 | CF₃ | Cl | Cl | CF₃ | F |
| A-565 | OCH₃ | Cl | Cl | CF₃ | F |
| A-566 | F | CH₃ | Cl | CF₃ | F |
| A-567 | Cl | CH₃ | Cl | CF₃ | F |
| A-568 | CH₃ | CH₃ | Cl | CF₃ | F |
| A-569 | CF₃ | CH₃ | Cl | CF₃ | F |
| A-570 | OCH₃ | CH₃ | Cl | CF₃ | F |
| A-571 | F | CF₃ | Cl | CF₃ | F |
| A-572 | Cl | CF₃ | Cl | CF₃ | F |
| A-573 | CH₃ | CF₃ | Cl | CF₃ | F |
| A-574 | CF₃ | CF₃ | Cl | CF₃ | F |
| A-575 | OCH₃ | CF₃ | Cl | CF₃ | F |
| A-576 | F | H | CH₃ | CF₃ | F |
| A-577 | Cl | H | CH₃ | CF₃ | F |
| A-578 | CH₃ | H | CH₃ | CF₃ | F |
| A-579 | CF₃ | H | CH₃ | CF₃ | F |
| A-580 | OCH₃ | H | CH₃ | CF₃ | F |
| A-581 | F | F | CH₃ | CF₃ | F |
| A-582 | Cl | F | CH₃ | CF₃ | F |
| A-583 | CH₃ | F | CH₃ | CF₃ | F |
| A-584 | CF₃ | F | CH₃ | CF₃ | F |
| A-585 | OCH₃ | F | CH₃ | CF₃ | F |
| A-586 | F | Cl | CH₃ | CF₃ | F |
| A-587 | Cl | Cl | CH₃ | CF₃ | F |
| A-588 | CH₃ | Cl | CH₃ | CF₃ | F |
| A-589 | CF₃ | Cl | CH₃ | CF₃ | F |
| A-590 | OCH₃ | Cl | CH₃ | CF₃ | F |
| A-591 | F | CH₃ | CH₃ | CF₃ | F |
| A-592 | Cl | CH₃ | CH₃ | CF₃ | F |
| A-593 | CH₃ | CH₃ | CH₃ | CF₃ | F |
| A-594 | CF₃ | CH₃ | CH₃ | CF₃ | F |
| A-595 | OCH₃ | CH₃ | CH₃ | CF₃ | F |
| A-596 | F | CF₃ | CH₃ | CF₃ | F |
| A-597 | Cl | CF₃ | CH₃ | CF₃ | F |
| A-598 | CH₃ | CF₃ | CH₃ | CF₃ | F |
| A-599 | CF₃ | CF₃ | CH₃ | CF₃ | F |
| A-600 | OCH₃ | CF₃ | CH₃ | CF₃ | F |
| A-601 | F | H | CF₃ | CF₃ | F |
| A-602 | Cl | H | CF₃ | CF₃ | F |
| A-603 | CH₃ | H | CF₃ | CF₃ | F |
| A-604 | CF₃ | H | CF₃ | CF₃ | F |
| A-605 | OCH₃ | H | CF₃ | CF₃ | F |
| A-606 | F | F | CF₃ | CF₃ | F |
| A-607 | Cl | F | CF₃ | CF₃ | F |
| A-608 | CH₃ | F | CF₃ | CF₃ | F |
| A-609 | CF₃ | F | CF₃ | CF₃ | F |
| A-610 | OCH₃ | F | CF₃ | CF₃ | F |
| A-611 | F | Cl | CF₃ | CF₃ | F |
| A-612 | Cl | Cl | CF₃ | CF₃ | F |
| A-613 | CH₃ | Cl | CF₃ | CF₃ | F |
| A-614 | CF₃ | Cl | CF₃ | CF₃ | F |
| A-615 | OCH₃ | Cl | CF₃ | CF₃ | F |
| A-616 | F | CH₃ | CF₃ | CF₃ | F |
| A-617 | Cl | CH₃ | CF₃ | CF₃ | F |
| A-618 | CH₃ | CH₃ | CF₃ | CF₃ | F |
| A-619 | CF₃ | CH₃ | CF₃ | CF₃ | F |
| A-620 | OCH₃ | CH₃ | CF₃ | CF₃ | F |
| A-621 | F | CF₃ | CF₃ | CF₃ | F |
| A-622 | Cl | CF₃ | CF₃ | CF₃ | F |
| A-623 | CH₃ | CF₃ | CF₃ | CF₃ | F |
| A-624 | CF₃ | CF₃ | CF₃ | CF₃ | F |
| A-625 | OCH₃ | CF₃ | CF₃ | CF₃ | F |
| A-626 | F | H | H | H | Cl |
| A-627 | Cl | H | H | H | Cl |
| A-628 | CH₃ | H | H | H | Cl |
| A-629 | CF₃ | H | H | H | Cl |
| A-630 | OCH₃ | H | H | H | Cl |
| A-631 | F | F | H | H | Cl |
| A-632 | Cl | F | H | H | Cl |
| A-633 | CH₃ | F | H | H | Cl |
| A-634 | CF₃ | F | H | H | Cl |
| A-635 | OCH₃ | F | H | H | Cl |
| A-636 | F | Cl | H | H | Cl |
| A-637 | Cl | Cl | H | H | Cl |
| A-638 | CH₃ | Cl | H | H | Cl |
| A-639 | CF₃ | Cl | H | H | Cl |
| A-640 | OCH₃ | Cl | H | H | Cl |
| A-641 | F | CH₃ | H | H | Cl |
| A-642 | Cl | CH₃ | H | H | Cl |
| A-643 | CH₃ | CH₃ | H | H | Cl |
| A-644 | CF₃ | CH₃ | H | H | Cl |
| A-645 | OCH₃ | CH₃ | H | H | Cl |
| A-646 | F | CF₃ | H | H | Cl |
| A-647 | Cl | CF₃ | H | H | Cl |
| A-648 | CH₃ | CF₃ | H | H | Cl |
| A-649 | CF₃ | CF₃ | H | H | Cl |
| A-650 | OCH₃ | CF₃ | H | H | Cl |
| A-651 | F | H | F | H | Cl |
| A-652 | Cl | H | F | H | Cl |
| A-653 | CH₃ | H | F | H | Cl |
| A-654 | CF₃ | H | F | H | Cl |
| A-655 | OCH₃ | H | F | H | Cl |
| A-656 | F | F | F | H | Cl |
| A-657 | Cl | F | F | H | Cl |
| A-658 | CH₃ | F | F | H | Cl |
| A-659 | CF₃ | F | F | H | Cl |
| A-660 | OCH₃ | F | F | H | Cl |
| A-661 | F | Cl | F | H | Cl |
| A-662 | Cl | Cl | F | H | Cl |
| A-663 | CH₃ | Cl | F | H | Cl |
| A-664 | CF₃ | Cl | F | H | Cl |
| A-665 | OCH₃ | Cl | F | H | Cl |
| A-666 | F | CH₃ | F | H | Cl |
| A-667 | Cl | CH₃ | F | H | Cl |
| A-668 | CH₃ | CH₃ | F | H | Cl |
| A-669 | CF₃ | CH₃ | F | H | Cl |
| A-670 | OCH₃ | CH₃ | F | H | Cl |
| A-671 | F | CF₃ | F | H | Cl |
| A-672 | Cl | CF₃ | F | H | Cl |
| A-673 | CH₃ | CF₃ | F | H | Cl |
| A-674 | CF₃ | CF₃ | F | H | Cl |
| A-675 | OCH₃ | CF₃ | F | H | Cl |
| A-676 | F | H | Cl | H | Cl |
| A-677 | Cl | H | Cl | H | Cl |
| A-678 | CH₃ | H | Cl | H | Cl |
| A-679 | CF₃ | H | Cl | H | Cl |
| A-680 | OCH₃ | H | Cl | H | Cl |
| A-681 | F | F | Cl | H | Cl |
| A-682 | Cl | F | Cl | H | Cl |
| A-683 | CH₃ | F | Cl | H | Cl |
| A-684 | CF₃ | F | Cl | H | Cl |
| A-685 | OCH₃ | F | Cl | H | Cl |
| A-686 | F | Cl | Cl | H | Cl |
| A-687 | Cl | Cl | Cl | H | Cl |
| A-688 | CH₃ | Cl | Cl | H | Cl |
| A-689 | CF₃ | Cl | Cl | H | Cl |
| A-690 | OCH₃ | Cl | Cl | H | Cl |
| A-691 | F | CH₃ | Cl | H | Cl |
| A-692 | Cl | CH₃ | Cl | H | Cl |
| A-693 | CH₃ | CH₃ | Cl | H | Cl |
| A-694 | CF₃ | CH₃ | Cl | H | Cl |
| A-695 | OCH₃ | CH₃ | Cl | H | Cl |
| A-696 | F | CF₃ | Cl | H | Cl |
| A-697 | Cl | CF₃ | Cl | H | Cl |
| A-698 | CH₃ | CF₃ | Cl | H | Cl |
| A-699 | CF₃ | CF₃ | Cl | H | Cl |
| A-700 | OCH₃ | CF₃ | Cl | H | Cl |
| A-701 | F | H | CH₃ | H | Cl |
| A-702 | Cl | H | CH₃ | H | Cl |
| A-703 | CH₃ | H | CH₃ | H | Cl |
| A-704 | CF₃ | H | CH₃ | H | Cl |
| A-705 | OCH₃ | H | CH₃ | H | Cl |
| A-706 | F | F | CH₃ | H | Cl |
| A-707 | Cl | F | CH₃ | H | Cl |
| A-708 | CH₃ | F | CH₃ | H | Cl |
| A-709 | CF₃ | F | CH₃ | H | Cl |
| A-710 | OCH₃ | F | CH₃ | H | Cl |
| A-711 | F | Cl | CH₃ | H | Cl |
| A-712 | Cl | Cl | CH₃ | H | Cl |

TABLE 1-continued

| | R² | R³ | R⁴ | R⁵ | R⁶ |
|---|---|---|---|---|---|
| A-713 | CH₃ | Cl | CH₃ | H | Cl |
| A-714 | CF₃ | Cl | CH₃ | H | Cl |
| A-715 | OCH₃ | Cl | CH₃ | H | Cl |
| A-716 | F | CH₃ | CH₃ | H | Cl |
| A-717 | Cl | CH₃ | CH₃ | H | Cl |
| A-718 | CH₃ | CH₃ | CH₃ | H | Cl |
| A-719 | CF₃ | CH₃ | CH₃ | H | Cl |
| A-720 | OCH₃ | CH₃ | CH₃ | H | Cl |
| A-721 | F | CF₃ | CH₃ | H | Cl |
| A-722 | Cl | CF₃ | CH₃ | H | Cl |
| A-723 | CH₃ | CF₃ | CH₃ | H | Cl |
| A-724 | CF₃ | CF₃ | CH₃ | H | Cl |
| A-725 | OCH₃ | CF₃ | CH₃ | H | Cl |
| A-726 | F | H | CF₃ | H | Cl |
| A-727 | Cl | H | CF₃ | H | Cl |
| A-728 | CH₃ | H | CF₃ | H | Cl |
| A-729 | CF₃ | H | CF₃ | H | Cl |
| A-730 | OCH₃ | H | CF₃ | H | Cl |
| A-731 | F | F | CF₃ | H | Cl |
| A-732 | Cl | F | CF₃ | H | Cl |
| A-733 | CH₃ | F | CF₃ | H | Cl |
| A-734 | CF₃ | F | CF₃ | H | Cl |
| A-735 | OCH₃ | F | CF₃ | H | Cl |
| A-736 | F | Cl | CF₃ | H | Cl |
| A-737 | Cl | Cl | CF₃ | H | Cl |
| A-738 | CH₃ | Cl | CF₃ | H | Cl |
| A-739 | CF₃ | Cl | CF₃ | H | Cl |
| A-740 | OCH₃ | Cl | CF₃ | H | Cl |
| A-741 | F | CH₃ | CF₃ | H | Cl |
| A-742 | Cl | CH₃ | CF₃ | H | Cl |
| A-743 | CH₃ | CH₃ | CF₃ | H | Cl |
| A-744 | CF₃ | CH₃ | CF₃ | H | Cl |
| A-745 | OCH₃ | CH₃ | CF₃ | H | Cl |
| A-746 | F | CF₃ | CF₃ | H | Cl |
| A-747 | Cl | CF₃ | CF₃ | H | Cl |
| A-748 | CH₃ | CF₃ | CF₃ | H | Cl |
| A-749 | CF₃ | CF₃ | CF₃ | H | Cl |
| A-750 | OCH₃ | CF₃ | CF₃ | H | Cl |
| A-751 | F | H | H | F | Cl |
| A-752 | Cl | H | H | F | Cl |
| A-753 | CH₃ | H | H | F | Cl |
| A-754 | CF₃ | H | H | F | Cl |
| A-755 | OCH₃ | H | H | F | Cl |
| A-756 | F | F | H | F | Cl |
| A-757 | Cl | F | H | F | Cl |
| A-758 | CH₃ | F | H | F | Cl |
| A-759 | CF₃ | F | H | F | Cl |
| A-760 | OCH₃ | F | H | F | Cl |
| A-761 | F | Cl | H | F | Cl |
| A-762 | Cl | Cl | H | F | Cl |
| A-763 | CH₃ | Cl | H | F | Cl |
| A-764 | CF₃ | Cl | H | F | Cl |
| A-765 | OCH₃ | Cl | H | F | Cl |
| A-766 | F | CH₃ | H | F | Cl |
| A-767 | Cl | CH₃ | H | F | Cl |
| A-768 | CH₃ | CH₃ | H | F | Cl |
| A-769 | CF₃ | CH₃ | H | F | Cl |
| A-770 | OCH₃ | CH₃ | H | F | Cl |
| A-771 | F | CF₃ | H | F | Cl |
| A-772 | Cl | CF₃ | H | F | Cl |
| A-773 | CH₃ | CF₃ | H | F | Cl |
| A-774 | CF₃ | CF₃ | H | F | Cl |
| A-775 | OCH₃ | CF₃ | H | F | Cl |
| A-776 | F | H | F | F | Cl |
| A-777 | Cl | H | F | F | Cl |
| A-778 | CH₃ | H | F | F | Cl |
| A-779 | CF₃ | H | F | F | Cl |
| A-780 | OCH₃ | H | F | F | Cl |
| A-781 | F | F | F | F | Cl |
| A-782 | Cl | F | F | F | Cl |
| A-783 | CH₃ | F | F | F | Cl |
| A-784 | CF₃ | F | F | F | Cl |
| A-785 | OCH₃ | F | F | F | Cl |
| A-786 | F | Cl | F | F | Cl |
| A-787 | Cl | Cl | F | F | Cl |
| A-788 | CH₃ | Cl | F | F | Cl |
| A-789 | CF₃ | Cl | F | F | Cl |
| A-790 | OCH₃ | Cl | F | F | Cl |
| A-791 | F | CH₃ | F | F | Cl |
| A-792 | Cl | CH₃ | F | F | Cl |
| A-793 | CH₃ | CH₃ | F | F | Cl |
| A-794 | CF₃ | CH₃ | F | F | Cl |
| A-795 | OCH₃ | CH₃ | F | F | Cl |
| A-796 | F | CF₃ | F | F | Cl |
| A-797 | Cl | CF₃ | F | F | Cl |
| A-798 | CH₃ | CF₃ | F | F | Cl |
| A-799 | CF₃ | CF₃ | F | F | Cl |
| A-800 | OCH₃ | CF₃ | F | F | Cl |
| A-801 | F | H | Cl | F | Cl |
| A-802 | Cl | H | Cl | F | Cl |
| A-803 | CH₃ | H | Cl | F | Cl |
| A-804 | CF₃ | H | Cl | F | Cl |
| A-805 | OCH₃ | H | Cl | F | Cl |
| A-806 | F | F | Cl | F | Cl |
| A-807 | Cl | F | Cl | F | Cl |
| A-808 | CH₃ | F | Cl | F | Cl |
| A-809 | CF₃ | F | Cl | F | Cl |
| A-810 | OCH₃ | F | Cl | F | Cl |
| A-811 | F | Cl | Cl | F | Cl |
| A-812 | Cl | Cl | Cl | F | Cl |
| A-813 | CH₃ | Cl | Cl | F | Cl |
| A-814 | CF₃ | Cl | Cl | F | Cl |
| A-815 | OCH₃ | Cl | Cl | F | Cl |
| A-816 | F | CH₃ | Cl | F | Cl |
| A-817 | Cl | CH₃ | Cl | F | Cl |
| A-818 | CH₃ | CH₃ | Cl | F | Cl |
| A-819 | CF₃ | CH₃ | Cl | F | Cl |
| A-820 | OCH₃ | CH₃ | Cl | F | Cl |
| A-821 | F | CF₃ | Cl | F | Cl |
| A-822 | Cl | CF₃ | Cl | F | Cl |
| A-823 | CH₃ | CF₃ | Cl | F | Cl |
| A-824 | CF₃ | CF₃ | Cl | F | Cl |
| A-825 | OCH₃ | CF₃ | Cl | F | Cl |
| A-826 | F | H | CH₃ | F | Cl |
| A-827 | Cl | H | CH₃ | F | Cl |
| A-828 | CH₃ | H | CH₃ | F | Cl |
| A-829 | CF₃ | H | CH₃ | F | Cl |
| A-830 | OCH₃ | H | CH₃ | F | Cl |
| A-831 | F | F | CH₃ | F | Cl |
| A-832 | Cl | F | CH₃ | F | Cl |
| A-833 | CH₃ | F | CH₃ | F | Cl |
| A-834 | CF₃ | F | CH₃ | F | Cl |
| A-835 | OCH₃ | F | CH₃ | F | Cl |
| A-836 | F | Cl | CH₃ | F | Cl |
| A-837 | Cl | Cl | CH₃ | F | Cl |
| A-838 | CH₃ | Cl | CH₃ | F | Cl |
| A-839 | CF₃ | Cl | CH₃ | F | Cl |
| A-840 | OCH₃ | Cl | CH₃ | F | Cl |
| A-841 | F | CH₃ | CH₃ | F | Cl |
| A-842 | Cl | CH₃ | CH₃ | F | Cl |
| A-843 | CH₃ | CH₃ | CH₃ | F | Cl |
| A-844 | CF₃ | CH₃ | CH₃ | F | Cl |
| A-845 | OCH₃ | CH₃ | CH₃ | F | Cl |
| A-846 | F | CF₃ | CH₃ | F | Cl |
| A-847 | Cl | CF₃ | CH₃ | F | Cl |
| A-848 | CH₃ | CF₃ | CH₃ | F | Cl |
| A-849 | CF₃ | CF₃ | CH₃ | F | Cl |
| A-850 | OCH₃ | CF₃ | CH₃ | F | Cl |
| A-851 | F | H | CF₃ | F | Cl |
| A-852 | Cl | H | CF₃ | F | Cl |
| A-853 | CH₃ | H | CF₃ | F | Cl |
| A-854 | CF₃ | H | CF₃ | F | Cl |
| A-855 | OCH₃ | H | CF₃ | F | Cl |
| A-856 | F | F | CF₃ | F | Cl |
| A-857 | Cl | F | CF₃ | F | Cl |
| A-858 | CH₃ | F | CF₃ | F | Cl |
| A-859 | CF₃ | F | CF₃ | F | Cl |
| A-860 | OCH₃ | F | CF₃ | F | Cl |
| A-861 | F | Cl | CF₃ | F | Cl |
| A-862 | Cl | Cl | CF₃ | F | Cl |
| A-863 | CH₃ | Cl | CF₃ | F | Cl |
| A-864 | CF₃ | Cl | CF₃ | F | Cl |
| A-865 | OCH₃ | Cl | CF₃ | F | Cl |
| A-866 | F | CH₃ | CF₃ | F | Cl |
| A-867 | Cl | CH₃ | CF₃ | F | Cl |
| A-868 | CH₃ | CH₃ | CF₃ | F | Cl |

TABLE 1-continued

| | R² | R³ | R⁴ | R⁵ | R⁶ |
|---|---|---|---|---|---|
| A-869 | CF₃ | CH₃ | CF₃ | F | Cl |
| A-870 | OCH₃ | CH₃ | CF₃ | F | Cl |
| A-871 | F | CF₃ | CF₃ | F | Cl |
| A-872 | Cl | CF₃ | CF₃ | F | Cl |
| A-873 | CH₃ | CF₃ | CF₃ | F | Cl |
| A-874 | CF₃ | CF₃ | CF₃ | F | Cl |
| A-875 | OCH₃ | CF₃ | CF₃ | F | Cl |
| A-876 | F | H | H | Cl | Cl |
| A-877 | Cl | H | H | Cl | Cl |
| A-878 | CH₃ | H | H | Cl | Cl |
| A-879 | CF₃ | H | H | Cl | Cl |
| A-880 | OCH₃ | H | H | Cl | Cl |
| A-881 | F | F | H | Cl | Cl |
| A-882 | Cl | F | H | Cl | Cl |
| A-883 | CH₃ | F | H | Cl | Cl |
| A-884 | CF₃ | F | H | Cl | Cl |
| A-885 | OCH₃ | F | H | Cl | Cl |
| A-886 | F | Cl | H | Cl | Cl |
| A-887 | Cl | Cl | H | Cl | Cl |
| A-888 | CH₃ | Cl | H | Cl | Cl |
| A-889 | CF₃ | Cl | H | Cl | Cl |
| A-890 | OCH₃ | Cl | H | Cl | Cl |
| A-891 | F | CH₃ | H | Cl | Cl |
| A-892 | Cl | CH₃ | H | Cl | Cl |
| A-893 | CH₃ | CH₃ | H | Cl | Cl |
| A-894 | CF₃ | CH₃ | H | Cl | Cl |
| A-895 | OCH₃ | CH₃ | H | Cl | Cl |
| A-896 | F | CF₃ | H | Cl | Cl |
| A-897 | Cl | CF₃ | H | Cl | Cl |
| A-898 | CH₃ | CF₃ | H | Cl | Cl |
| A-899 | CF₃ | CF₃ | H | Cl | Cl |
| A-900 | OCH₃ | CF₃ | H | Cl | Cl |
| A-901 | F | H | F | Cl | Cl |
| A-902 | Cl | H | F | Cl | Cl |
| A-903 | CH₃ | H | F | Cl | Cl |
| A-904 | CF₃ | H | F | Cl | Cl |
| A-905 | OCH₃ | H | F | Cl | Cl |
| A-906 | F | F | F | Cl | Cl |
| A-907 | Cl | F | F | Cl | Cl |
| A-908 | CH₃ | F | F | Cl | Cl |
| A-909 | CF₃ | F | F | Cl | Cl |
| A-910 | OCH₃ | F | F | Cl | Cl |
| A-911 | F | Cl | F | Cl | Cl |
| A-912 | Cl | Cl | F | Cl | Cl |
| A-913 | CH₃ | Cl | F | Cl | Cl |
| A-914 | CF₃ | Cl | F | Cl | Cl |
| A-915 | OCH₃ | Cl | F | Cl | Cl |
| A-916 | F | CH₃ | F | Cl | Cl |
| A-917 | Cl | CH₃ | F | Cl | Cl |
| A-918 | CH₃ | CH₃ | F | Cl | Cl |
| A-919 | CF₃ | CH₃ | F | Cl | Cl |
| A-920 | OCH₃ | CH₃ | F | Cl | Cl |
| A-921 | F | CF₃ | F | Cl | Cl |
| A-922 | Cl | CF₃ | F | Cl | Cl |
| A-923 | CH₃ | CF₃ | F | Cl | Cl |
| A-924 | CF₃ | CF₃ | F | Cl | Cl |
| A-925 | OCH₃ | CF₃ | F | Cl | Cl |
| A-926 | F | H | Cl | Cl | Cl |
| A-927 | Cl | H | Cl | Cl | Cl |
| A-928 | CH₃ | H | Cl | Cl | Cl |
| A-929 | CF₃ | H | Cl | Cl | Cl |
| A-930 | OCH₃ | H | Cl | Cl | Cl |
| A-931 | F | F | Cl | Cl | Cl |
| A-932 | Cl | F | Cl | Cl | Cl |
| A-933 | CH₃ | F | Cl | Cl | Cl |
| A-934 | CF₃ | F | Cl | Cl | Cl |
| A-935 | OCH₃ | F | Cl | Cl | Cl |
| A-936 | F | Cl | Cl | Cl | Cl |
| A-937 | Cl | Cl | Cl | Cl | Cl |
| A-938 | CH₃ | Cl | Cl | Cl | Cl |
| A-939 | CF₃ | Cl | Cl | Cl | Cl |
| A-940 | OCH₃ | Cl | Cl | Cl | Cl |
| A-941 | F | CH₃ | Cl | Cl | Cl |
| A-942 | Cl | CH₃ | Cl | Cl | Cl |
| A-943 | CH₃ | CH₃ | Cl | Cl | Cl |
| A-944 | CF₃ | CH₃ | Cl | Cl | Cl |
| A-945 | OCH₃ | CH₃ | Cl | Cl | Cl |
| A-946 | F | CF₃ | Cl | Cl | Cl |
| A-947 | Cl | CF₃ | Cl | Cl | Cl |
| A-948 | CH₃ | CF₃ | Cl | Cl | Cl |
| A-949 | CF₃ | CF₃ | Cl | Cl | Cl |
| A-950 | OCH₃ | CF₃ | Cl | Cl | Cl |
| A-951 | F | H | CH₃ | Cl | Cl |
| A-952 | Cl | H | CH₃ | Cl | Cl |
| A-953 | CH₃ | H | CH₃ | Cl | Cl |
| A-954 | CF₃ | H | CH₃ | Cl | Cl |
| A-955 | OCH₃ | H | CH₃ | Cl | Cl |
| A-956 | F | F | CH₃ | Cl | Cl |
| A-957 | Cl | F | CH₃ | Cl | Cl |
| A-958 | CH₃ | F | CH₃ | Cl | Cl |
| A-959 | CF₃ | F | CH₃ | Cl | Cl |
| A-960 | OCH₃ | F | CH₃ | Cl | Cl |
| A-961 | F | Cl | CH₃ | Cl | Cl |
| A-962 | Cl | Cl | CH₃ | Cl | Cl |
| A-963 | CH₃ | Cl | CH₃ | Cl | Cl |
| A-964 | CF₃ | Cl | CH₃ | Cl | Cl |
| A-965 | OCH₃ | Cl | CH₃ | Cl | Cl |
| A-966 | F | CH₃ | CH₃ | Cl | Cl |
| A-967 | Cl | CH₃ | CH₃ | Cl | Cl |
| A-968 | CH₃ | CH₃ | CH₃ | Cl | Cl |
| A-969 | CF₃ | CH₃ | CH₃ | Cl | Cl |
| A-970 | OCH₃ | CH₃ | CH₃ | Cl | Cl |
| A-971 | F | CF₃ | CH₃ | Cl | Cl |
| A-972 | Cl | CF₃ | CH₃ | Cl | Cl |
| A-973 | CH₃ | CF₃ | CH₃ | Cl | Cl |
| A-974 | CF₃ | CF₃ | CH₃ | Cl | Cl |
| A-975 | OCH₃ | CF₃ | CH₃ | Cl | Cl |
| A-976 | F | H | CF₃ | Cl | Cl |
| A-977 | Cl | H | CF₃ | Cl | Cl |
| A-978 | CH₃ | H | CF₃ | Cl | Cl |
| A-979 | CF₃ | H | CF₃ | Cl | Cl |
| A-980 | OCH₃ | H | CF₃ | Cl | Cl |
| A-981 | F | F | CF₃ | Cl | Cl |
| A-982 | Cl | F | CF₃ | Cl | Cl |
| A-983 | CH₃ | F | CF₃ | Cl | Cl |
| A-984 | CF₃ | F | CF₃ | Cl | Cl |
| A-985 | OCH₃ | F | CF₃ | Cl | Cl |
| A-986 | F | Cl | CF₃ | Cl | Cl |
| A-987 | Cl | Cl | CF₃ | Cl | Cl |
| A-988 | CH₃ | Cl | CF₃ | Cl | Cl |
| A-989 | CF₃ | Cl | CF₃ | Cl | Cl |
| A-990 | OCH₃ | Cl | CF₃ | Cl | Cl |
| A-991 | F | CH₃ | CF₃ | Cl | Cl |
| A-992 | Cl | CH₃ | CF₃ | Cl | Cl |
| A-993 | CH₃ | CH₃ | CF₃ | Cl | Cl |
| A-994 | CF₃ | CH₃ | CF₃ | Cl | Cl |
| A-995 | OCH₃ | CH₃ | CF₃ | Cl | Cl |
| A-996 | F | CF₃ | CF₃ | Cl | Cl |
| A-997 | Cl | CF₃ | CF₃ | Cl | Cl |
| A-998 | CH₃ | CF₃ | CF₃ | Cl | Cl |
| A-999 | CF₃ | CF₃ | CF₃ | Cl | Cl |
| A-1000 | OCH₃ | CF₃ | CF₃ | Cl | Cl |
| A-1001 | F | H | H | CH₃ | Cl |
| A-1002 | Cl | H | H | CH₃ | Cl |
| A-1003 | CH₃ | H | H | CH₃ | Cl |
| A-1004 | CF₃ | H | H | CH₃ | Cl |
| A-1005 | OCH₃ | H | H | CH₃ | Cl |
| A-1006 | F | F | H | CH₃ | Cl |
| A-1007 | Cl | F | H | CH₃ | Cl |
| A-1008 | CH₃ | F | H | CH₃ | Cl |
| A-1009 | CF₃ | F | H | CH₃ | Cl |
| A-1010 | OCH₃ | F | H | CH₃ | Cl |
| A-1011 | F | Cl | H | CH₃ | Cl |
| A-1012 | Cl | Cl | H | CH₃ | Cl |
| A-1013 | CH₃ | Cl | H | CH₃ | Cl |
| A-1014 | CF₃ | Cl | H | CH₃ | Cl |
| A-1015 | OCH₃ | Cl | H | CH₃ | Cl |
| A-1016 | F | CH₃ | H | CH₃ | Cl |
| A-1017 | Cl | CH₃ | H | CH₃ | Cl |
| A-1018 | CH₃ | CH₃ | H | CH₃ | Cl |
| A-1019 | CF₃ | CH₃ | H | CH₃ | Cl |
| A-1020 | OCH₃ | CH₃ | H | CH₃ | Cl |
| A-1021 | F | CF₃ | H | CH₃ | Cl |
| A-1022 | Cl | CF₃ | H | CH₃ | Cl |
| A-1023 | CH₃ | CF₃ | H | CH₃ | Cl |
| A-1024 | CF₃ | CF₃ | H | CH₃ | Cl |

TABLE 1-continued

| | R² | R³ | R⁴ | R⁵ | R⁶ |
|---|---|---|---|---|---|
| A-1025 | OCH₃ | CF₃ | H | CH₃ | Cl |
| A-1026 | F | H | F | CH₃ | Cl |
| A-1027 | Cl | H | F | CH₃ | Cl |
| A-1028 | CH₃ | H | F | CH₃ | Cl |
| A-1029 | CF₃ | H | F | CH₃ | Cl |
| A-1030 | OCH₃ | H | F | CH₃ | Cl |
| A-1031 | F | F | F | CH₃ | Cl |
| A-1032 | Cl | F | F | CH₃ | Cl |
| A-1033 | CH₃ | F | F | CH₃ | Cl |
| A-1034 | CF₃ | F | F | CH₃ | Cl |
| A-1035 | OCH₃ | F | F | CH₃ | Cl |
| A-1036 | F | Cl | F | CH₃ | Cl |
| A-1037 | Cl | Cl | F | CH₃ | Cl |
| A-1038 | CH₃ | Cl | F | CH₃ | Cl |
| A-1039 | CF₃ | Cl | F | CH₃ | Cl |
| A-1040 | OCH₃ | Cl | F | CH₃ | Cl |
| A-1041 | F | CH₃ | F | CH₃ | Cl |
| A-1042 | Cl | CH₃ | F | CH₃ | Cl |
| A-1043 | CH₃ | CH₃ | F | CH₃ | Cl |
| A-1044 | CF₃ | CH₃ | F | CH₃ | Cl |
| A-1045 | OCH₃ | CH₃ | F | CH₃ | Cl |
| A-1046 | F | CF₃ | F | CH₃ | Cl |
| A-1047 | Cl | CF₃ | F | CH₃ | Cl |
| A-1048 | CH₃ | CF₃ | F | CH₃ | Cl |
| A-1049 | CF₃ | CF₃ | F | CH₃ | Cl |
| A-1050 | OCH₃ | CF₃ | F | CH₃ | Cl |
| A-1051 | F | H | Cl | CH₃ | Cl |
| A-1052 | Cl | H | Cl | CH₃ | Cl |
| A-1053 | CH₃ | H | Cl | CH₃ | Cl |
| A-1054 | CF₃ | H | Cl | CH₃ | Cl |
| A-1055 | OCH₃ | H | Cl | CH₃ | Cl |
| A-1056 | F | F | Cl | CH₃ | Cl |
| A-1057 | Cl | F | Cl | CH₃ | Cl |
| A-1058 | CH₃ | F | Cl | CH₃ | Cl |
| A-1059 | CF₃ | F | Cl | CH₃ | Cl |
| A-1060 | OCH₃ | F | Cl | CH₃ | Cl |
| A-1061 | F | Cl | Cl | CH₃ | Cl |
| A-1062 | Cl | Cl | Cl | CH₃ | Cl |
| A-1063 | CH₃ | Cl | Cl | CH₃ | Cl |
| A-1064 | CF₃ | Cl | Cl | CH₃ | Cl |
| A-1065 | OCH₃ | Cl | Cl | CH₃ | Cl |
| A-1066 | F | CH₃ | Cl | CH₃ | Cl |
| A-1067 | Cl | CH₃ | Cl | CH₃ | Cl |
| A-1068 | CH₃ | CH₃ | Cl | CH₃ | Cl |
| A-1069 | CF₃ | CH₃ | Cl | CH₃ | Cl |
| A-1070 | OCH₃ | CH₃ | Cl | CH₃ | Cl |
| A-1071 | F | CF₃ | Cl | CH₃ | Cl |
| A-1072 | Cl | CF₃ | Cl | CH₃ | Cl |
| A-1073 | CH₃ | CF₃ | Cl | CH₃ | Cl |
| A-1074 | CF₃ | CF₃ | Cl | CH₃ | Cl |
| A-1075 | OCH₃ | CF₃ | Cl | CH₃ | Cl |
| A-1076 | F | H | CH₃ | CH₃ | Cl |
| A-1077 | Cl | H | CH₃ | CH₃ | Cl |
| A-1078 | CH₃ | H | CH₃ | CH₃ | Cl |
| A-1079 | CF₃ | H | CH₃ | CH₃ | Cl |
| A-1080 | OCH₃ | H | CH₃ | CH₃ | Cl |
| A-1081 | F | F | CH₃ | CH₃ | Cl |
| A-1082 | Cl | F | CH₃ | CH₃ | Cl |
| A-1083 | CH₃ | F | CH₃ | CH₃ | Cl |
| A-1084 | CF₃ | F | CH₃ | CH₃ | Cl |
| A-1085 | OCH₃ | F | CH₃ | CH₃ | Cl |
| A-1086 | F | Cl | CH₃ | CH₃ | Cl |
| A-1087 | Cl | Cl | CH₃ | CH₃ | Cl |
| A-1088 | CH₃ | Cl | CH₃ | CH₃ | Cl |
| A-1089 | CF₃ | Cl | CH₃ | CH₃ | Cl |
| A-1090 | OCH₃ | Cl | CH₃ | CH₃ | Cl |
| A-1091 | F | CH₃ | CH₃ | CH₃ | Cl |
| A-1092 | Cl | CH₃ | CH₃ | CH₃ | Cl |
| A-1093 | CH₃ | CH₃ | CH₃ | CH₃ | Cl |
| A-1094 | CF₃ | CH₃ | CH₃ | CH₃ | Cl |
| A-1095 | OCH₃ | CH₃ | CH₃ | CH₃ | Cl |
| A-1096 | F | CF₃ | CH₃ | CH₃ | Cl |
| A-1097 | Cl | CF₃ | CH₃ | CH₃ | Cl |
| A-1098 | CH₃ | CF₃ | CH₃ | CH₃ | Cl |
| A-1099 | CF₃ | CF₃ | CH₃ | CH₃ | Cl |
| A-1100 | OCH₃ | CF₃ | CH₃ | CH₃ | Cl |
| A-1101 | F | H | CF₃ | CH₃ | Cl |
| A-1102 | Cl | H | CF₃ | CH₃ | Cl |
| A-1103 | CH₃ | H | CF₃ | CH₃ | Cl |
| A-1104 | CF₃ | H | CF₃ | CH₃ | Cl |
| A-1105 | OCH₃ | H | CF₃ | CH₃ | Cl |
| A-1106 | F | F | CF₃ | CH₃ | Cl |
| A-1107 | Cl | F | CF₃ | CH₃ | Cl |
| A-1108 | CH₃ | F | CF₃ | CH₃ | Cl |
| A-1109 | CF₃ | F | CF₃ | CH₃ | Cl |
| A-1110 | OCH₃ | F | CF₃ | CH₃ | Cl |
| A-1111 | F | Cl | CF₃ | CH₃ | Cl |
| A-1112 | Cl | Cl | CF₃ | CH₃ | Cl |
| A-1113 | CH₃ | Cl | CF₃ | CH₃ | Cl |
| A-1114 | CF₃ | Cl | CF₃ | CH₃ | Cl |
| A-1115 | OCH₃ | Cl | CF₃ | CH₃ | Cl |
| A-1116 | F | CH₃ | CF₃ | CH₃ | Cl |
| A-1117 | Cl | CH₃ | CF₃ | CH₃ | Cl |
| A-1118 | CH₃ | CH₃ | CF₃ | CH₃ | Cl |
| A-1119 | CF₃ | CH₃ | CF₃ | CH₃ | Cl |
| A-1120 | OCH₃ | CH₃ | CF₃ | CH₃ | Cl |
| A-1121 | F | CF₃ | CF₃ | CH₃ | Cl |
| A-1122 | Cl | CF₃ | CF₃ | CH₃ | Cl |
| A-1123 | CH₃ | CF₃ | CF₃ | CH₃ | Cl |
| A-1124 | CF₃ | CF₃ | CF₃ | CH₃ | Cl |
| A-1125 | OCH₃ | CF₃ | CF₃ | CH₃ | Cl |
| A-1126 | F | H | H | CF₃ | Cl |
| A-1127 | Cl | H | H | CF₃ | Cl |
| A-1128 | CH₃ | H | H | CF₃ | Cl |
| A-1129 | CF₃ | H | H | CF₃ | Cl |
| A-1130 | OCH₃ | H | H | CF₃ | Cl |
| A-1131 | F | F | H | CF₃ | Cl |
| A-1132 | Cl | F | H | CF₃ | Cl |
| A-1133 | CH₃ | F | H | CF₃ | Cl |
| A-1134 | CF₃ | F | H | CF₃ | Cl |
| A-1135 | OCH₃ | F | H | CF₃ | Cl |
| A-1136 | F | Cl | H | CF₃ | Cl |
| A-1137 | Cl | Cl | H | CF₃ | Cl |
| A-1138 | CH₃ | Cl | H | CF₃ | Cl |
| A-1139 | CF₃ | Cl | H | CF₃ | Cl |
| A-1140 | OCH₃ | Cl | H | CF₃ | Cl |
| A-1141 | F | CH₃ | H | CF₃ | Cl |
| A-1142 | Cl | CH₃ | H | CF₃ | Cl |
| A-1143 | CH₃ | CH₃ | H | CF₃ | Cl |
| A-1144 | CF₃ | CH₃ | H | CF₃ | Cl |
| A-1145 | OCH₃ | CH₃ | H | CF₃ | Cl |
| A-1146 | F | CF₃ | H | CF₃ | Cl |
| A-1147 | Cl | CF₃ | H | CF₃ | Cl |
| A-1148 | CH₃ | CF₃ | H | CF₃ | Cl |
| A-1149 | CF₃ | CF₃ | H | CF₃ | Cl |
| A-1150 | OCH₃ | CF₃ | H | CF₃ | Cl |
| A-1151 | F | H | F | CF₃ | Cl |
| A-1152 | Cl | H | F | CF₃ | Cl |
| A-1153 | CH₃ | H | F | CF₃ | Cl |
| A-1154 | CF₃ | H | F | CF₃ | Cl |
| A-1155 | OCH₃ | H | F | CF₃ | Cl |
| A-1156 | F | F | F | CF₃ | Cl |
| A-1157 | Cl | F | F | CF₃ | Cl |
| A-1158 | CH₃ | F | F | CF₃ | Cl |
| A-1159 | CF₃ | F | F | CF₃ | Cl |
| A-1160 | OCH₃ | F | F | CF₃ | Cl |
| A-1161 | F | Cl | F | CF₃ | Cl |
| A-1162 | Cl | Cl | F | CF₃ | Cl |
| A-1163 | CH₃ | Cl | F | CF₃ | Cl |
| A-1164 | CF₃ | Cl | F | CF₃ | Cl |
| A-1165 | OCH₃ | Cl | F | CF₃ | Cl |
| A-1166 | F | CH₃ | F | CF₃ | Cl |
| A-1167 | Cl | CH₃ | F | CF₃ | Cl |
| A-1168 | CH₃ | CH₃ | F | CF₃ | Cl |
| A-1169 | CF₃ | CH₃ | F | CF₃ | Cl |
| A-1170 | OCH₃ | CH₃ | F | CF₃ | Cl |
| A-1171 | F | CF₃ | F | CF₃ | Cl |
| A-1172 | Cl | CF₃ | F | CF₃ | Cl |
| A-1173 | CH₃ | CF₃ | F | CF₃ | Cl |
| A-1174 | CF₃ | CF₃ | F | CF₃ | Cl |
| A-1175 | OCH₃ | CF₃ | F | CF₃ | Cl |
| A-1176 | F | H | Cl | CF₃ | Cl |
| A-1177 | Cl | H | Cl | CF₃ | Cl |
| A-1178 | CH₃ | H | Cl | CF₃ | Cl |
| A-1179 | CF₃ | H | Cl | CF₃ | Cl |
| A-1180 | OCH₃ | H | Cl | CF₃ | Cl |

TABLE 1-continued

| | R² | R³ | R⁴ | R⁵ | R⁶ |
|---|---|---|---|---|---|
| A-1181 | F | F | Cl | CF₃ | Cl |
| A-1182 | Cl | F | Cl | CF₃ | Cl |
| A-1183 | CH₃ | F | Cl | CF₃ | Cl |
| A-1184 | CF₃ | F | Cl | CF₃ | Cl |
| A-1185 | OCH₃ | F | Cl | CF₃ | Cl |
| A-1186 | F | Cl | Cl | CF₃ | Cl |
| A-1187 | Cl | Cl | Cl | CF₃ | Cl |
| A-1188 | CH₃ | Cl | Cl | CF₃ | Cl |
| A-1189 | CF₃ | Cl | Cl | CF₃ | Cl |
| A-1190 | OCH₃ | Cl | Cl | CF₃ | Cl |
| A-1191 | F | CH₃ | Cl | CF₃ | Cl |
| A-1192 | Cl | CH₃ | Cl | CF₃ | Cl |
| A-1193 | CH₃ | CH₃ | Cl | CF₃ | Cl |
| A-1194 | CF₃ | CH₃ | Cl | CF₃ | Cl |
| A-1195 | OCH₃ | CH₃ | Cl | CF₃ | Cl |
| A-1196 | F | CF₃ | Cl | CF₃ | Cl |
| A-1197 | Cl | CF₃ | Cl | CF₃ | Cl |
| A-1198 | CH₃ | CF₃ | Cl | CF₃ | Cl |
| A-1199 | CF₃ | CF₃ | Cl | CF₃ | Cl |
| A-1200 | OCH₃ | CF₃ | Cl | CF₃ | Cl |
| A-1201 | F | H | CH₃ | CF₃ | Cl |
| A-1202 | Cl | H | CH₃ | CF₃ | Cl |
| A-1203 | CH₃ | H | CH₃ | CF₃ | Cl |
| A-1204 | CF₃ | H | CH₃ | CF₃ | Cl |
| A-1205 | OCH₃ | H | CH₃ | CF₃ | Cl |
| A-1206 | F | F | CH₃ | CF₃ | Cl |
| A-1207 | Cl | F | CH₃ | CF₃ | Cl |
| A-1208 | CH₃ | F | CH₃ | CF₃ | Cl |
| A-1209 | CF₃ | F | CH₃ | CF₃ | Cl |
| A-1210 | OCH₃ | F | CH₃ | CF₃ | Cl |
| A-1211 | F | Cl | CH₃ | CF₃ | Cl |
| A-1212 | Cl | Cl | CH₃ | CF₃ | Cl |
| A-1213 | CH₃ | Cl | CH₃ | CF₃ | Cl |
| A-1214 | CF₃ | Cl | CH₃ | CF₃ | Cl |
| A-1215 | OCH₃ | Cl | CH₃ | CF₃ | Cl |
| A-1216 | F | CH₃ | CH₃ | CF₃ | Cl |
| A-1217 | Cl | CH₃ | CH₃ | CF₃ | Cl |
| A-1218 | CH₃ | CH₃ | CH₃ | CF₃ | Cl |
| A-1219 | CF₃ | CH₃ | CH₃ | CF₃ | Cl |
| A-1220 | OCH₃ | CH₃ | CH₃ | CF₃ | Cl |
| A-1221 | F | CF₃ | CH₃ | CF₃ | Cl |
| A-1222 | Cl | CF₃ | CH₃ | CF₃ | Cl |
| A-1223 | CH₃ | CF₃ | CH₃ | CF₃ | Cl |
| A-1224 | CF₃ | CF₃ | CH₃ | CF₃ | Cl |
| A-1225 | OCH₃ | CF₃ | CH₃ | CF₃ | Cl |
| A-1226 | F | H | CF₃ | CF₃ | Cl |
| A-1227 | Cl | H | CF₃ | CF₃ | Cl |
| A-1228 | CH₃ | H | CF₃ | CF₃ | Cl |
| A-1229 | CF₃ | H | CF₃ | CF₃ | Cl |
| A-1230 | OCH₃ | H | CF₃ | CF₃ | Cl |
| A-1231 | F | F | CF₃ | CF₃ | Cl |
| A-1232 | Cl | F | CF₃ | CF₃ | Cl |
| A-1233 | CH₃ | F | CF₃ | CF₃ | Cl |
| A-1234 | CF₃ | F | CF₃ | CF₃ | Cl |
| A-1235 | OCH₃ | F | CF₃ | CF₃ | Cl |
| A-1236 | F | Cl | CF₃ | CF₃ | Cl |
| A-1237 | Cl | Cl | CF₃ | CF₃ | Cl |
| A-1238 | CH₃ | Cl | CF₃ | CF₃ | Cl |
| A-1239 | CF₃ | Cl | CF₃ | CF₃ | Cl |
| A-1240 | OCH₃ | Cl | CF₃ | CF₃ | Cl |
| A-1241 | F | CH₃ | CF₃ | CF₃ | Cl |
| A-1242 | Cl | CH₃ | CF₃ | CF₃ | Cl |
| A-1243 | CH₃ | CH₃ | CF₃ | CF₃ | Cl |
| A-1244 | CF₃ | CH₃ | CF₃ | CF₃ | Cl |
| A-1245 | OCH₃ | CH₃ | CF₃ | CF₃ | Cl |
| A-1246 | F | CF₃ | CF₃ | CF₃ | Cl |
| A-1247 | Cl | CF₃ | CF₃ | CF₃ | Cl |
| A-1248 | CH₃ | CF₃ | CF₃ | CF₃ | Cl |
| A-1249 | CF₃ | CF₃ | CF₃ | CF₃ | Cl |
| A-1250 | OCH₃ | CF₃ | CF₃ | CF₃ | Cl |
| A-1251 | F | H | H | H | CH₃ |
| A-1252 | Cl | H | H | H | CH₃ |
| A-1253 | CH₃ | H | H | H | CH₃ |
| A-1254 | CF₃ | H | H | H | CH₃ |
| A-1255 | OCH₃ | H | H | H | CH₃ |
| A-1256 | F | F | H | H | CH₃ |
| A-1257 | Cl | F | H | H | CH₃ |
| A-1258 | CH₃ | F | H | H | CH₃ |
| A-1259 | CF₃ | F | H | H | CH₃ |
| A-1260 | OCH₃ | F | H | H | CH₃ |
| A-1261 | F | Cl | H | H | CH₃ |
| A-1262 | Cl | Cl | H | H | CH₃ |
| A-1263 | CH₃ | Cl | H | H | CH₃ |
| A-1264 | CF₃ | Cl | H | H | CH₃ |
| A-1265 | OCH₃ | Cl | H | H | CH₃ |
| A-1266 | F | CH₃ | H | H | CH₃ |
| A-1267 | Cl | CH₃ | H | H | CH₃ |
| A-1268 | CH₃ | CH₃ | H | H | CH₃ |
| A-1269 | CF₃ | CH₃ | H | H | CH₃ |
| A-1270 | OCH₃ | CH₃ | H | H | CH₃ |
| A-1271 | F | CF₃ | H | H | CH₃ |
| A-1272 | Cl | CF₃ | H | H | CH₃ |
| A-1273 | CH₃ | CF₃ | H | H | CH₃ |
| A-1274 | CF₃ | CF₃ | H | H | CH₃ |
| A-1275 | OCH₃ | CF₃ | H | H | CH₃ |
| A-1276 | F | H | F | H | CH₃ |
| A-1277 | Cl | H | F | H | CH₃ |
| A-1278 | CH₃ | H | F | H | CH₃ |
| A-1279 | CF₃ | H | F | H | CH₃ |
| A-1280 | OCH₃ | H | F | H | CH₃ |
| A-1281 | F | F | F | H | CH₃ |
| A-1282 | Cl | F | F | H | CH₃ |
| A-1283 | CH₃ | F | F | H | CH₃ |
| A-1284 | CF₃ | F | F | H | CH₃ |
| A-1285 | OCH₃ | F | F | H | CH₃ |
| A-1286 | F | Cl | F | H | CH₃ |
| A-1287 | Cl | Cl | F | H | CH₃ |
| A-1288 | CH₃ | Cl | F | H | CH₃ |
| A-1289 | CF₃ | Cl | F | H | CH₃ |
| A-1290 | OCH₃ | Cl | F | H | CH₃ |
| A-1291 | F | CH₃ | F | H | CH₃ |
| A-1292 | Cl | CH₃ | F | H | CH₃ |
| A-1293 | CH₃ | CH₃ | F | H | CH₃ |
| A-1294 | CF₃ | CH₃ | F | H | CH₃ |
| A-1295 | OCH₃ | CH₃ | F | H | CH₃ |
| A-1296 | F | CF₃ | F | H | CH₃ |
| A-1297 | Cl | CF₃ | F | H | CH₃ |
| A-1298 | CH₃ | CF₃ | F | H | CH₃ |
| A-1299 | CF₃ | CF₃ | F | H | CH₃ |
| A-1300 | OCH₃ | CF₃ | F | H | CH₃ |
| A-1301 | F | H | Cl | H | CH₃ |
| A-1302 | Cl | H | Cl | H | CH₃ |
| A-1303 | CH₃ | H | Cl | H | CH₃ |
| A-1304 | CF₃ | H | Cl | H | CH₃ |
| A-1305 | OCH₃ | H | Cl | H | CH₃ |
| A-1306 | F | F | Cl | H | CH₃ |
| A-1307 | Cl | F | Cl | H | CH₃ |
| A-1308 | CH₃ | F | Cl | H | CH₃ |
| A-1309 | CF₃ | F | Cl | H | CH₃ |
| A-1310 | OCH₃ | F | Cl | H | CH₃ |
| A-1311 | F | Cl | Cl | H | CH₃ |
| A-1312 | Cl | Cl | Cl | H | CH₃ |
| A-1313 | CH₃ | Cl | Cl | H | CH₃ |
| A-1314 | CF₃ | Cl | Cl | H | CH₃ |
| A-1315 | OCH₃ | Cl | Cl | H | CH₃ |
| A-1316 | F | CH₃ | Cl | H | CH₃ |
| A-1317 | Cl | CH₃ | Cl | H | CH₃ |
| A-1318 | CH₃ | CH₃ | Cl | H | CH₃ |
| A-1319 | CF₃ | CH₃ | Cl | H | CH₃ |
| A-1320 | OCH₃ | CH₃ | Cl | H | CH₃ |
| A-1321 | F | CF₃ | Cl | H | CH₃ |
| A-1322 | Cl | CF₃ | Cl | H | CH₃ |
| A-1323 | CH₃ | CF₃ | Cl | H | CH₃ |
| A-1324 | CF₃ | CF₃ | Cl | H | CH₃ |
| A-1325 | OCH₃ | CF₃ | Cl | H | CH₃ |
| A-1326 | F | H | CH₃ | H | CH₃ |
| A-1327 | Cl | H | CH₃ | H | CH₃ |
| A-1328 | CH₃ | H | CH₃ | H | CH₃ |
| A-1329 | CF₃ | H | CH₃ | H | CH₃ |
| A-1330 | OCH₃ | H | CH₃ | H | CH₃ |
| A-1331 | F | F | CH₃ | H | CH₃ |
| A-1332 | Cl | F | CH₃ | H | CH₃ |
| A-1333 | CH₃ | F | CH₃ | H | CH₃ |
| A-1334 | CF₃ | F | CH₃ | H | CH₃ |
| A-1335 | OCH₃ | F | CH₃ | H | CH₃ |
| A-1336 | F | Cl | CH₃ | H | CH₃ |

TABLE 1-continued

| | $R^2$ | $R^3$ | $R^4$ | $R^5$ | $R^6$ |
|---|---|---|---|---|---|
| A-1337 | Cl | Cl | CH$_3$ | H | CH$_3$ |
| A-1338 | CH$_3$ | Cl | CH$_3$ | H | CH$_3$ |
| A-1339 | CF$_3$ | Cl | CH$_3$ | H | CH$_3$ |
| A-1340 | OCH$_3$ | Cl | CH$_3$ | H | CH$_3$ |
| A-1341 | F | CH$_3$ | CH$_3$ | H | CH$_3$ |
| A-1342 | Cl | CH$_3$ | CH$_3$ | H | CH$_3$ |
| A-1343 | CH$_3$ | CH$_3$ | CH$_3$ | H | CH$_3$ |
| A-1344 | CF$_3$ | CH$_3$ | CH$_3$ | H | CH$_3$ |
| A-1345 | OCH$_3$ | CH$_3$ | CH$_3$ | H | CH$_3$ |
| A-1346 | F | CF$_3$ | CH$_3$ | H | CH$_3$ |
| A-1347 | Cl | CF$_3$ | CH$_3$ | H | CH$_3$ |
| A-1348 | CH$_3$ | CF$_3$ | CH$_3$ | H | CH$_3$ |
| A-1349 | CF$_3$ | CF$_3$ | CH$_3$ | H | CH$_3$ |
| A-1350 | OCH$_3$ | CF$_3$ | CH$_3$ | H | CH$_3$ |
| A-1351 | F | H | CF$_3$ | H | CH$_3$ |
| A-1352 | Cl | H | CF$_3$ | H | CH$_3$ |
| A-1353 | CH$_3$ | H | CF$_3$ | H | CH$_3$ |
| A-1354 | CF$_3$ | H | CF$_3$ | H | CH$_3$ |
| A-1355 | OCH$_3$ | H | CF$_3$ | H | CH$_3$ |
| A-1356 | F | F | CF$_3$ | H | CH$_3$ |
| A-1357 | Cl | F | CF$_3$ | H | CH$_3$ |
| A-1358 | CH$_3$ | F | CF$_3$ | H | CH$_3$ |
| A-1359 | CF$_3$ | F | CF$_3$ | H | CH$_3$ |
| A-1360 | OCH$_3$ | F | CF$_3$ | H | CH$_3$ |
| A-1361 | F | Cl | CF$_3$ | H | CH$_3$ |
| A-1362 | Cl | Cl | CF$_3$ | H | CH$_3$ |
| A-1363 | CH$_3$ | Cl | CF$_3$ | H | CH$_3$ |
| A-1364 | CF$_3$ | Cl | CF$_3$ | H | CH$_3$ |
| A-1365 | OCH$_3$ | Cl | CF$_3$ | H | CH$_3$ |
| A-1366 | F | CH$_3$ | CF$_3$ | H | CH$_3$ |
| A-1367 | Cl | CH$_3$ | CF$_3$ | H | CH$_3$ |
| A-1368 | CH$_3$ | CH$_3$ | CF$_3$ | H | CH$_3$ |
| A-1369 | CF$_3$ | CH$_3$ | CF$_3$ | H | CH$_3$ |
| A-1370 | OCH$_3$ | CH$_3$ | CF$_3$ | H | CH$_3$ |
| A-1371 | F | CF$_3$ | CF$_3$ | H | CH$_3$ |
| A-1372 | Cl | CF$_3$ | CF$_3$ | H | CH$_3$ |
| A-1373 | CH$_3$ | CF$_3$ | CF$_3$ | H | CH$_3$ |
| A-1374 | CF$_3$ | CF$_3$ | CF$_3$ | H | CH$_3$ |
| A-1375 | OCH$_3$ | CF$_3$ | CF$_3$ | H | CH$_3$ |
| A-1376 | F | H | H | F | CH$_3$ |
| A-1377 | Cl | H | H | F | CH$_3$ |
| A-1378 | CH$_3$ | H | H | F | CH$_3$ |
| A-1379 | CF$_3$ | H | H | F | CH$_3$ |
| A-1380 | OCH$_3$ | H | H | F | CH$_3$ |
| A-1381 | F | F | H | F | CH$_3$ |
| A-1382 | Cl | F | H | F | CH$_3$ |
| A-1383 | CH$_3$ | F | H | F | CH$_3$ |
| A-1384 | CF$_3$ | F | H | F | CH$_3$ |
| A-1385 | OCH$_3$ | F | H | F | CH$_3$ |
| A-1386 | F | Cl | H | F | CH$_3$ |
| A-1387 | Cl | Cl | H | F | CH$_3$ |
| A-1388 | CH$_3$ | Cl | H | F | CH$_3$ |
| A-1389 | CF$_3$ | Cl | H | F | CH$_3$ |
| A-1390 | OCH$_3$ | Cl | H | F | CH$_3$ |
| A-1391 | F | CH$_3$ | H | F | CH$_3$ |
| A-1392 | Cl | CH$_3$ | H | F | CH$_3$ |
| A-1393 | CH$_3$ | CH$_3$ | H | F | CH$_3$ |
| A-1394 | CF$_3$ | CH$_3$ | H | F | CH$_3$ |
| A-1395 | OCH$_3$ | CH$_3$ | H | F | CH$_3$ |
| A-1396 | F | CF$_3$ | H | F | CH$_3$ |
| A-1397 | Cl | CF$_3$ | H | F | CH$_3$ |
| A-1398 | CH$_3$ | CF$_3$ | H | F | CH$_3$ |
| A-1399 | CF$_3$ | CF$_3$ | H | F | CH$_3$ |
| A-1400 | OCH$_3$ | CF$_3$ | H | F | CH$_3$ |
| A-1401 | F | H | F | F | CH$_3$ |
| A-1402 | Cl | H | F | F | CH$_3$ |
| A-1403 | CH$_3$ | H | F | F | CH$_3$ |
| A-1404 | CF$_3$ | H | F | F | CH$_3$ |
| A-1405 | OCH$_3$ | H | F | F | CH$_3$ |
| A-1406 | F | F | F | F | CH$_3$ |
| A-1407 | Cl | F | F | F | CH$_3$ |
| A-1408 | CH$_3$ | F | F | F | CH$_3$ |
| A-1409 | CF$_3$ | F | F | F | CH$_3$ |
| A-1410 | OCH$_3$ | F | F | F | CH$_3$ |
| A-1411 | F | Cl | F | F | CH$_3$ |
| A-1412 | Cl | Cl | F | F | CH$_3$ |
| A-1413 | CH$_3$ | Cl | F | F | CH$_3$ |
| A-1414 | CF$_3$ | Cl | F | F | CH$_3$ |
| A-1415 | OCH$_3$ | Cl | F | F | CH$_3$ |
| A-1416 | F | CH$_3$ | F | F | CH$_3$ |
| A-1417 | Cl | CH$_3$ | F | F | CH$_3$ |
| A-1418 | CH$_3$ | CH$_3$ | F | F | CH$_3$ |
| A-1419 | CF$_3$ | CH$_3$ | F | F | CH$_3$ |
| A-1420 | OCH$_3$ | CH$_3$ | F | F | CH$_3$ |
| A-1421 | F | CF$_3$ | F | F | CH$_3$ |
| A-1422 | Cl | CF$_3$ | F | F | CH$_3$ |
| A-1423 | CH$_3$ | CF$_3$ | F | F | CH$_3$ |
| A-1424 | CF$_3$ | CF$_3$ | F | F | CH$_3$ |
| A-1425 | OCH$_3$ | CF$_3$ | F | F | CH$_3$ |
| A-1426 | F | H | Cl | F | CH$_3$ |
| A-1427 | Cl | H | Cl | F | CH$_3$ |
| A-1428 | CH$_3$ | H | Cl | F | CH$_3$ |
| A-1429 | CF$_3$ | H | Cl | F | CH$_3$ |
| A-1430 | OCH$_3$ | H | Cl | F | CH$_3$ |
| A-1431 | F | F | Cl | F | CH$_3$ |
| A-1432 | Cl | F | Cl | F | CH$_3$ |
| A-1433 | CH$_3$ | F | Cl | F | CH$_3$ |
| A-1434 | CF$_3$ | F | Cl | F | CH$_3$ |
| A-1435 | OCH$_3$ | F | Cl | F | CH$_3$ |
| A-1436 | F | Cl | Cl | F | CH$_3$ |
| A-1437 | Cl | Cl | Cl | F | CH$_3$ |
| A-1438 | CH$_3$ | Cl | Cl | F | CH$_3$ |
| A-1439 | CF$_3$ | Cl | Cl | F | CH$_3$ |
| A-1440 | OCH$_3$ | Cl | Cl | F | CH$_3$ |
| A-1441 | F | CH$_3$ | Cl | F | CH$_3$ |
| A-1442 | Cl | CH$_3$ | Cl | F | CH$_3$ |
| A-1443 | CH$_3$ | CH$_3$ | Cl | F | CH$_3$ |
| A-1444 | CF$_3$ | CH$_3$ | Cl | F | CH$_3$ |
| A-1445 | OCH$_3$ | CH$_3$ | Cl | F | CH$_3$ |
| A-1446 | F | CF$_3$ | Cl | F | CH$_3$ |
| A-1447 | Cl | CF$_3$ | Cl | F | CH$_3$ |
| A-1448 | CH$_3$ | CF$_3$ | Cl | F | CH$_3$ |
| A-1449 | CF$_3$ | CF$_3$ | Cl | F | CH$_3$ |
| A-1450 | OCH$_3$ | CF$_3$ | Cl | F | CH$_3$ |
| A-1451 | F | H | CH$_3$ | F | CH$_3$ |
| A-1452 | Cl | H | CH$_3$ | F | CH$_3$ |
| A-1453 | CH$_3$ | H | CH$_3$ | F | CH$_3$ |
| A-1454 | CF$_3$ | H | CH$_3$ | F | CH$_3$ |
| A-1455 | OCH$_3$ | H | CH$_3$ | F | CH$_3$ |
| A-1456 | F | F | CH$_3$ | F | CH$_3$ |
| A-1457 | Cl | F | CH$_3$ | F | CH$_3$ |
| A-1458 | CH$_3$ | F | CH$_3$ | F | CH$_3$ |
| A-1459 | CF$_3$ | F | CH$_3$ | F | CH$_3$ |
| A-1460 | OCH$_3$ | F | CH$_3$ | F | CH$_3$ |
| A-1461 | F | Cl | CH$_3$ | F | CH$_3$ |
| A-1462 | Cl | Cl | CH$_3$ | F | CH$_3$ |
| A-1463 | CH$_3$ | Cl | CH$_3$ | F | CH$_3$ |
| A-1464 | CF$_3$ | Cl | CH$_3$ | F | CH$_3$ |
| A-1465 | OCH$_3$ | Cl | CH$_3$ | F | CH$_3$ |
| A-1466 | F | CH$_3$ | CH$_3$ | F | CH$_3$ |
| A-1467 | Cl | CH$_3$ | CH$_3$ | F | CH$_3$ |
| A-1468 | CH$_3$ | CH$_3$ | CH$_3$ | F | CH$_3$ |
| A-1469 | CF$_3$ | CH$_3$ | CH$_3$ | F | CH$_3$ |
| A-1470 | OCH$_3$ | CH$_3$ | CH$_3$ | F | CH$_3$ |
| A-1471 | F | CF$_3$ | CH$_3$ | F | CH$_3$ |
| A-1472 | Cl | CF$_3$ | CH$_3$ | F | CH$_3$ |
| A-1473 | CH$_3$ | CF$_3$ | CH$_3$ | F | CH$_3$ |
| A-1474 | CF$_3$ | CF$_3$ | CH$_3$ | F | CH$_3$ |
| A-1475 | OCH$_3$ | CF$_3$ | CH$_3$ | F | CH$_3$ |
| A-1476 | F | H | CF$_3$ | F | CH$_3$ |
| A-1477 | Cl | H | CF$_3$ | F | CH$_3$ |
| A-1478 | CH$_3$ | H | CF$_3$ | F | CH$_3$ |
| A-1479 | CF$_3$ | H | CF$_3$ | F | CH$_3$ |
| A-1480 | OCH$_3$ | H | CF$_3$ | F | CH$_3$ |
| A-1481 | F | F | CF$_3$ | F | CH$_3$ |
| A-1482 | Cl | F | CF$_3$ | F | CH$_3$ |
| A-1483 | CH$_3$ | F | CF$_3$ | F | CH$_3$ |
| A-1484 | CF$_3$ | F | CF$_3$ | F | CH$_3$ |
| A-1485 | OCH$_3$ | F | CF$_3$ | F | CH$_3$ |
| A-1486 | F | Cl | CF$_3$ | F | CH$_3$ |
| A-1487 | Cl | Cl | CF$_3$ | F | CH$_3$ |
| A-1488 | CH$_3$ | Cl | CF$_3$ | F | CH$_3$ |
| A-1489 | CF$_3$ | Cl | CF$_3$ | F | CH$_3$ |
| A-1490 | OCH$_3$ | Cl | CF$_3$ | F | CH$_3$ |
| A-1491 | F | CH$_3$ | CF$_3$ | F | CH$_3$ |
| A-1492 | Cl | CH$_3$ | CF$_3$ | F | CH$_3$ |

TABLE 1-continued

| | R² | R³ | R⁴ | R⁵ | R⁶ |
|---|---|---|---|---|---|
| A-1493 | CH₃ | CH₃ | CF₃ | F | CH₃ |
| A-1494 | CF₃ | CH₃ | CF₃ | F | CH₃ |
| A-1495 | OCH₃ | CH₃ | CF₃ | F | CH₃ |
| A-1496 | F | CF₃ | CF₃ | F | CH₃ |
| A-1497 | Cl | CF₃ | CF₃ | F | CH₃ |
| A-1498 | CH₃ | CF₃ | CF₃ | F | CH₃ |
| A-1499 | CF₃ | CF₃ | CF₃ | F | CH₃ |
| A-1500 | OCH₃ | CF₃ | CF₃ | F | CH₃ |
| A-1501 | F | H | H | Cl | CH₃ |
| A-1502 | Cl | H | H | Cl | CH₃ |
| A-1503 | CH₃ | H | H | Cl | CH₃ |
| A-1504 | CF₃ | H | H | Cl | CH₃ |
| A-1505 | OCH₃ | H | H | Cl | CH₃ |
| A-1506 | F | F | H | Cl | CH₃ |
| A-1507 | Cl | F | H | Cl | CH₃ |
| A-1508 | CH₃ | F | H | Cl | CH₃ |
| A-1509 | CF₃ | F | H | Cl | CH₃ |
| A-1510 | OCH₃ | F | H | Cl | CH₃ |
| A-1511 | F | Cl | H | Cl | CH₃ |
| A-1512 | Cl | Cl | H | Cl | CH₃ |
| A-1513 | CH₃ | Cl | H | Cl | CH₃ |
| A-1514 | CF₃ | Cl | H | Cl | CH₃ |
| A-1515 | OCH₃ | Cl | H | Cl | CH₃ |
| A-1516 | F | CH₃ | H | Cl | CH₃ |
| A-1517 | Cl | CH₃ | H | Cl | CH₃ |
| A-1518 | CH₃ | CH₃ | H | Cl | CH₃ |
| A-1519 | CF₃ | CH₃ | H | Cl | CH₃ |
| A-1520 | OCH₃ | CH₃ | H | Cl | CH₃ |
| A-1521 | F | CF₃ | H | Cl | CH₃ |
| A-1522 | Cl | CF₃ | H | Cl | CH₃ |
| A-1523 | CH₃ | CF₃ | H | Cl | CH₃ |
| A-1524 | CF₃ | CF₃ | H | Cl | CH₃ |
| A-1525 | OCH₃ | CF₃ | H | Cl | CH₃ |
| A-1526 | F | H | F | Cl | CH₃ |
| A-1527 | Cl | H | F | Cl | CH₃ |
| A-1528 | CH₃ | H | F | Cl | CH₃ |
| A-1529 | CF₃ | H | F | Cl | CH₃ |
| A-1530 | OCH₃ | H | F | Cl | CH₃ |
| A-1531 | F | F | F | Cl | CH₃ |
| A-1532 | Cl | F | F | Cl | CH₃ |
| A-1533 | CH₃ | F | F | Cl | CH₃ |
| A-1534 | CF₃ | F | F | Cl | CH₃ |
| A-1535 | OCH₃ | F | F | Cl | CH₃ |
| A-1536 | F | Cl | F | Cl | CH₃ |
| A-1537 | Cl | Cl | F | Cl | CH₃ |
| A-1538 | CH₃ | Cl | F | Cl | CH₃ |
| A-1539 | CF₃ | Cl | F | Cl | CH₃ |
| A-1540 | OCH₃ | Cl | F | Cl | CH₃ |
| A-1541 | F | CH₃ | F | Cl | CH₃ |
| A-1542 | Cl | CH₃ | F | Cl | CH₃ |
| A-1543 | CH₃ | CH₃ | F | Cl | CH₃ |
| A-1544 | CF₃ | CH₃ | F | Cl | CH₃ |
| A-1545 | OCH₃ | CH₃ | F | Cl | CH₃ |
| A-1546 | F | CF₃ | F | Cl | CH₃ |
| A-1547 | Cl | CF₃ | F | Cl | CH₃ |
| A-1548 | CH₃ | CF₃ | F | Cl | CH₃ |
| A-1549 | CF₃ | CF₃ | F | Cl | CH₃ |
| A-1550 | OCH₃ | CF₃ | F | Cl | CH₃ |
| A-1551 | F | H | Cl | Cl | CH₃ |
| A-1552 | Cl | H | Cl | Cl | CH₃ |
| A-1553 | CH₃ | H | Cl | Cl | CH₃ |
| A-1554 | CF₃ | H | Cl | Cl | CH₃ |
| A-1555 | OCH₃ | H | Cl | Cl | CH₃ |
| A-1556 | F | F | Cl | Cl | CH₃ |
| A-1557 | Cl | F | Cl | Cl | CH₃ |
| A-1558 | CH₃ | F | Cl | Cl | CH₃ |
| A-1559 | CF₃ | F | Cl | Cl | CH₃ |
| A-1560 | OCH₃ | F | Cl | Cl | CH₃ |
| A-1561 | F | Cl | Cl | Cl | CH₃ |
| A-1562 | Cl | Cl | Cl | Cl | CH₃ |
| A-1563 | CH₃ | Cl | Cl | Cl | CH₃ |
| A-1564 | CF₃ | Cl | Cl | Cl | CH₃ |
| A-1565 | OCH₃ | Cl | Cl | Cl | CH₃ |
| A-1566 | F | CH₃ | Cl | Cl | CH₃ |
| A-1567 | Cl | CH₃ | Cl | Cl | CH₃ |
| A-1568 | CH₃ | CH₃ | Cl | Cl | CH₃ |
| A-1569 | CF₃ | CH₃ | Cl | Cl | CH₃ |
| A-1570 | OCH₃ | CH₃ | Cl | Cl | CH₃ |
| A-1571 | F | CF₃ | Cl | Cl | CH₃ |
| A-1572 | Cl | CF₃ | Cl | Cl | CH₃ |
| A-1573 | CH₃ | CF₃ | Cl | Cl | CH₃ |
| A-1574 | CF₃ | CF₃ | Cl | Cl | CH₃ |
| A-1575 | OCH₃ | CF₃ | Cl | Cl | CH₃ |
| A-1576 | F | H | CH₃ | Cl | CH₃ |
| A-1577 | Cl | H | CH₃ | Cl | CH₃ |
| A-1578 | CH₃ | H | CH₃ | Cl | CH₃ |
| A-1579 | CF₃ | H | CH₃ | Cl | CH₃ |
| A-1580 | OCH₃ | H | CH₃ | Cl | CH₃ |
| A-1581 | F | F | CH₃ | Cl | CH₃ |
| A-1582 | Cl | F | CH₃ | Cl | CH₃ |
| A-1583 | CH₃ | F | CH₃ | Cl | CH₃ |
| A-1584 | CF₃ | F | CH₃ | Cl | CH₃ |
| A-1585 | OCH₃ | F | CH₃ | Cl | CH₃ |
| A-1586 | F | Cl | CH₃ | Cl | CH₃ |
| A-1587 | Cl | Cl | CH₃ | Cl | CH₃ |
| A-1588 | CH₃ | Cl | CH₃ | Cl | CH₃ |
| A-1589 | CF₃ | Cl | CH₃ | Cl | CH₃ |
| A-1590 | OCH₃ | Cl | CH₃ | Cl | CH₃ |
| A-1591 | F | CH₃ | CH₃ | Cl | CH₃ |
| A-1592 | Cl | CH₃ | CH₃ | Cl | CH₃ |
| A-1593 | CH₃ | CH₃ | CH₃ | Cl | CH₃ |
| A-1594 | CF₃ | CH₃ | CH₃ | Cl | CH₃ |
| A-1595 | OCH₃ | CH₃ | CH₃ | Cl | CH₃ |
| A-1596 | F | CF₃ | CH₃ | Cl | CH₃ |
| A-1597 | Cl | CF₃ | CH₃ | Cl | CH₃ |
| A-1598 | CH₃ | CF₃ | CH₃ | Cl | CH₃ |
| A-1599 | CF₃ | CF₃ | CH₃ | Cl | CH₃ |
| A-1600 | OCH₃ | CF₃ | CH₃ | Cl | CH₃ |
| A-1601 | F | H | CF₃ | Cl | CH₃ |
| A-1602 | Cl | H | CF₃ | Cl | CH₃ |
| A-1603 | CH₃ | H | CF₃ | Cl | CH₃ |
| A-1604 | CF₃ | H | CF₃ | Cl | CH₃ |
| A-1605 | OCH₃ | H | CF₃ | Cl | CH₃ |
| A-1606 | F | F | CF₃ | Cl | CH₃ |
| A-1607 | Cl | F | CF₃ | Cl | CH₃ |
| A-1608 | CH₃ | F | CF₃ | Cl | CH₃ |
| A-1609 | CF₃ | F | CF₃ | Cl | CH₃ |
| A-1610 | OCH₃ | F | CF₃ | Cl | CH₃ |
| A-1611 | F | Cl | CF₃ | Cl | CH₃ |
| A-1612 | Cl | Cl | CF₃ | Cl | CH₃ |
| A-1613 | CH₃ | Cl | CF₃ | Cl | CH₃ |
| A-1614 | CF₃ | Cl | CF₃ | Cl | CH₃ |
| A-1615 | OCH₃ | Cl | CF₃ | Cl | CH₃ |
| A-1616 | F | CH₃ | CF₃ | Cl | CH₃ |
| A-1617 | Cl | CH₃ | CF₃ | Cl | CH₃ |
| A-1618 | CH₃ | CH₃ | CF₃ | Cl | CH₃ |
| A-1619 | CF₃ | CH₃ | CF₃ | Cl | CH₃ |
| A-1620 | OCH₃ | CH₃ | CF₃ | Cl | CH₃ |
| A-1621 | F | CF₃ | CF₃ | Cl | CH₃ |
| A-1622 | Cl | CF₃ | CF₃ | Cl | CH₃ |
| A-1623 | CH₃ | CF₃ | CF₃ | Cl | CH₃ |
| A-1624 | CF₃ | CF₃ | CF₃ | Cl | CH₃ |
| A-1625 | OCH₃ | CF₃ | CF₃ | Cl | CH₃ |
| A-1626 | F | H | H | CH₃ | CH₃ |
| A-1627 | Cl | H | H | CH₃ | CH₃ |
| A-1628 | CH₃ | H | H | CH₃ | CH₃ |
| A-1629 | CF₃ | H | H | CH₃ | CH₃ |
| A-1630 | OCH₃ | H | H | CH₃ | CH₃ |
| A-1631 | F | F | H | CH₃ | CH₃ |
| A-1632 | Cl | F | H | CH₃ | CH₃ |
| A-1633 | CH₃ | F | H | CH₃ | CH₃ |
| A-1634 | CF₃ | F | H | CH₃ | CH₃ |
| A-1635 | OCH₃ | F | H | CH₃ | CH₃ |
| A-1636 | F | Cl | H | CH₃ | CH₃ |
| A-1637 | Cl | Cl | H | CH₃ | CH₃ |
| A-1638 | CH₃ | Cl | H | CH₃ | CH₃ |
| A-1639 | CF₃ | Cl | H | CH₃ | CH₃ |
| A-1640 | OCH₃ | Cl | H | CH₃ | CH₃ |
| A-1641 | F | CH₃ | H | CH₃ | CH₃ |
| A-1642 | Cl | CH₃ | H | CH₃ | CH₃ |
| A-1643 | CH₃ | CH₃ | H | CH₃ | CH₃ |
| A-1644 | CF₃ | CH₃ | H | CH₃ | CH₃ |
| A-1645 | OCH₃ | CH₃ | H | CH₃ | CH₃ |
| A-1646 | F | CF₃ | H | CH₃ | CH₃ |
| A-1647 | Cl | CF₃ | H | CH₃ | CH₃ |
| A-1648 | CH₃ | CF₃ | H | CH₃ | CH₃ |

TABLE 1-continued

| | R² | R³ | R⁴ | R⁵ | R⁶ |
|---|---|---|---|---|---|
| A-1649 | CF₃ | CF₃ | H | CH₃ | CH₃ |
| A-1650 | OCH₃ | CF₃ | H | CH₃ | CH₃ |
| A-1651 | F | H | F | CH₃ | CH₃ |
| A-1652 | Cl | H | F | CH₃ | CH₃ |
| A-1653 | CH₃ | H | F | CH₃ | CH₃ |
| A-1654 | CF₃ | H | F | CH₃ | CH₃ |
| A-1655 | OCH₃ | H | F | CH₃ | CH₃ |
| A-1656 | F | F | F | CH₃ | CH₃ |
| A-1657 | Cl | F | F | CH₃ | CH₃ |
| A-1658 | CH₃ | F | F | CH₃ | CH₃ |
| A-1659 | CF₃ | F | F | CH₃ | CH₃ |
| A-1660 | OCH₃ | F | F | CH₃ | CH₃ |
| A-1661 | F | Cl | F | CH₃ | CH₃ |
| A-1662 | Cl | Cl | F | CH₃ | CH₃ |
| A-1663 | CH₃ | Cl | F | CH₃ | CH₃ |
| A-1664 | CF₃ | Cl | F | CH₃ | CH₃ |
| A-1665 | OCH₃ | Cl | F | CH₃ | CH₃ |
| A-1666 | F | CH₃ | F | CH₃ | CH₃ |
| A-1667 | Cl | CH₃ | F | CH₃ | CH₃ |
| A-1668 | CH₃ | CH₃ | F | CH₃ | CH₃ |
| A-1669 | CF₃ | CH₃ | F | CH₃ | CH₃ |
| A-1670 | OCH₃ | CH₃ | F | CH₃ | CH₃ |
| A-1671 | F | CF₃ | F | CH₃ | CH₃ |
| A-1672 | Cl | CF₃ | F | CH₃ | CH₃ |
| A-1673 | CH₃ | CF₃ | F | CH₃ | CH₃ |
| A-1674 | CF₃ | CF₃ | F | CH₃ | CH₃ |
| A-1675 | OCH₃ | CF₃ | F | CH₃ | CH₃ |
| A-1676 | F | H | Cl | CH₃ | CH₃ |
| A-1677 | Cl | H | Cl | CH₃ | CH₃ |
| A-1678 | CH₃ | H | Cl | CH₃ | CH₃ |
| A-1679 | CF₃ | H | Cl | CH₃ | CH₃ |
| A-1680 | OCH₃ | H | Cl | CH₃ | CH₃ |
| A-1681 | F | F | Cl | CH₃ | CH₃ |
| A-1682 | Cl | F | Cl | CH₃ | CH₃ |
| A-1683 | CH₃ | F | Cl | CH₃ | CH₃ |
| A-1684 | CF₃ | F | Cl | CH₃ | CH₃ |
| A-1685 | OCH₃ | F | Cl | CH₃ | CH₃ |
| A-1686 | F | Cl | Cl | CH₃ | CH₃ |
| A-1687 | Cl | Cl | Cl | CH₃ | CH₃ |
| A-1688 | CH₃ | Cl | Cl | CH₃ | CH₃ |
| A-1689 | CF₃ | Cl | Cl | CH₃ | CH₃ |
| A-1690 | OCH₃ | Cl | Cl | CH₃ | CH₃ |
| A-1691 | F | CH₃ | Cl | CH₃ | CH₃ |
| A-1692 | Cl | CH₃ | Cl | CH₃ | CH₃ |
| A-1693 | CH₃ | CH₃ | Cl | CH₃ | CH₃ |
| A-1694 | CF₃ | CH₃ | Cl | CH₃ | CH₃ |
| A-1695 | OCH₃ | CH₃ | Cl | CH₃ | CH₃ |
| A-1696 | F | CF₃ | Cl | CH₃ | CH₃ |
| A-1697 | Cl | CF₃ | Cl | CH₃ | CH₃ |
| A-1698 | CH₃ | CF₃ | Cl | CH₃ | CH₃ |
| A-1699 | CF₃ | CF₃ | Cl | CH₃ | CH₃ |
| A-1700 | OCH₃ | CF₃ | Cl | CH₃ | CH₃ |
| A-1701 | F | H | CH₃ | CH₃ | CH₃ |
| A-1702 | Cl | H | CH₃ | CH₃ | CH₃ |
| A-1703 | CH₃ | H | CH₃ | CH₃ | CH₃ |
| A-1704 | CF₃ | H | CH₃ | CH₃ | CH₃ |
| A-1705 | OCH₃ | H | CH₃ | CH₃ | CH₃ |
| A-1706 | F | F | CH₃ | CH₃ | CH₃ |
| A-1707 | Cl | F | CH₃ | CH₃ | CH₃ |
| A-1708 | CH₃ | F | CH₃ | CH₃ | CH₃ |
| A-1709 | CF₃ | F | CH₃ | CH₃ | CH₃ |
| A-1710 | OCH₃ | F | CH₃ | CH₃ | CH₃ |
| A-1711 | F | Cl | CH₃ | CH₃ | CH₃ |
| A-1712 | Cl | Cl | CH₃ | CH₃ | CH₃ |
| A-1713 | CH₃ | Cl | CH₃ | CH₃ | CH₃ |
| A-1714 | CF₃ | Cl | CH₃ | CH₃ | CH₃ |
| A-1715 | OCH₃ | Cl | CH₃ | CH₃ | CH₃ |
| A-1716 | F | CH₃ | CH₃ | CH₃ | CH₃ |
| A-1717 | Cl | CH₃ | CH₃ | CH₃ | CH₃ |
| A-1718 | CH₃ | CH₃ | CH₃ | CH₃ | CH₃ |
| A-1719 | CF₃ | CH₃ | CH₃ | CH₃ | CH₃ |
| A-1720 | OCH₃ | CH₃ | CH₃ | CH₃ | CH₃ |
| A-1721 | F | CF₃ | CH₃ | CH₃ | CH₃ |
| A-1722 | Cl | CF₃ | CH₃ | CH₃ | CH₃ |
| A-1723 | CH₃ | CF₃ | CH₃ | CH₃ | CH₃ |
| A-1724 | CF₃ | CF₃ | CH₃ | CH₃ | CH₃ |
| A-1725 | OCH₃ | CF₃ | CH₃ | CH₃ | CH₃ |
| A-1726 | F | H | CF₃ | CH₃ | CH₃ |
| A-1727 | Cl | H | CF₃ | CH₃ | CH₃ |
| A-1728 | CH₃ | H | CF₃ | CH₃ | CH₃ |
| A-1729 | CF₃ | H | CF₃ | CH₃ | CH₃ |
| A-1730 | OCH₃ | H | CF₃ | CH₃ | CH₃ |
| A-1731 | F | F | CF₃ | CH₃ | CH₃ |
| A-1732 | Cl | F | CF₃ | CH₃ | CH₃ |
| A-1733 | CH₃ | F | CF₃ | CH₃ | CH₃ |
| A-1734 | CF₃ | F | CF₃ | CH₃ | CH₃ |
| A-1735 | OCH₃ | F | CF₃ | CH₃ | CH₃ |
| A-1736 | F | Cl | CF₃ | CH₃ | CH₃ |
| A-1737 | Cl | Cl | CF₃ | CH₃ | CH₃ |
| A-1738 | CH₃ | Cl | CF₃ | CH₃ | CH₃ |
| A-1739 | CF₃ | Cl | CF₃ | CH₃ | CH₃ |
| A-1740 | OCH₃ | Cl | CF₃ | CH₃ | CH₃ |
| A-1741 | F | CH₃ | CF₃ | CH₃ | CH₃ |
| A-1742 | Cl | CH₃ | CF₃ | CH₃ | CH₃ |
| A-1743 | CH₃ | CH₃ | CF₃ | CH₃ | CH₃ |
| A-1744 | CF₃ | CH₃ | CF₃ | CH₃ | CH₃ |
| A-1745 | OCH₃ | CH₃ | CF₃ | CH₃ | CH₃ |
| A-1746 | F | CF₃ | CF₃ | CH₃ | CH₃ |
| A-1747 | Cl | CF₃ | CF₃ | CH₃ | CH₃ |
| A-1748 | CH₃ | CF₃ | CF₃ | CH₃ | CH₃ |
| A-1749 | CF₃ | CF₃ | CF₃ | CH₃ | CH₃ |
| A-1750 | OCH₃ | CF₃ | CF₃ | CH₃ | CH₃ |
| A-1751 | F | H | H | CF₃ | CH₃ |
| A-1752 | Cl | H | H | CF₃ | CH₃ |
| A-1753 | CH₃ | H | H | CF₃ | CH₃ |
| A-1754 | CF₃ | H | H | CF₃ | CH₃ |
| A-1755 | OCH₃ | H | H | CF₃ | CH₃ |
| A-1756 | F | F | H | CF₃ | CH₃ |
| A-1757 | Cl | F | H | CF₃ | CH₃ |
| A-1758 | CH₃ | F | H | CF₃ | CH₃ |
| A-1759 | CF₃ | F | H | CF₃ | CH₃ |
| A-1760 | OCH₃ | F | H | CF₃ | CH₃ |
| A-1761 | F | Cl | H | CF₃ | CH₃ |
| A-1762 | Cl | Cl | H | CF₃ | CH₃ |
| A-1763 | CH₃ | Cl | H | CF₃ | CH₃ |
| A-1764 | CF₃ | Cl | H | CF₃ | CH₃ |
| A-1765 | OCH₃ | Cl | H | CF₃ | CH₃ |
| A-1766 | F | CH₃ | H | CF₃ | CH₃ |
| A-1767 | Cl | CH₃ | H | CF₃ | CH₃ |
| A-1768 | CH₃ | CH₃ | H | CF₃ | CH₃ |
| A-1769 | CF₃ | CH₃ | H | CF₃ | CH₃ |
| A-1770 | OCH₃ | CH₃ | H | CF₃ | CH₃ |
| A-1771 | F | CF₃ | H | CF₃ | CH₃ |
| A-1772 | Cl | CF₃ | H | CF₃ | CH₃ |
| A-1773 | CH₃ | CF₃ | H | CF₃ | CH₃ |
| A-1774 | CF₃ | CF₃ | H | CF₃ | CH₃ |
| A-1775 | OCH₃ | CF₃ | H | CF₃ | CH₃ |
| A-1776 | F | H | F | CF₃ | CH₃ |
| A-1777 | Cl | H | F | CF₃ | CH₃ |
| A-1778 | CH₃ | H | F | CF₃ | CH₃ |
| A-1779 | CF₃ | H | F | CF₃ | CH₃ |
| A-1780 | OCH₃ | H | F | CF₃ | CH₃ |
| A-1781 | F | F | F | CF₃ | CH₃ |
| A-1782 | Cl | F | F | CF₃ | CH₃ |
| A-1783 | CH₃ | F | F | CF₃ | CH₃ |
| A-1784 | CF₃ | F | F | CF₃ | CH₃ |
| A-1785 | OCH₃ | F | F | CF₃ | CH₃ |
| A-1786 | F | Cl | F | CF₃ | CH₃ |
| A-1787 | Cl | Cl | F | CF₃ | CH₃ |
| A-1788 | CH₃ | Cl | F | CF₃ | CH₃ |
| A-1789 | CF₃ | Cl | F | CF₃ | CH₃ |
| A-1790 | OCH₃ | Cl | F | CF₃ | CH₃ |
| A-1791 | F | CH₃ | F | CF₃ | CH₃ |
| A-1792 | Cl | CH₃ | F | CF₃ | CH₃ |
| A-1793 | CH₃ | CH₃ | F | CF₃ | CH₃ |
| A-1794 | CF₃ | CH₃ | F | CF₃ | CH₃ |
| A-1795 | OCH₃ | CH₃ | F | CF₃ | CH₃ |
| A-1796 | F | CF₃ | F | CF₃ | CH₃ |
| A-1797 | Cl | CF₃ | F | CF₃ | CH₃ |
| A-1798 | CH₃ | CF₃ | F | CF₃ | CH₃ |
| A-1799 | CF₃ | CF₃ | F | CF₃ | CH₃ |
| A-1800 | OCH₃ | CF₃ | F | CF₃ | CH₃ |
| A-1801 | F | H | Cl | CF₃ | CH₃ |
| A-1802 | Cl | H | Cl | CF₃ | CH₃ |
| A-1803 | CH₃ | H | Cl | CF₃ | CH₃ |
| A-1804 | CF₃ | H | Cl | CF₃ | CH₃ |

TABLE 1-continued

|  | R² | R³ | R⁴ | R⁵ | R⁶ |
|---|---|---|---|---|---|
| A-1805 | OCH₃ | H | Cl | CF₃ | CH₃ |
| A-1806 | F | F | Cl | CF₃ | CH₃ |
| A-1807 | Cl | F | Cl | CF₃ | CH₃ |
| A-1808 | CH₃ | F | Cl | CF₃ | CH₃ |
| A-1809 | CF₃ | F | Cl | CF₃ | CH₃ |
| A-1810 | OCH₃ | F | Cl | CF₃ | CH₃ |
| A-1811 | F | Cl | Cl | CF₃ | CH₃ |
| A-1812 | Cl | Cl | Cl | CF₃ | CH₃ |
| A-1813 | CH₃ | Cl | Cl | CF₃ | CH₃ |
| A-1814 | CF₃ | Cl | Cl | CF₃ | CH₃ |
| A-1815 | OCH₃ | Cl | Cl | CF₃ | CH₃ |
| A-1816 | F | CH₃ | Cl | CF₃ | CH₃ |
| A-1817 | Cl | CH₃ | Cl | CF₃ | CH₃ |
| A-1818 | CH₃ | CH₃ | Cl | CF₃ | CH₃ |
| A-1819 | CF₃ | CH₃ | Cl | CF₃ | CH₃ |
| A-1820 | OCH₃ | CH₃ | Cl | CF₃ | CH₃ |
| A-1821 | F | CF₃ | Cl | CF₃ | CH₃ |
| A-1822 | Cl | CF₃ | Cl | CF₃ | CH₃ |
| A-1823 | CH₃ | CF₃ | Cl | CF₃ | CH₃ |
| A-1824 | CF₃ | CF₃ | Cl | CF₃ | CH₃ |
| A-1825 | OCH₃ | CF₃ | Cl | CF₃ | CH₃ |
| A-1826 | F | H | CH₃ | CF₃ | CH₃ |
| A-1827 | Cl | H | CH₃ | CF₃ | CH₃ |
| A-1828 | CH₃ | H | CH₃ | CF₃ | CH₃ |
| A-1829 | CF₃ | H | CH₃ | CF₃ | CH₃ |
| A-1830 | OCH₃ | H | CH₃ | CF₃ | CH₃ |
| A-1831 | F | F | CH₃ | CF₃ | CH₃ |
| A-1832 | Cl | F | CH₃ | CF₃ | CH₃ |
| A-1833 | CH₃ | F | CH₃ | CF₃ | CH₃ |
| A-1834 | CF₃ | F | CH₃ | CF₃ | CH₃ |
| A-1835 | OCH₃ | F | CH₃ | CF₃ | CH₃ |
| A-1836 | F | Cl | CH₃ | CF₃ | CH₃ |
| A-1837 | Cl | Cl | CH₃ | CF₃ | CH₃ |
| A-1838 | CH₃ | Cl | CH₃ | CF₃ | CH₃ |
| A-1839 | CF₃ | Cl | CH₃ | CF₃ | CH₃ |
| A-1840 | OCH₃ | Cl | CH₃ | CF₃ | CH₃ |
| A-1841 | F | CH₃ | CH₃ | CF₃ | CH₃ |
| A-1842 | Cl | CH₃ | CH₃ | CF₃ | CH₃ |
| A-1843 | CH₃ | CH₃ | CH₃ | CF₃ | CH₃ |
| A-1844 | CF₃ | CH₃ | CH₃ | CF₃ | CH₃ |
| A-1845 | OCH₃ | CH₃ | CH₃ | CF₃ | CH₃ |
| A-1846 | F | CF₃ | CH₃ | CF₃ | CH₃ |
| A-1847 | Cl | CF₃ | CH₃ | CF₃ | CH₃ |
| A-1848 | CH₃ | CF₃ | CH₃ | CF₃ | CH₃ |
| A-1849 | CF₃ | CF₃ | CH₃ | CF₃ | CH₃ |
| A-1850 | OCH₃ | CF₃ | CH₃ | CF₃ | CH₃ |
| A-1851 | F | H | CF₃ | CF₃ | CH₃ |
| A-1852 | Cl | H | CF₃ | CF₃ | CH₃ |
| A-1853 | CH₃ | H | CF₃ | CF₃ | CH₃ |
| A-1854 | CF₃ | H | CF₃ | CF₃ | CH₃ |
| A-1855 | OCH₃ | H | CF₃ | CF₃ | CH₃ |
| A-1856 | F | F | CF₃ | CF₃ | CH₃ |
| A-1857 | Cl | F | CF₃ | CF₃ | CH₃ |
| A-1858 | CH₃ | F | CF₃ | CF₃ | CH₃ |
| A-1859 | CF₃ | F | CF₃ | CF₃ | CH₃ |
| A-1860 | OCH₃ | F | CF₃ | CF₃ | CH₃ |
| A-1861 | F | Cl | CF₃ | CF₃ | CH₃ |
| A-1862 | Cl | Cl | CF₃ | CF₃ | CH₃ |
| A-1863 | CH₃ | Cl | CF₃ | CF₃ | CH₃ |
| A-1864 | CF₃ | Cl | CF₃ | CF₃ | CH₃ |
| A-1865 | OCH₃ | Cl | CF₃ | CF₃ | CH₃ |
| A-1866 | F | CH₃ | CF₃ | CF₃ | CH₃ |
| A-1867 | Cl | CH₃ | CF₃ | CF₃ | CH₃ |
| A-1868 | CH₃ | CH₃ | CF₃ | CF₃ | CH₃ |
| A-1869 | CF₃ | CH₃ | CF₃ | CF₃ | CH₃ |
| A-1870 | OCH₃ | CH₃ | CF₃ | CF₃ | CH₃ |
| A-1871 | F | CF₃ | CF₃ | CF₃ | CH₃ |
| A-1872 | Cl | CF₃ | CF₃ | CF₃ | CH₃ |
| A-1873 | CH₃ | CF₃ | CF₃ | CF₃ | CH₃ |
| A-1874 | CF₃ | CF₃ | CF₃ | CF₃ | CH₃ |
| A-1875 | OCH₃ | CF₃ | CF₃ | CF₃ | CH₃ |
| A-1876 | F | H | H | H | CF₃ |
| A-1877 | Cl | H | H | H | CF₃ |
| A-1878 | CH₃ | H | H | H | CF₃ |
| A-1879 | CF₃ | H | H | H | CF₃ |
| A-1880 | OCH₃ | H | H | H | CF₃ |
| A-1881 | F | F | H | H | CF₃ |
| A-1882 | Cl | F | H | H | CF₃ |
| A-1883 | CH₃ | F | H | H | CF₃ |
| A-1884 | CF₃ | F | H | H | CF₃ |
| A-1885 | OCH₃ | F | H | H | CF₃ |
| A-1886 | F | Cl | H | H | CF₃ |
| A-1887 | Cl | Cl | H | H | CF₃ |
| A-1888 | CH₃ | Cl | H | H | CF₃ |
| A-1889 | CF₃ | Cl | H | H | CF₃ |
| A-1890 | OCH₃ | Cl | H | H | CF₃ |
| A-1891 | F | CH₃ | H | H | CF₃ |
| A-1892 | Cl | CH₃ | H | H | CF₃ |
| A-1893 | CH₃ | CH₃ | H | H | CF₃ |
| A-1894 | CF₃ | CH₃ | H | H | CF₃ |
| A-1895 | OCH₃ | CH₃ | H | H | CF₃ |
| A-1896 | F | CF₃ | H | H | CF₃ |
| A-1897 | Cl | CF₃ | H | H | CF₃ |
| A-1898 | CH₃ | CF₃ | H | H | CF₃ |
| A-1899 | CF₃ | CF₃ | H | H | CF₃ |
| A-1900 | OCH₃ | CF₃ | H | H | CF₃ |
| A-1901 | F | H | F | H | CF₃ |
| A-1902 | Cl | H | F | H | CF₃ |
| A-1903 | CH₃ | H | F | H | CF₃ |
| A-1904 | CF₃ | H | F | H | CF₃ |
| A-1905 | OCH₃ | H | F | H | CF₃ |
| A-1906 | F | F | F | H | CF₃ |
| A-1907 | Cl | F | F | H | CF₃ |
| A-1908 | CH₃ | F | F | H | CF₃ |
| A-1909 | CF₃ | F | F | H | CF₃ |
| A-1910 | OCH₃ | F | F | H | CF₃ |
| A-1911 | F | Cl | F | H | CF₃ |
| A-1912 | Cl | Cl | F | H | CF₃ |
| A-1913 | CH₃ | Cl | F | H | CF₃ |
| A-1914 | CF₃ | Cl | F | H | CF₃ |
| A-1915 | OCH₃ | Cl | F | H | CF₃ |
| A-1916 | F | CH₃ | F | H | CF₃ |
| A-1917 | Cl | CH₃ | F | H | CF₃ |
| A-1918 | CH₃ | CH₃ | F | H | CF₃ |
| A-1919 | CF₃ | CH₃ | F | H | CF₃ |
| A-1920 | OCH₃ | CH₃ | F | H | CF₃ |
| A-1921 | F | CF₃ | F | H | CF₃ |
| A-1922 | Cl | CF₃ | F | H | CF₃ |
| A-1923 | CH₃ | CF₃ | F | H | CF₃ |
| A-1924 | CF₃ | CF₃ | F | H | CF₃ |
| A-1925 | OCH₃ | CF₃ | F | H | CF₃ |
| A-1926 | F | H | Cl | H | CF₃ |
| A-1927 | Cl | H | Cl | H | CF₃ |
| A-1928 | CH₃ | H | Cl | H | CF₃ |
| A-1929 | CF₃ | H | Cl | H | CF₃ |
| A-1930 | OCH₃ | H | Cl | H | CF₃ |
| A-1931 | F | F | Cl | H | CF₃ |
| A-1932 | Cl | F | Cl | H | CF₃ |
| A-1933 | CH₃ | F | Cl | H | CF₃ |
| A-1934 | CF₃ | F | Cl | H | CF₃ |
| A-1935 | OCH₃ | F | Cl | H | CF₃ |
| A-1936 | F | Cl | Cl | H | CF₃ |
| A-1937 | Cl | Cl | Cl | H | CF₃ |
| A-1938 | CH₃ | Cl | Cl | H | CF₃ |
| A-1939 | CF₃ | Cl | Cl | H | CF₃ |
| A-1940 | OCH₃ | Cl | Cl | H | CF₃ |
| A-1941 | F | CH₃ | Cl | H | CF₃ |
| A-1942 | Cl | CH₃ | Cl | H | CF₃ |
| A-1943 | CH₃ | CH₃ | Cl | H | CF₃ |
| A-1944 | CF₃ | CH₃ | Cl | H | CF₃ |
| A-1945 | OCH₃ | CH₃ | Cl | H | CF₃ |
| A-1946 | F | CF₃ | Cl | H | CF₃ |
| A-1947 | Cl | CF₃ | Cl | H | CF₃ |
| A-1948 | CH₃ | CF₃ | Cl | H | CF₃ |
| A-1949 | CF₃ | CF₃ | Cl | H | CF₃ |
| A-1950 | OCH₃ | CF₃ | Cl | H | CF₃ |
| A-1951 | F | H | CH₃ | H | CF₃ |
| A-1952 | Cl | H | CH₃ | H | CF₃ |
| A-1953 | CH₃ | H | CH₃ | H | CF₃ |
| A-1954 | CF₃ | H | CH₃ | H | CF₃ |
| A-1955 | OCH₃ | H | CH₃ | H | CF₃ |
| A-1956 | F | F | CH₃ | H | CF₃ |
| A-1957 | Cl | F | CH₃ | H | CF₃ |
| A-1958 | CH₃ | F | CH₃ | H | CF₃ |
| A-1959 | CF₃ | F | CH₃ | H | CF₃ |
| A-1960 | OCH₃ | F | CH₃ | H | CF₃ |

TABLE 1-continued

| | R² | R³ | R⁴ | R⁵ | R⁶ |
|---|---|---|---|---|---|
| A-1961 | F | Cl | CH₃ | H | CF₃ |
| A-1962 | Cl | Cl | CH₃ | H | CF₃ |
| A-1963 | CH₃ | Cl | CH₃ | H | CF₃ |
| A-1964 | CF₃ | Cl | CH₃ | H | CF₃ |
| A-1965 | OCH₃ | Cl | CH₃ | H | CF₃ |
| A-1966 | F | CH₃ | CH₃ | H | CF₃ |
| A-1967 | Cl | CH₃ | CH₃ | H | CF₃ |
| A-1968 | CH₃ | CH₃ | CH₃ | H | CF₃ |
| A-1969 | CF₃ | CH₃ | CH₃ | H | CF₃ |
| A-1970 | OCH₃ | CH₃ | CH₃ | H | CF₃ |
| A-1971 | F | CF₃ | CH₃ | H | CF₃ |
| A-1972 | Cl | CF₃ | CH₃ | H | CF₃ |
| A-1973 | CH₃ | CF₃ | CH₃ | H | CF₃ |
| A-1974 | CF₃ | CF₃ | CH₃ | H | CF₃ |
| A-1975 | OCH₃ | CF₃ | CH₃ | H | CF₃ |
| A-1976 | F | H | CF₃ | H | CF₃ |
| A-1977 | Cl | H | CF₃ | H | CF₃ |
| A-1978 | CH₃ | H | CF₃ | H | CF₃ |
| A-1979 | CF₃ | H | CF₃ | H | CF₃ |
| A-1980 | OCH₃ | H | CF₃ | H | CF₃ |
| A-1981 | F | F | CF₃ | H | CF₃ |
| A-1982 | Cl | F | CF₃ | H | CF₃ |
| A-1983 | CH₃ | F | CF₃ | H | CF₃ |
| A-1984 | CF₃ | F | CF₃ | H | CF₃ |
| A-1985 | OCH₃ | F | CF₃ | H | CF₃ |
| A-1986 | F | Cl | CF₃ | H | CF₃ |
| A-1987 | Cl | Cl | CF₃ | H | CF₃ |
| A-1988 | CH₃ | Cl | CF₃ | H | CF₃ |
| A-1989 | CF₃ | Cl | CF₃ | H | CF₃ |
| A-1990 | OCH₃ | Cl | CF₃ | H | CF₃ |
| A-1991 | F | CH₃ | CF₃ | H | CF₃ |
| A-1992 | Cl | CH₃ | CF₃ | H | CF₃ |
| A-1993 | CH₃ | CH₃ | CF₃ | H | CF₃ |
| A-1994 | CF₃ | CH₃ | CF₃ | H | CF₃ |
| A-1995 | OCH₃ | CH₃ | CF₃ | H | CF₃ |
| A-1996 | F | CF₃ | CF₃ | H | CF₃ |
| A-1997 | Cl | CF₃ | CF₃ | H | CF₃ |
| A-1998 | CH₃ | CF₃ | CF₃ | H | CF₃ |
| A-1999 | CF₃ | CF₃ | CF₃ | H | CF₃ |
| A-2000 | OCH₃ | CF₃ | CF₃ | H | CF₃ |
| A-2001 | F | H | H | F | CF₃ |
| A-2002 | Cl | H | H | F | CF₃ |
| A-2003 | CH₃ | H | H | F | CF₃ |
| A-2004 | CF₃ | H | H | F | CF₃ |
| A-2005 | OCH₃ | H | H | F | CF₃ |
| A-2006 | F | F | H | F | CF₃ |
| A-2007 | Cl | F | H | F | CF₃ |
| A-2008 | CH₃ | F | H | F | CF₃ |
| A-2009 | CF₃ | F | H | F | CF₃ |
| A-2010 | OCH₃ | F | H | F | CF₃ |
| A-2011 | F | Cl | H | F | CF₃ |
| A-2012 | Cl | Cl | H | F | CF₃ |
| A-2013 | CH₃ | Cl | H | F | CF₃ |
| A-2014 | CF₃ | Cl | H | F | CF₃ |
| A-2015 | OCH₃ | Cl | H | F | CF₃ |
| A-2016 | F | CH₃ | H | F | CF₃ |
| A-2017 | Cl | CH₃ | H | F | CF₃ |
| A-2018 | CH₃ | CH₃ | H | F | CF₃ |
| A-2019 | CF₃ | CH₃ | H | F | CF₃ |
| A-2020 | OCH₃ | CH₃ | H | F | CF₃ |
| A-2021 | F | CF₃ | H | F | CF₃ |
| A-2022 | Cl | CF₃ | H | F | CF₃ |
| A-2023 | CH₃ | CF₃ | H | F | CF₃ |
| A-2024 | CF₃ | CF₃ | H | F | CF₃ |
| A-2025 | OCH₃ | CF₃ | H | F | CF₃ |
| A-2026 | F | H | F | F | CF₃ |
| A-2027 | Cl | H | F | F | CF₃ |
| A-2028 | CH₃ | H | F | F | CF₃ |
| A-2029 | CF₃ | H | F | F | CF₃ |
| A-2030 | OCH₃ | H | F | F | CF₃ |
| A-2031 | F | F | F | F | CF₃ |
| A-2032 | Cl | F | F | F | CF₃ |
| A-2033 | CH₃ | F | F | F | CF₃ |
| A-2034 | CF₃ | F | F | F | CF₃ |
| A-2035 | OCH₃ | F | F | F | CF₃ |
| A-2036 | F | Cl | F | F | CF₃ |
| A-2037 | Cl | Cl | F | F | CF₃ |
| A-2038 | CH₃ | Cl | F | F | CF₃ |
| A-2039 | CF₃ | Cl | F | F | CF₃ |
| A-2040 | OCH₃ | Cl | F | F | CF₃ |
| A-2041 | F | CH₃ | F | F | CF₃ |
| A-2042 | Cl | CH₃ | F | F | CF₃ |
| A-2043 | CH₃ | CH₃ | F | F | CF₃ |
| A-2044 | CF₃ | CH₃ | F | F | CF₃ |
| A-2045 | OCH₃ | CH₃ | F | F | CF₃ |
| A-2046 | F | CF₃ | F | F | CF₃ |
| A-2047 | Cl | CF₃ | F | F | CF₃ |
| A-2048 | CH₃ | CF₃ | F | F | CF₃ |
| A-2049 | CF₃ | CF₃ | F | F | CF₃ |
| A-2050 | OCH₃ | CF₃ | F | F | CF₃ |
| A-2051 | F | H | Cl | F | CF₃ |
| A-2052 | Cl | H | Cl | F | CF₃ |
| A-2053 | CH₃ | H | Cl | F | CF₃ |
| A-2054 | CF₃ | H | Cl | F | CF₃ |
| A-2055 | OCH₃ | H | Cl | F | CF₃ |
| A-2056 | F | F | Cl | F | CF₃ |
| A-2057 | Cl | F | Cl | F | CF₃ |
| A-2058 | CH₃ | F | Cl | F | CF₃ |
| A-2059 | CF₃ | F | Cl | F | CF₃ |
| A-2060 | OCH₃ | F | Cl | F | CF₃ |
| A-2061 | F | Cl | Cl | F | CF₃ |
| A-2062 | Cl | Cl | Cl | F | CF₃ |
| A-2063 | CH₃ | Cl | Cl | F | CF₃ |
| A-2064 | CF₃ | Cl | Cl | F | CF₃ |
| A-2065 | OCH₃ | Cl | Cl | F | CF₃ |
| A-2066 | F | CH₃ | Cl | F | CF₃ |
| A-2067 | Cl | CH₃ | Cl | F | CF₃ |
| A-2068 | CH₃ | CH₃ | Cl | F | CF₃ |
| A-2069 | CF₃ | CH₃ | Cl | F | CF₃ |
| A-2070 | OCH₃ | CH₃ | Cl | F | CF₃ |
| A-2071 | F | CF₃ | Cl | F | CF₃ |
| A-2072 | Cl | CF₃ | Cl | F | CF₃ |
| A-2073 | CH₃ | CF₃ | Cl | F | CF₃ |
| A-2074 | CF₃ | CF₃ | Cl | F | CF₃ |
| A-2075 | OCH₃ | CF₃ | Cl | F | CF₃ |
| A-2076 | F | H | CH₃ | F | CF₃ |
| A-2077 | Cl | H | CH₃ | F | CF₃ |
| A-2078 | CH₃ | H | CH₃ | F | CF₃ |
| A-2079 | CF₃ | H | CH₃ | F | CF₃ |
| A-2080 | OCH₃ | H | CH₃ | F | CF₃ |
| A-2081 | F | F | CH₃ | F | CF₃ |
| A-2082 | Cl | F | CH₃ | F | CF₃ |
| A-2083 | CH₃ | F | CH₃ | F | CF₃ |
| A-2084 | CF₃ | F | CH₃ | F | CF₃ |
| A-2085 | OCH₃ | F | CH₃ | F | CF₃ |
| A-2086 | F | Cl | CH₃ | F | CF₃ |
| A-2087 | Cl | Cl | CH₃ | F | CF₃ |
| A-2088 | CH₃ | Cl | CH₃ | F | CF₃ |
| A-2089 | CF₃ | Cl | CH₃ | F | CF₃ |
| A-2090 | OCH₃ | Cl | CH₃ | F | CF₃ |
| A-2091 | F | CH₃ | CH₃ | F | CF₃ |
| A-2092 | Cl | CH₃ | CH₃ | F | CF₃ |
| A-2093 | CH₃ | CH₃ | CH₃ | F | CF₃ |
| A-2094 | CF₃ | CH₃ | CH₃ | F | CF₃ |
| A-2095 | OCH₃ | CH₃ | CH₃ | F | CF₃ |
| A-2096 | F | CF₃ | CH₃ | F | CF₃ |
| A-2097 | Cl | CF₃ | CH₃ | F | CF₃ |
| A-2098 | CH₃ | CF₃ | CH₃ | F | CF₃ |
| A-2099 | CF₃ | CF₃ | CH₃ | F | CF₃ |
| A-2100 | OCH₃ | CF₃ | CH₃ | F | CF₃ |
| A-2101 | F | H | CF₃ | F | CF₃ |
| A-2102 | Cl | H | CF₃ | F | CF₃ |
| A-2103 | CH₃ | H | CF₃ | F | CF₃ |
| A-2104 | CF₃ | H | CF₃ | F | CF₃ |
| A-2105 | OCH₃ | H | CF₃ | F | CF₃ |
| A-2106 | F | F | CF₃ | F | CF₃ |
| A-2107 | Cl | F | CF₃ | F | CF₃ |
| A-2108 | CH₃ | F | CF₃ | F | CF₃ |
| A-2109 | CF₃ | F | CF₃ | F | CF₃ |
| A-2110 | OCH₃ | F | CF₃ | F | CF₃ |
| A-2111 | F | Cl | CF₃ | F | CF₃ |
| A-2112 | Cl | Cl | CF₃ | F | CF₃ |
| A-2113 | CH₃ | Cl | CF₃ | F | CF₃ |
| A-2114 | CF₃ | Cl | CF₃ | F | CF₃ |
| A-2115 | OCH₃ | Cl | CF₃ | F | CF₃ |
| A-2116 | F | CH₃ | CF₃ | F | CF₃ |

TABLE 1-continued

|  | R² | R³ | R⁴ | R⁵ | R⁶ |
|---|---|---|---|---|---|
| A-2117 | Cl | CH₃ | CF₃ | F | CF₃ |
| A-2118 | CH₃ | CH₃ | CF₃ | F | CF₃ |
| A-2119 | CF₃ | CH₃ | CF₃ | F | CF₃ |
| A-2120 | OCH₃ | CH₃ | CF₃ | F | CF₃ |
| A-2121 | F | CF₃ | CF₃ | F | CF₃ |
| A-2122 | Cl | CF₃ | CF₃ | F | CF₃ |
| A-2123 | CH₃ | CF₃ | CF₃ | F | CF₃ |
| A-2124 | CF₃ | CF₃ | CF₃ | F | CF₃ |
| A-2125 | OCH₃ | CF₃ | CF₃ | F | CF₃ |
| A-2126 | F | H | H | Cl | CF₃ |
| A-2127 | Cl | H | H | Cl | CF₃ |
| A-2128 | CH₃ | H | H | Cl | CF₃ |
| A-2129 | CF₃ | H | H | Cl | CF₃ |
| A-2130 | OCH₃ | H | H | Cl | CF₃ |
| A-2131 | F | F | H | Cl | CF₃ |
| A-2132 | Cl | F | H | Cl | CF₃ |
| A-2133 | CH₃ | F | H | Cl | CF₃ |
| A-2134 | CF₃ | F | H | Cl | CF₃ |
| A-2135 | OCH₃ | F | H | Cl | CF₃ |
| A-2136 | F | Cl | H | Cl | CF₃ |
| A-2137 | Cl | Cl | H | Cl | CF₃ |
| A-2138 | CH₃ | Cl | H | Cl | CF₃ |
| A-2139 | CF₃ | Cl | H | Cl | CF₃ |
| A-2140 | OCH₃ | Cl | H | Cl | CF₃ |
| A-2141 | F | CH₃ | H | Cl | CF₃ |
| A-2142 | Cl | CH₃ | H | Cl | CF₃ |
| A-2143 | CH₃ | CH₃ | H | Cl | CF₃ |
| A-2144 | CF₃ | CH₃ | H | Cl | CF₃ |
| A-2145 | OCH₃ | CH₃ | H | Cl | CF₃ |
| A-2146 | F | CF₃ | H | Cl | CF₃ |
| A-2147 | Cl | CF₃ | H | Cl | CF₃ |
| A-2148 | CH₃ | CF₃ | H | Cl | CF₃ |
| A-2149 | CF₃ | CF₃ | H | Cl | CF₃ |
| A-2150 | OCH₃ | CF₃ | H | Cl | CF₃ |
| A-2151 | F | H | F | Cl | CF₃ |
| A-2152 | Cl | H | F | Cl | CF₃ |
| A-2153 | CH₃ | H | F | Cl | CF₃ |
| A-2154 | CF₃ | H | F | Cl | CF₃ |
| A-2155 | OCH₃ | H | F | Cl | CF₃ |
| A-2156 | F | F | F | Cl | CF₃ |
| A-2157 | Cl | F | F | Cl | CF₃ |
| A-2158 | CH₃ | F | F | Cl | CF₃ |
| A-2159 | CF₃ | F | F | Cl | CF₃ |
| A-2160 | OCH₃ | F | F | Cl | CF₃ |
| A-2161 | F | Cl | F | Cl | CF₃ |
| A-2162 | Cl | Cl | F | Cl | CF₃ |
| A-2163 | CH₃ | Cl | F | Cl | CF₃ |
| A-2164 | CF₃ | Cl | F | Cl | CF₃ |
| A-2165 | OCH₃ | Cl | F | Cl | CF₃ |
| A-2166 | F | CH₃ | F | Cl | CF₃ |
| A-2167 | Cl | CH₃ | F | Cl | CF₃ |
| A-2168 | CH₃ | CH₃ | F | Cl | CF₃ |
| A-2169 | CF₃ | CH₃ | F | Cl | CF₃ |
| A-2170 | OCH₃ | CH₃ | F | Cl | CF₃ |
| A-2171 | F | CF₃ | F | Cl | CF₃ |
| A-2172 | Cl | CF₃ | F | Cl | CF₃ |
| A-2173 | CH₃ | CF₃ | F | Cl | CF₃ |
| A-2174 | CF₃ | CF₃ | F | Cl | CF₃ |
| A-2175 | OCH₃ | CF₃ | F | Cl | CF₃ |
| A-2176 | F | H | Cl | Cl | CF₃ |
| A-2177 | Cl | H | Cl | Cl | CF₃ |
| A-2178 | CH₃ | H | Cl | Cl | CF₃ |
| A-2179 | CF₃ | H | Cl | Cl | CF₃ |
| A-2180 | OCH₃ | H | Cl | Cl | CF₃ |
| A-2181 | F | F | Cl | Cl | CF₃ |
| A-2182 | Cl | F | Cl | Cl | CF₃ |
| A-2183 | CH₃ | F | Cl | Cl | CF₃ |
| A-2184 | CF₃ | F | Cl | Cl | CF₃ |
| A-2185 | OCH₃ | F | Cl | Cl | CF₃ |
| A-2186 | F | Cl | Cl | Cl | CF₃ |
| A-2187 | Cl | Cl | Cl | Cl | CF₃ |
| A-2188 | CH₃ | Cl | Cl | Cl | CF₃ |
| A-2189 | CF₃ | Cl | Cl | Cl | CF₃ |
| A-2190 | OCH₃ | Cl | Cl | Cl | CF₃ |
| A-2191 | F | CH₃ | Cl | Cl | CF₃ |
| A-2192 | Cl | CH₃ | Cl | Cl | CF₃ |
| A-2193 | CH₃ | CH₃ | Cl | Cl | CF₃ |
| A-2194 | CF₃ | CH₃ | Cl | Cl | CF₃ |
| A-2195 | OCH₃ | CH₃ | Cl | Cl | CF₃ |
| A-2196 | F | CF₃ | Cl | Cl | CF₃ |
| A-2197 | Cl | CF₃ | Cl | Cl | CF₃ |
| A-2198 | CH₃ | CF₃ | Cl | Cl | CF₃ |
| A-2199 | CF₃ | CF₃ | Cl | Cl | CF₃ |
| A-2200 | OCH₃ | CF₃ | Cl | Cl | CF₃ |
| A-2201 | F | H | CH₃ | Cl | CF₃ |
| A-2202 | Cl | H | CH₃ | Cl | CF₃ |
| A-2203 | CH₃ | H | CH₃ | Cl | CF₃ |
| A-2204 | CF₃ | H | CH₃ | Cl | CF₃ |
| A-2205 | OCH₃ | H | CH₃ | Cl | CF₃ |
| A-2206 | F | F | CH₃ | Cl | CF₃ |
| A-2207 | Cl | F | CH₃ | Cl | CF₃ |
| A-2208 | CH₃ | F | CH₃ | Cl | CF₃ |
| A-2209 | CF₃ | F | CH₃ | Cl | CF₃ |
| A-2210 | OCH₃ | F | CH₃ | Cl | CF₃ |
| A-2211 | F | Cl | CH₃ | Cl | CF₃ |
| A-2212 | Cl | Cl | CH₃ | Cl | CF₃ |
| A-2213 | CH₃ | Cl | CH₃ | Cl | CF₃ |
| A-2214 | CF₃ | Cl | CH₃ | Cl | CF₃ |
| A-2215 | OCH₃ | Cl | CH₃ | Cl | CF₃ |
| A-2216 | F | CH₃ | CH₃ | Cl | CF₃ |
| A-2217 | Cl | CH₃ | CH₃ | Cl | CF₃ |
| A-2218 | CH₃ | CH₃ | CH₃ | Cl | CF₃ |
| A-2219 | CF₃ | CH₃ | CH₃ | Cl | CF₃ |
| A-2220 | OCH₃ | CH₃ | CH₃ | Cl | CF₃ |
| A-2221 | F | CF₃ | CH₃ | Cl | CF₃ |
| A-2222 | Cl | CF₃ | CH₃ | Cl | CF₃ |
| A-2223 | CH₃ | CF₃ | CH₃ | Cl | CF₃ |
| A-2224 | CF₃ | CF₃ | CH₃ | Cl | CF₃ |
| A-2225 | OCH₃ | CF₃ | CH₃ | Cl | CF₃ |
| A-2226 | F | H | CF₃ | Cl | CF₃ |
| A-2227 | Cl | H | CF₃ | Cl | CF₃ |
| A-2228 | CH₃ | H | CF₃ | Cl | CF₃ |
| A-2229 | CF₃ | H | CF₃ | Cl | CF₃ |
| A-2230 | OCH₃ | H | CF₃ | Cl | CF₃ |
| A-2231 | F | F | CF₃ | Cl | CF₃ |
| A-2232 | Cl | F | CF₃ | Cl | CF₃ |
| A-2233 | CH₃ | F | CF₃ | Cl | CF₃ |
| A-2234 | CF₃ | F | CF₃ | Cl | CF₃ |
| A-2235 | OCH₃ | F | CF₃ | Cl | CF₃ |
| A-2236 | F | Cl | CF₃ | Cl | CF₃ |
| A-2237 | Cl | Cl | CF₃ | Cl | CF₃ |
| A-2238 | CH₃ | Cl | CF₃ | Cl | CF₃ |
| A-2239 | CF₃ | Cl | CF₃ | Cl | CF₃ |
| A-2240 | OCH₃ | Cl | CF₃ | Cl | CF₃ |
| A-2241 | F | CH₃ | CF₃ | Cl | CF₃ |
| A-2242 | Cl | CH₃ | CF₃ | Cl | CF₃ |
| A-2243 | CH₃ | CH₃ | CF₃ | Cl | CF₃ |
| A-2244 | CF₃ | CH₃ | CF₃ | Cl | CF₃ |
| A-2245 | OCH₃ | CH₃ | CF₃ | Cl | CF₃ |
| A-2246 | F | CF₃ | CF₃ | Cl | CF₃ |
| A-2247 | Cl | CF₃ | CF₃ | Cl | CF₃ |
| A-2248 | CH₃ | CF₃ | CF₃ | Cl | CF₃ |
| A-2249 | CF₃ | CF₃ | CF₃ | Cl | CF₃ |
| A-2250 | OCH₃ | CF₃ | CF₃ | Cl | CF₃ |
| A-2251 | F | H | H | CH₃ | CF₃ |
| A-2252 | Cl | H | H | CH₃ | CF₃ |
| A-2253 | CH₃ | H | H | CH₃ | CF₃ |
| A-2254 | CF₃ | H | H | CH₃ | CF₃ |
| A-2255 | OCH₃ | H | H | CH₃ | CF₃ |
| A-2256 | F | F | H | CH₃ | CF₃ |
| A-2257 | Cl | F | H | CH₃ | CF₃ |
| A-2258 | CH₃ | F | H | CH₃ | CF₃ |
| A-2259 | CF₃ | F | H | CH₃ | CF₃ |
| A-2260 | OCH₃ | F | H | CH₃ | CF₃ |
| A-2261 | F | Cl | H | CH₃ | CF₃ |
| A-2262 | Cl | Cl | H | CH₃ | CF₃ |
| A-2263 | CH₃ | Cl | H | CH₃ | CF₃ |
| A-2264 | CF₃ | Cl | H | CH₃ | CF₃ |
| A-2265 | OCH₃ | Cl | H | CH₃ | CF₃ |
| A-2266 | F | CH₃ | H | CH₃ | CF₃ |
| A-2267 | Cl | CH₃ | H | CH₃ | CF₃ |
| A-2268 | CH₃ | CH₃ | H | CH₃ | CF₃ |
| A-2269 | CF₃ | CH₃ | H | CH₃ | CF₃ |
| A-2270 | OCH₃ | CH₃ | H | CH₃ | CF₃ |
| A-2271 | F | CF₃ | H | CH₃ | CF₃ |
| A-2272 | Cl | CF₃ | H | CH₃ | CF₃ |

TABLE 1-continued

|  | R² | R³ | R⁴ | R⁵ | R⁶ |
|---|---|---|---|---|---|
| A-2273 | CH₃ | CF₃ | H | CH₃ | CF₃ |
| A-2274 | CF₃ | CF₃ | H | CH₃ | CF₃ |
| A-2275 | OCH₃ | CF₃ | H | CH₃ | CF₃ |
| A-2276 | F | H | F | CH₃ | CF₃ |
| A-2277 | Cl | H | F | CH₃ | CF₃ |
| A-2278 | CH₃ | H | F | CH₃ | CF₃ |
| A-2279 | CF₃ | H | F | CH₃ | CF₃ |
| A-2280 | OCH₃ | H | F | CH₃ | CF₃ |
| A-2281 | F | F | F | CH₃ | CF₃ |
| A-2282 | Cl | F | F | CH₃ | CF₃ |
| A-2283 | CH₃ | F | F | CH₃ | CF₃ |
| A-2284 | CF₃ | F | F | CH₃ | CF₃ |
| A-2285 | OCH₃ | F | F | CH₃ | CF₃ |
| A-2286 | F | Cl | F | CH₃ | CF₃ |
| A-2287 | Cl | Cl | F | CH₃ | CF₃ |
| A-2288 | CH₃ | Cl | F | CH₃ | CF₃ |
| A-2289 | CF₃ | Cl | F | CH₃ | CF₃ |
| A-2290 | OCH₃ | Cl | F | CH₃ | CF₃ |
| A-2291 | F | CH₃ | F | CH₃ | CF₃ |
| A-2292 | Cl | CH₃ | F | CH₃ | CF₃ |
| A-2293 | CH₃ | CH₃ | F | CH₃ | CF₃ |
| A-2294 | CF₃ | CH₃ | F | CH₃ | CF₃ |
| A-2295 | OCH₃ | CH₃ | F | CH₃ | CF₃ |
| A-2296 | F | CF₃ | F | CH₃ | CF₃ |
| A-2297 | Cl | CF₃ | F | CH₃ | CF₃ |
| A-2298 | CH₃ | CF₃ | F | CH₃ | CF₃ |
| A-2299 | CF₃ | CF₃ | F | CH₃ | CF₃ |
| A-2300 | OCH₃ | CF₃ | F | CH₃ | CF₃ |
| A-2301 | F | H | Cl | CH₃ | CF₃ |
| A-2302 | Cl | H | Cl | CH₃ | CF₃ |
| A-2303 | CH₃ | H | Cl | CH₃ | CF₃ |
| A-2304 | CF₃ | H | Cl | CH₃ | CF₃ |
| A-2305 | OCH₃ | H | Cl | CH₃ | CF₃ |
| A-2306 | F | F | Cl | CH₃ | CF₃ |
| A-2307 | Cl | F | Cl | CH₃ | CF₃ |
| A-2308 | CH₃ | F | Cl | CH₃ | CF₃ |
| A-2309 | CF₃ | F | Cl | CH₃ | CF₃ |
| A-2310 | OCH₃ | F | Cl | CH₃ | CF₃ |
| A-2311 | F | Cl | Cl | CH₃ | CF₃ |
| A-2312 | Cl | Cl | Cl | CH₃ | CF₃ |
| A-2313 | CH₃ | Cl | Cl | CH₃ | CF₃ |
| A-2314 | CF₃ | Cl | Cl | CH₃ | CF₃ |
| A-2315 | OCH₃ | Cl | Cl | CH₃ | CF₃ |
| A-2316 | F | CH₃ | Cl | CH₃ | CF₃ |
| A-2317 | Cl | CH₃ | Cl | CH₃ | CF₃ |
| A-2318 | CH₃ | CH₃ | Cl | CH₃ | CF₃ |
| A-2319 | CF₃ | CH₃ | Cl | CH₃ | CF₃ |
| A-2320 | OCH₃ | CH₃ | Cl | CH₃ | CF₃ |
| A-2321 | F | CF₃ | Cl | CH₃ | CF₃ |
| A-2322 | Cl | CF₃ | Cl | CH₃ | CF₃ |
| A-2323 | CH₃ | CF₃ | Cl | CH₃ | CF₃ |
| A-2324 | CF₃ | CF₃ | Cl | CH₃ | CF₃ |
| A-2325 | OCH₃ | CF₃ | Cl | CH₃ | CF₃ |
| A-2326 | F | H | CH₃ | CH₃ | CF₃ |
| A-2327 | Cl | H | CH₃ | CH₃ | CF₃ |
| A-2328 | CH₃ | H | CH₃ | CH₃ | CF₃ |
| A-2329 | CF₃ | H | CH₃ | CH₃ | CF₃ |
| A-2330 | OCH₃ | H | CH₃ | CH₃ | CF₃ |
| A-2331 | F | F | CH₃ | CH₃ | CF₃ |
| A-2332 | Cl | F | CH₃ | CH₃ | CF₃ |
| A-2333 | CH₃ | F | CH₃ | CH₃ | CF₃ |
| A-2334 | CF₃ | F | CH₃ | CH₃ | CF₃ |
| A-2335 | OCH₃ | F | CH₃ | CH₃ | CF₃ |
| A-2336 | F | Cl | CH₃ | CH₃ | CF₃ |
| A-2337 | Cl | Cl | CH₃ | CH₃ | CF₃ |
| A-2338 | CH₃ | Cl | CH₃ | CH₃ | CF₃ |
| A-2339 | CF₃ | Cl | CH₃ | CH₃ | CF₃ |
| A-2340 | OCH₃ | Cl | CH₃ | CH₃ | CF₃ |
| A-2341 | F | CH₃ | CH₃ | CH₃ | CF₃ |
| A-2342 | Cl | CH₃ | CH₃ | CH₃ | CF₃ |
| A-2343 | CH₃ | CH₃ | CH₃ | CH₃ | CF₃ |
| A-2344 | CF₃ | CH₃ | CH₃ | CH₃ | CF₃ |
| A-2345 | OCH₃ | CH₃ | CH₃ | CH₃ | CF₃ |
| A-2346 | F | CF₃ | CH₃ | CH₃ | CF₃ |
| A-2347 | Cl | CF₃ | CH₃ | CH₃ | CF₃ |
| A-2348 | CH₃ | CF₃ | CH₃ | CH₃ | CF₃ |
| A-2349 | CF₃ | CF₃ | CH₃ | CH₃ | CF₃ |
| A-2350 | OCH₃ | CF₃ | CH₃ | CH₃ | CF₃ |
| A-2351 | F | H | CF₃ | CH₃ | CF₃ |
| A-2352 | Cl | H | CF₃ | CH₃ | CF₃ |
| A-2353 | CH₃ | H | CF₃ | CH₃ | CF₃ |
| A-2354 | CF₃ | H | CF₃ | CH₃ | CF₃ |
| A-2355 | OCH₃ | H | CF₃ | CH₃ | CF₃ |
| A-2356 | F | F | CF₃ | CH₃ | CF₃ |
| A-2357 | Cl | F | CF₃ | CH₃ | CF₃ |
| A-2358 | CH₃ | F | CF₃ | CH₃ | CF₃ |
| A-2359 | CF₃ | F | CF₃ | CH₃ | CF₃ |
| A-2360 | OCH₃ | F | CF₃ | CH₃ | CF₃ |
| A-2361 | F | Cl | CF₃ | CH₃ | CF₃ |
| A-2362 | Cl | Cl | CF₃ | CH₃ | CF₃ |
| A-2363 | CH₃ | Cl | CF₃ | CH₃ | CF₃ |
| A-2364 | CF₃ | Cl | CF₃ | CH₃ | CF₃ |
| A-2365 | OCH₃ | Cl | CF₃ | CH₃ | CF₃ |
| A-2366 | F | CH₃ | CF₃ | CH₃ | CF₃ |
| A-2367 | Cl | CH₃ | CF₃ | CH₃ | CF₃ |
| A-2368 | CH₃ | CH₃ | CF₃ | CH₃ | CF₃ |
| A-2369 | CF₃ | CH₃ | CF₃ | CH₃ | CF₃ |
| A-2370 | OCH₃ | CH₃ | CF₃ | CH₃ | CF₃ |
| A-2371 | F | CF₃ | CF₃ | CH₃ | CF₃ |
| A-2372 | Cl | CF₃ | CF₃ | CH₃ | CF₃ |
| A-2373 | CH₃ | CF₃ | CF₃ | CH₃ | CF₃ |
| A-2374 | CF₃ | CF₃ | CF₃ | CH₃ | CF₃ |
| A-2375 | OCH₃ | CF₃ | CF₃ | CH₃ | CF₃ |
| A-2376 | F | H | H | CF₃ | CF₃ |
| A-2377 | Cl | H | H | CF₃ | CF₃ |
| A-2378 | CH₃ | H | H | CF₃ | CF₃ |
| A-2379 | CF₃ | H | H | CF₃ | CF₃ |
| A-2380 | OCH₃ | H | H | CF₃ | CF₃ |
| A-2381 | F | F | H | CF₃ | CF₃ |
| A-2382 | Cl | F | H | CF₃ | CF₃ |
| A-2383 | CH₃ | F | H | CF₃ | CF₃ |
| A-2384 | CF₃ | F | H | CF₃ | CF₃ |
| A-2385 | OCH₃ | F | H | CF₃ | CF₃ |
| A-2386 | F | Cl | H | CF₃ | CF₃ |
| A-2387 | Cl | Cl | H | CF₃ | CF₃ |
| A-2388 | CH₃ | Cl | H | CF₃ | CF₃ |
| A-2389 | CF₃ | Cl | H | CF₃ | CF₃ |
| A-2390 | OCH₃ | Cl | H | CF₃ | CF₃ |
| A-2391 | F | CH₃ | H | CF₃ | CF₃ |
| A-2392 | Cl | CH₃ | H | CF₃ | CF₃ |
| A-2393 | CH₃ | CH₃ | H | CF₃ | CF₃ |
| A-2394 | CF₃ | CH₃ | H | CF₃ | CF₃ |
| A-2395 | OCH₃ | CH₃ | H | CF₃ | CF₃ |
| A-2396 | F | CF₃ | H | CF₃ | CF₃ |
| A-2397 | Cl | CF₃ | H | CF₃ | CF₃ |
| A-2398 | CH₃ | CF₃ | H | CF₃ | CF₃ |
| A-2399 | CF₃ | CF₃ | H | CF₃ | CF₃ |
| A-2400 | OCH₃ | CF₃ | H | CF₃ | CF₃ |
| A-2401 | F | H | F | CF₃ | CF₃ |
| A-2402 | Cl | H | F | CF₃ | CF₃ |
| A-2403 | CH₃ | H | F | CF₃ | CF₃ |
| A-2404 | CF₃ | H | F | CF₃ | CF₃ |
| A-2405 | OCH₃ | H | F | CF₃ | CF₃ |
| A-2406 | F | F | F | CF₃ | CF₃ |
| A-2407 | Cl | F | F | CF₃ | CF₃ |
| A-2408 | CH₃ | F | F | CF₃ | CF₃ |
| A-2409 | CF₃ | F | F | CF₃ | CF₃ |
| A-2410 | OCH₃ | F | F | CF₃ | CF₃ |
| A-2411 | F | Cl | F | CF₃ | CF₃ |
| A-2412 | Cl | Cl | F | CF₃ | CF₃ |
| A-2413 | CH₃ | Cl | F | CF₃ | CF₃ |
| A-2414 | CF₃ | Cl | F | CF₃ | CF₃ |
| A-2415 | OCH₃ | Cl | F | CF₃ | CF₃ |
| A-2416 | F | CH₃ | F | CF₃ | CF₃ |
| A-2417 | Cl | CH₃ | F | CF₃ | CF₃ |
| A-2418 | CH₃ | CH₃ | F | CF₃ | CF₃ |
| A-2419 | CF₃ | CH₃ | F | CF₃ | CF₃ |
| A-2420 | OCH₃ | CH₃ | F | CF₃ | CF₃ |
| A-2421 | F | CF₃ | F | CF₃ | CF₃ |
| A-2422 | Cl | CF₃ | F | CF₃ | CF₃ |
| A-2423 | CH₃ | CF₃ | F | CF₃ | CF₃ |
| A-2424 | CF₃ | CF₃ | F | CF₃ | CF₃ |
| A-2425 | OCH₃ | CF₃ | F | CF₃ | CF₃ |
| A-2426 | F | H | Cl | CF₃ | CF₃ |
| A-2427 | Cl | H | Cl | CF₃ | CF₃ |
| A-2428 | CH₃ | H | Cl | CF₃ | CF₃ |

TABLE 1-continued

| | R² | R³ | R⁴ | R⁵ | R⁶ |
|---|---|---|---|---|---|
| A-2429 | CF₃ | H | Cl | CF₃ | CF₃ |
| A-2430 | OCH₃ | H | Cl | CF₃ | CF₃ |
| A-2431 | F | F | Cl | CF₃ | CF₃ |
| A-2432 | Cl | F | Cl | CF₃ | CF₃ |
| A-2433 | CH₃ | F | Cl | CF₃ | CF₃ |
| A-2434 | CF₃ | F | Cl | CF₃ | CF₃ |
| A-2435 | OCH₃ | F | Cl | CF₃ | CF₃ |
| A-2436 | F | Cl | Cl | CF₃ | CF₃ |
| A-2437 | Cl | Cl | Cl | CF₃ | CF₃ |
| A-2438 | CH₃ | Cl | Cl | CF₃ | CF₃ |
| A-2439 | CF₃ | Cl | Cl | CF₃ | CF₃ |
| A-2440 | OCH₃ | Cl | Cl | CF₃ | CF₃ |
| A-2441 | F | CH₃ | Cl | CF₃ | CF₃ |
| A-2442 | Cl | CH₃ | Cl | CF₃ | CF₃ |
| A-2443 | CH₃ | CH₃ | Cl | CF₃ | CF₃ |
| A-2444 | CF₃ | CH₃ | Cl | CF₃ | CF₃ |
| A-2445 | OCH₃ | CH₃ | Cl | CF₃ | CF₃ |
| A-2446 | F | CF₃ | Cl | CF₃ | CF₃ |
| A-2447 | Cl | CF₃ | Cl | CF₃ | CF₃ |
| A-2448 | CH₃ | CF₃ | Cl | CF₃ | CF₃ |
| A-2449 | CF₃ | CF₃ | Cl | CF₃ | CF₃ |
| A-2450 | OCH₃ | CF₃ | Cl | CF₃ | CF₃ |
| A-2451 | F | H | CH₃ | CF₃ | CF₃ |
| A-2452 | Cl | H | CH₃ | CF₃ | CF₃ |
| A-2453 | CH₃ | H | CH₃ | CF₃ | CF₃ |
| A-2454 | CF₃ | H | CH₃ | CF₃ | CF₃ |
| A-2455 | OCH₃ | H | CH₃ | CF₃ | CF₃ |
| A-2456 | F | F | CH₃ | CF₃ | CF₃ |
| A-2457 | Cl | F | CH₃ | CF₃ | CF₃ |
| A-2458 | CH₃ | F | CH₃ | CF₃ | CF₃ |
| A-2459 | CF₃ | F | CH₃ | CF₃ | CF₃ |
| A-2460 | OCH₃ | F | CH₃ | CF₃ | CF₃ |
| A-2461 | F | Cl | CH₃ | CF₃ | CF₃ |
| A-2462 | Cl | Cl | CH₃ | CF₃ | CF₃ |
| A-2463 | CH₃ | Cl | CH₃ | CF₃ | CF₃ |
| A-2464 | CF₃ | Cl | CH₃ | CF₃ | CF₃ |
| A-2465 | OCH₃ | Cl | CH₃ | CF₃ | CF₃ |
| A-2466 | F | CH₃ | CH₃ | CF₃ | CF₃ |
| A-2467 | Cl | CH₃ | CH₃ | CF₃ | CF₃ |
| A-2468 | CH₃ | CH₃ | CH₃ | CF₃ | CF₃ |
| A-2469 | CF₃ | CH₃ | CH₃ | CF₃ | CF₃ |
| A-2470 | OCH₃ | CH₃ | CH₃ | CF₃ | CF₃ |
| A-2471 | F | CF₃ | CH₃ | CF₃ | CF₃ |
| A-2472 | Cl | CF₃ | CH₃ | CF₃ | CF₃ |
| A-2473 | CH₃ | CF₃ | CH₃ | CF₃ | CF₃ |
| A-2474 | CF₃ | CF₃ | CH₃ | CF₃ | CF₃ |
| A-2475 | OCH₃ | CF₃ | CH₃ | CF₃ | CF₃ |
| A-2476 | F | H | CF₃ | CF₃ | CF₃ |
| A-2477 | Cl | H | CF₃ | CF₃ | CF₃ |
| A-2478 | CH₃ | H | CF₃ | CF₃ | CF₃ |
| A-2479 | CF₃ | H | CF₃ | CF₃ | CF₃ |
| A-2480 | OCH₃ | H | CF₃ | CF₃ | CF₃ |
| A-2481 | F | F | CF₃ | CF₃ | CF₃ |
| A-2482 | Cl | F | CF₃ | CF₃ | CF₃ |
| A-2483 | CH₃ | F | CF₃ | CF₃ | CF₃ |
| A-2484 | CF₃ | F | CF₃ | CF₃ | CF₃ |
| A-2485 | OCH₃ | F | CF₃ | CF₃ | CF₃ |
| A-2486 | F | Cl | CF₃ | CF₃ | CF₃ |
| A-2487 | Cl | Cl | CF₃ | CF₃ | CF₃ |
| A-2488 | CH₃ | Cl | CF₃ | CF₃ | CF₃ |
| A-2489 | CF₃ | Cl | CF₃ | CF₃ | CF₃ |
| A-2490 | OCH₃ | Cl | CF₃ | CF₃ | CF₃ |
| A-2491 | F | CH₃ | CF₃ | CF₃ | CF₃ |
| A-2492 | Cl | CH₃ | CF₃ | CF₃ | CF₃ |
| A-2493 | CH₃ | CH₃ | CF₃ | CF₃ | CF₃ |
| A-2494 | CF₃ | CH₃ | CF₃ | CF₃ | CF₃ |
| A-2495 | OCH₃ | CH₃ | CF₃ | CF₃ | CF₃ |
| A-2496 | F | CF₃ | CF₃ | CF₃ | CF₃ |
| A-2497 | Cl | CF₃ | CF₃ | CF₃ | CF₃ |
| A-2498 | CH₃ | CF₃ | CF₃ | CF₃ | CF₃ |
| A-2499 | CF₃ | CF₃ | CF₃ | CF₃ | CF₃ |
| A-2500 | OCH₃ | CF₃ | CF₃ | CF₃ | CF₃ |

TABLE B

Examples of preferred compounds of formula I'.1 are the compounds of formula I.1-B,

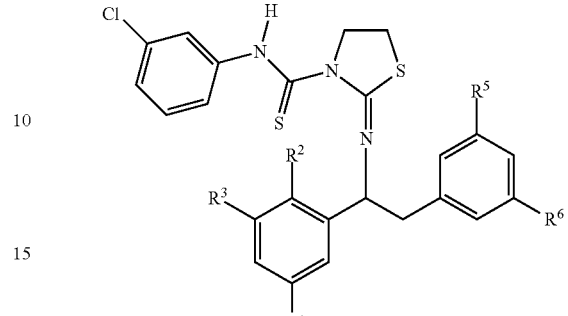

(I'.1-B)

wherein R², R³, R⁴, R⁵ and R⁶ have the meanings corresponding to one line of the table 1 (compounds I'.1-B.1 to I'.1-B.2500).

TABLE C

Examples of preferred compounds of formula I'.1 are the compounds of formula I'.1-C,

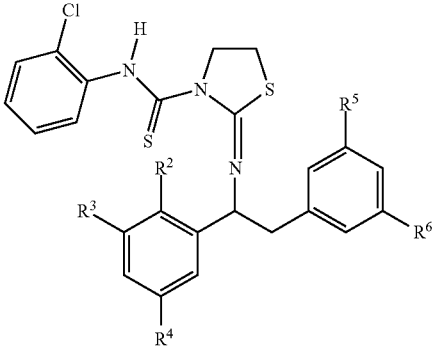

(I'.1-C)

wherein R², R³, R⁴, R⁵ and R⁶ have the meanings corresponding to one line of the table 1 (compounds I'.1-C.1 to I'.1-C.2500).

TABLE D

Examples of preferred compounds of formula I'.1 are the compounds of formula I'.1-D.

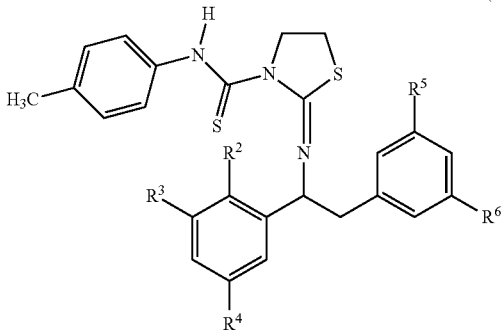

(I'.1-D)

wherein R², R³, R⁴, R⁵ and R⁶ have the meanings corresponding to one line of the table 1 (compounds I'.1-D.1 to I'.1-D.2500).

TABLE E

Examples of preferred compounds of formula I'.1 are the compounds of formula I'.1-E,

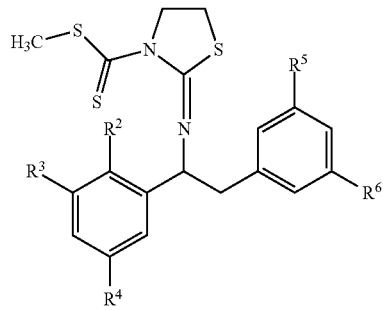

(I'.1-E)

wherein $R^2$, $R^3$, $R^4$, $R^5$ and $R^6$ have the meanings corresponding to one line of the table 1 (compounds I'.1-E.1 to I'.1-E.2500).

TABLE F

Examples of preferred compounds of formula I'.1 are the compounds of formula I'.1-F.

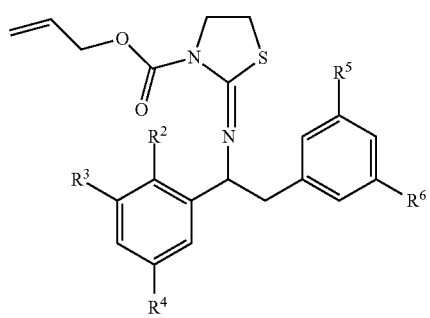

(I'.1-F)

wherein $R^2$, $R^3$, $R^4$, $R^5$ and $R^6$ have the meanings corresponding to one line of the table 1 (compounds I'.1-F.1 to I'.1-F.2500).

TABLE G

Examples of preferred compounds of formula I'.1 are the compounds of formula I'.1-G,

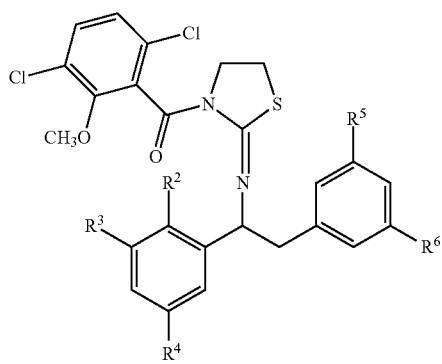

(I'.1-G)

wherein $R^2$, $R^3$, $R^4$, $R^5$ and $R^6$ have the meanings corresponding to one line of the table 1 (compounds I'.1-G.1 to I'.1-G.2500).

TABLE H

Examples of preferred compounds of formula I'.1 are the compounds of formula I'.1-H,

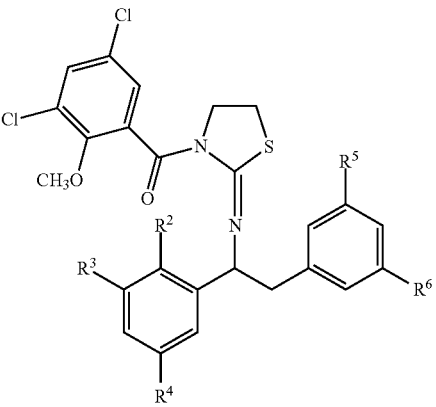

(I'.1-H)

wherein $R^2$, $R^3$, $R^4$, $R^5$ and $R^6$ have the meanings corresponding to one line of the table 1 (compounds I'.1-H.1 to I'.1-H.2500).

TABLE J

Examples of preferred compounds of formula I'.1 are the compounds of formula I'.1-J,

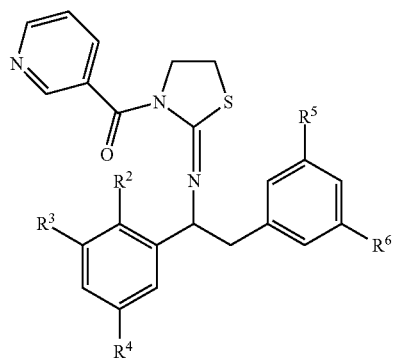

(I'.1-J)

wherein $R^2$, $R^3$, $R^4$, $R^5$ and $R^6$ have the meanings corresponding to one line of the table 1 (compounds I'.1-J.1 to I'.1-J.2500).

TABLE K

Examples of preferred compounds of formula I'.1 are the compounds of formula I'.1-K,

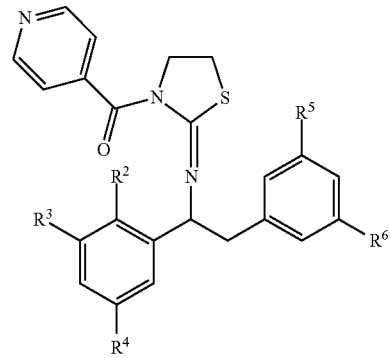

(I'.1-K)

wherein $R^2$, $R^3$, $R^4$, $R^5$ and $R^6$ have the meanings corresponding to one line of the table 1 (compounds I'.1-K.1 to I'.1-K.2500).

TABLE L

Examples of preferred compounds of formula I'.1 are the compounds of formula I'.1-L,

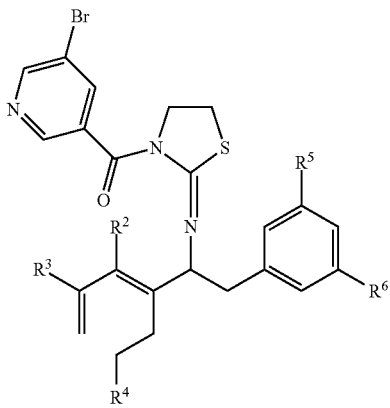

(I'.1-L)

wherein $R^2$, $R^3$, $R^4$, $R^5$ and $R^6$ have the meanings corresponding to one line of the table 1 (compounds I'.1-L.1 to I'.1-L.2500).

TABLE M

Examples of preferred compounds of formula I'.1 are the compounds of formula I'.1-M,

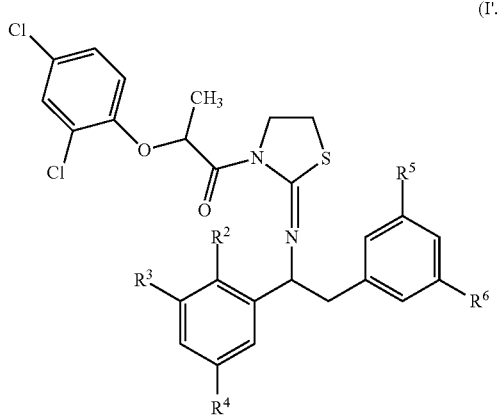

(I'.1-M)

wherein $R^2$, $R^3$, $R^4$, $R^5$ and $R^6$ have the meanings corresponding to one line of the table 1 (compounds I'.1-M.1 to I'.1-M.2500).

TABLE N

Examples of preferred compounds of formula I'.1 are the compounds of formula I'.1-N,

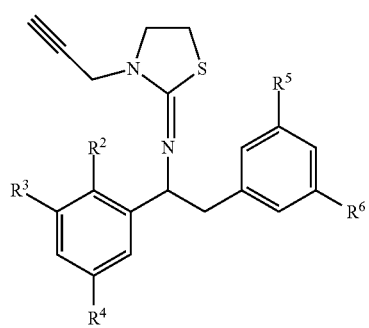

(I'.1-N)

wherein $R^2$, $R^3$, $R^4$, $R^5$ and $R^6$ have the meanings corresponding to one line of the table 1 (compounds I'.1-N.1 to I'.1-N.2500).

TABLE O

Examples of preferred compounds of formula I'.1 are the compounds of formula I'.1-O,

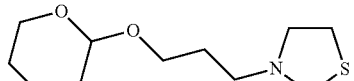
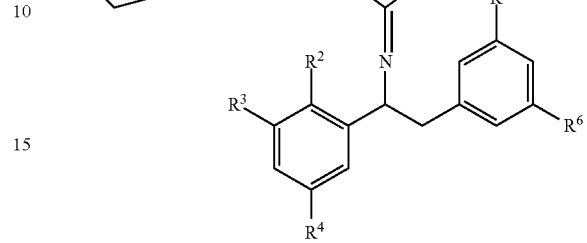

(I'.1-O)

wherein $R^2$, $R^3$, $R^4$, $R^5$ and $R^6$ have the meanings corresponding to one line of the table 1 (compounds I'.1-O.1 to I'.1-O.2500).

TABLE P

Examples of preferred compounds of formula I'.1 are the compounds of formula I'.1-P,

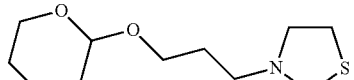
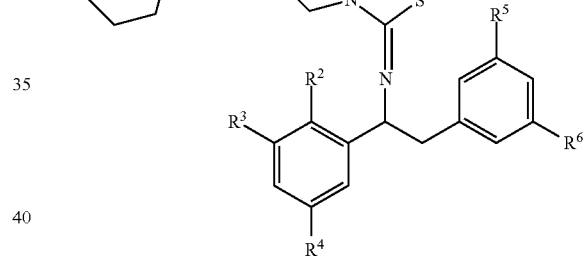

(I'.1-P)

wherein $R^2$, $R^3$, $R^4$, $R^5$ and $R^6$ have the meanings corresponding to one line of the table 1 (compounds I'.1-P.1 to I'.1-P.2500).

TABLE Q

Examples of preferred compounds of formula I'.1 are the compounds of formula I'.1-Q,

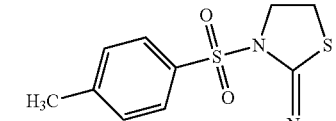
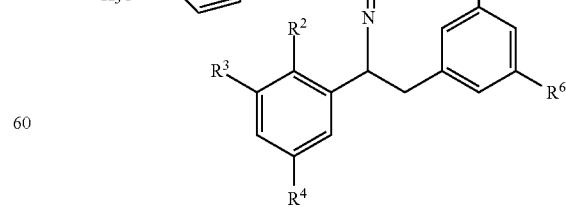

(I'.1-Q)

wherein $R^2$, $R^3$, $R^4$, $R^5$ and $R^6$ have the meanings corresponding to one line of the table 1 (compounds I'.1-Q.1 to I'.1-Q.2500).

Preparation of the compounds of formula I can be accomplished according to the examples given in schemes 1 to 4 but are not limited to the routes given below:

The compounds of formula I.1 and I.2 can for instance be prepared according to the preparation procedures described in WO 2005/63724 as outlined in scheme 1 by reacting a compound of formula II.1 and/or its tautomer II.2 with a compound of formula III e.g. an alkylating agent, an acylating agent or the like. The major product of such a reaction is the compound of formula I.1, often being the only isomer isolated.

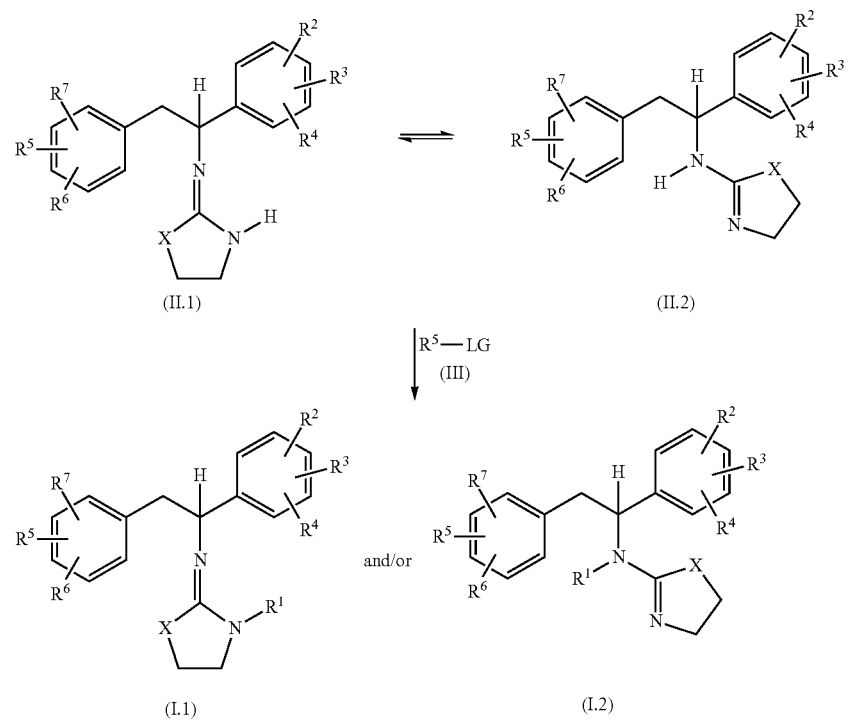

The compounds of formula II.1 and their tautomers of formula II.2. can for instance be prepared from the corresponding diphenylethylamines IV by the synthetic routes outlined in schemes 2 and 3. Compounds of the formula II.1 and their tautomers of formula II.2 with X being S can be obtained according to the method outlined in scheme 2.

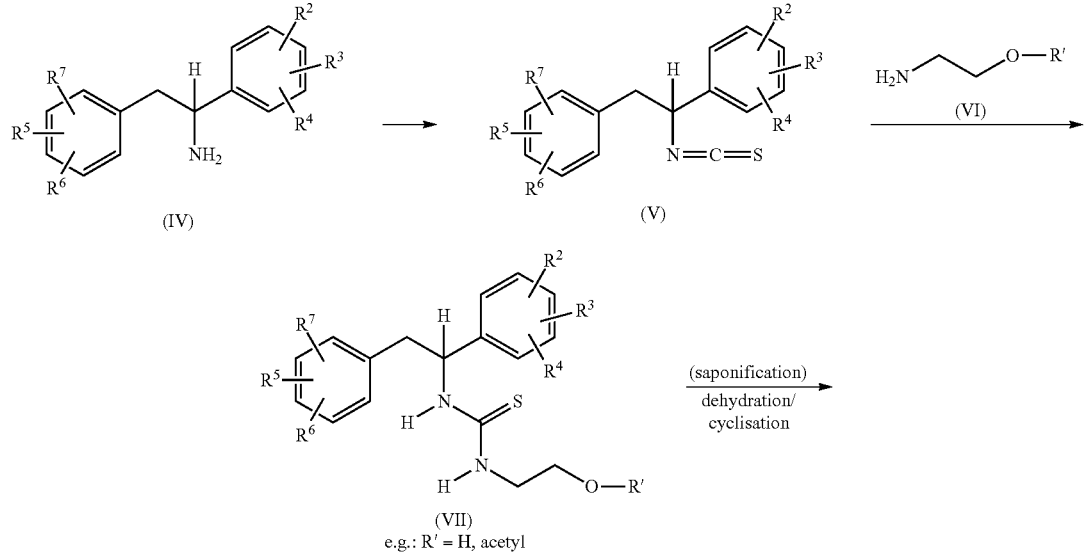

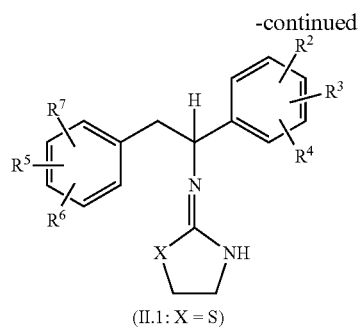

(II.1: X = S)

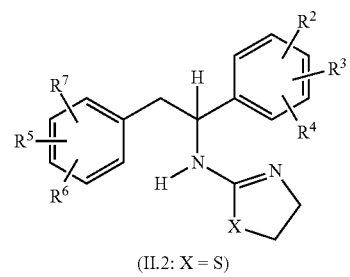

(II.2: X = S)

According to the method outlined in scheme 2, a 1,2-diphenylaminoethane IV is converted into the corresponding isothiocyanate V by conventional means, e.g. by reacting IV with thiophosgene (see e.g. Houben-Weyl, E4, "Methoden der Organischen Chemie", chapter IIIc, pp. 837-842). The isothiocyanate V is then reacted with an aminoethanol derivative of the formula VI, thereby obtaining the thiourea compound of the formula VII. The reaction of the aminoethanol derivative VI with isothiocyanate V can be performed in accordance with standard methods of organic chemistry, see e.g. Biosci. Biotech. Biochem. 1992, 56 (7), 1062-1065. The thus obtained thioureas can be cyclized by conventional means thereby obtaining the desired thiazoline compound of the formula II, with X being S. Cyclization of compound VII can be achieved e.g. under acid catalysis or under dehydrating conditions e.g. by Mitsunobu's reaction (see Tetrahedron Letters 1999, 40, 3125-3128).

Compounds of the formula II, with X being O, can be obtained by the method outlined in scheme 3. In scheme 3 Y means OH or halogen and Z means hydrogen, alkyl or halogen, especially fluorine.

Scheme 3

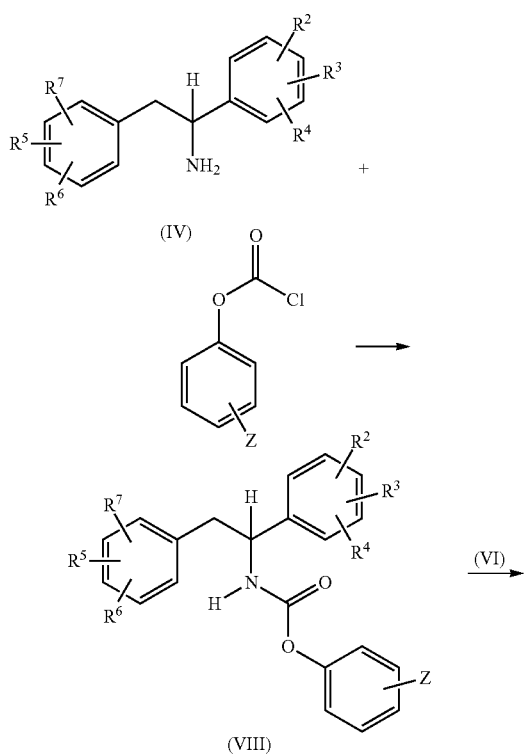

(VIII)

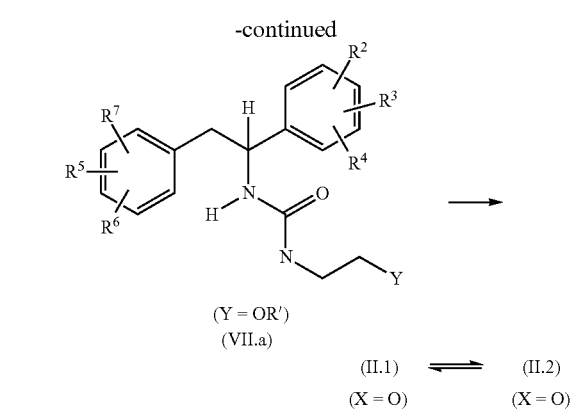

(Y = OR')
(VII.a)

(II.1) ⇌ (II.2)
(X = O)    (X = O)

According to scheme 3, diphenylaminoethanes IV are converted into the corresponding carbamates of the formula VIII by reacting II with a phenyl chloroformate such as 4-chlorophenyl chloroformat according to standard methods (see e.g. Pesticide Biochemistry and Physiology 30, 1988, p. 190-197). The thus obtained carbamate VIII is reacted with the aminoethanol derivative of formula VI in the presence of trimethylchlorosilane according to the method described in J. Org. Chem. 1998, 63, 8515-8521. Thereby, 2-hydroxyethyl ureas of the formula VII.a {Y=OH} are obtained. The 2-hydroxyethylureas can be cyclized to the oxazoline compounds II according to the procedures described in Org. Lett. 1999, 1, 1705-1708 or Tetrahedron Lett. 1992, 33, 2807-2810.

Alternatively, substituted 2-chloroethyl ureas VII.a {Y=halogen} can be cyclized according to the methods described in Bioorg. Med. Chem. Lett. 1994, 4, 2317-2322.

Scheme 4

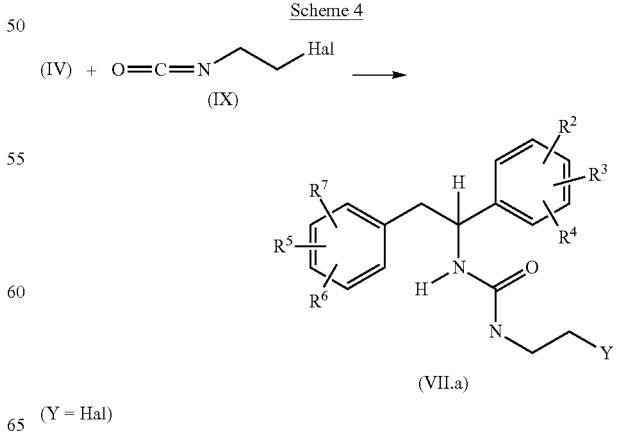

(Y = Hal)

In scheme 4 Hal is halogen, in particular chlorine. Chloroethyl ureas VII.a can be obtained from the corresponding diphenylethylamines of formula IV by reaction with 2-haloethylisocyanate IX, especially 2-chloroethylisocyanate.

The diphenylethylamines of formula IV can for instance be prepared by addition of appropriately substituted anion equivalents, for examples of organometallic compounds XII, to appropriately substituted C=N bond containing compounds XI (cf. for example Chem. Rev. 1998, 98, 1407-1438) as outlined in scheme 5.

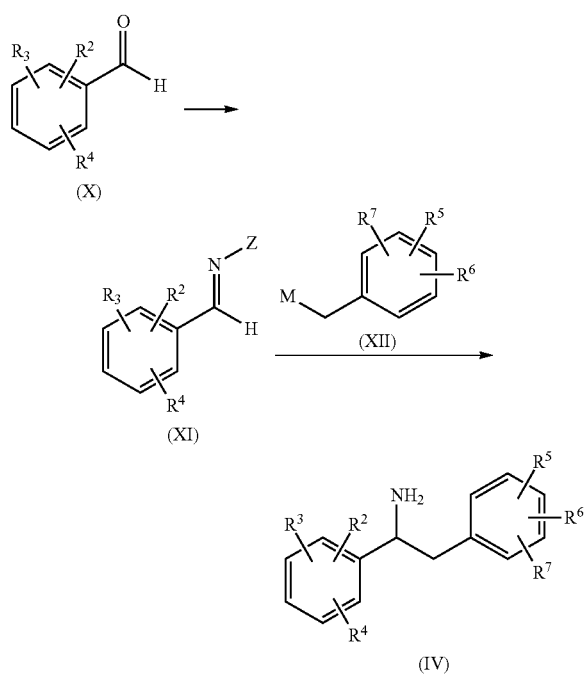

Z = SiCH₃, BH₂, SOC(CH₃)₃, phosphinoyl, acyl etc.
M = metal(-halide),
e.g. Na, K, Li, MgCl, MgBr Starting imines XI can for example be prepared by methods familiar to an organic chemist from the corresponding aldehydes X by reaction with amines in the presence of a dehydrating agent or from nitriles by reduction (e.g. J. Org. Chem. 1990, 55, 4199-4200) and are well known in the art. Starting imines XI include also chiral compounds as for example described in Tetrahedron 1999, 55, 8883-8904.

A general method for the preparation of compounds similar to the amines of formula IV starting from the corresponding carboxamides has been described in U.S. Pat. No. 4,536,599.

The compounds of formula I.2 can alternatively be obtained by converting primary amines of formula IV into secondary amines of formula XIV for instance by reductive amination (cf. scheme 6) followed by the addition of appropriately substituted isothiocyanates of formula XV, such as e. g. acetoxyethyl isothiocyanate, and subsequent saponification. The isothiocyanate of the formula XV can for instance be prepared according to the procedures described in Coll. Czech. Chem. Comm. 1986, 51, 112-117.

The thus obtained thioureas XVI can be cyclized by conventional means thereby obtaining the azoline compound of formula I.2. Cyclization of compound XVI can be achieved according to the reaction outlined in scheme 2 for the preparation of compounds of formula II.

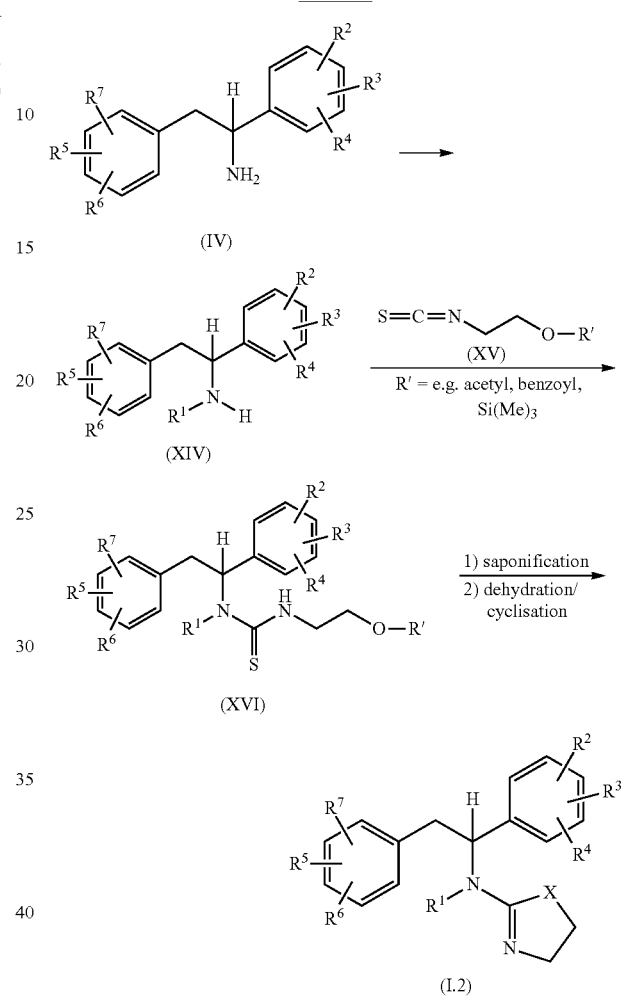

Alternatively, the isothiocyanate V (cf. scheme 2) is reacted with an appropriately substituted aminoethanol of formula XVII, thereby obtaining the thiourea XVIII, as outlined in scheme 7. The reaction of the aminoethanol XVII with isothiocyanate V can be performed in accordance with the method outlined in scheme 2. The thiourea XVIII can be converted to the compound of formula I.1 according to the method outlined in schemes 2 or 7.

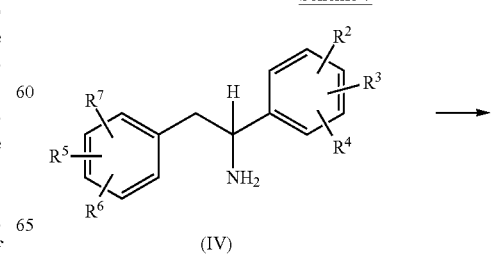

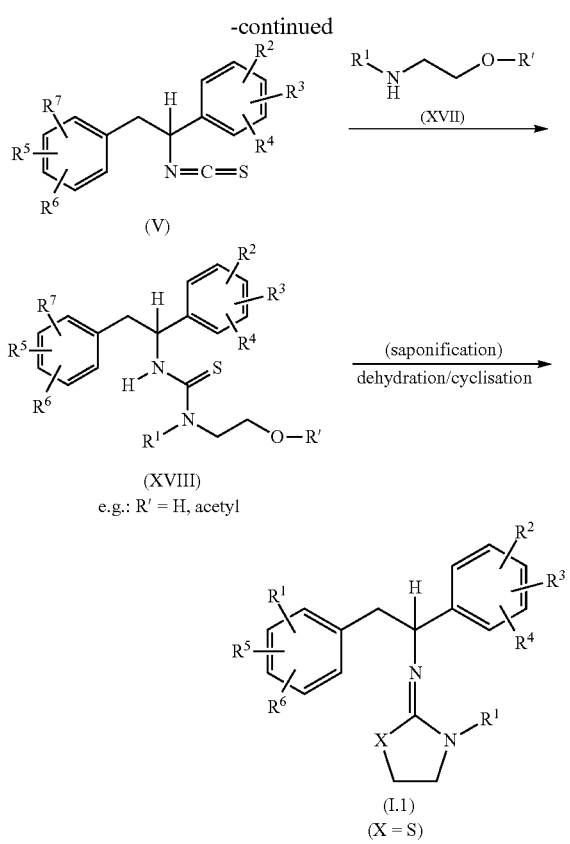

Alternatively, compounds of the general formula I.2 can be prepared according to scheme 8 and according to similar procedures described in WO 2006/125748 or for analogous benzylaminothiazolines in WO 2007/020377 by reacting appropriately substituted azolines XIV (cf. scheme 6) with azoline-compounds XIX.

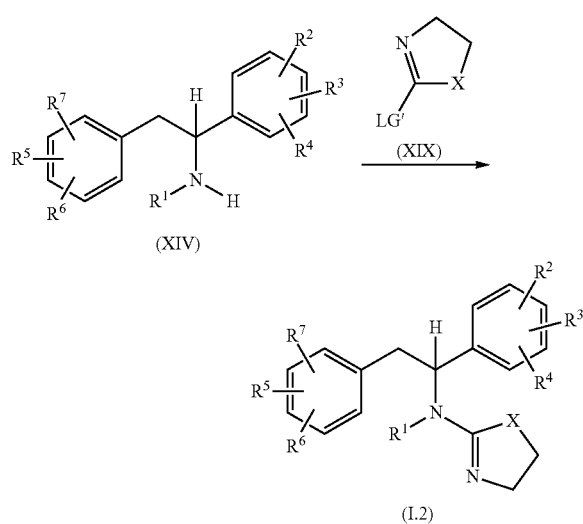

LG' = halogen,
alkylsulfonyl,
arylsulfonyl etc.

As a rule, the compounds of the formula I can be prepared by the methods described above. If individual compounds cannot be prepared via the above-described routes, they can be prepared by derivatization of other compounds of formula I or by customary modifications of the synthesis routes described. For example, in individual cases, certain compounds of formula I can advantageously be prepared from other compounds of formula I by ester hydrolysis, amidation, esterification, ether cleavage, olefination, reduction, oxidation and the like.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colourless or pale brown viscous oils which are freed or purified from volatile components under reduced pressure and at moderately elevated temperature. If the intermediates and end products are obtained as solids, they may be purified by recrystallization or digestion.

Due to their excellent activity, the compounds of formula I may be used for controlling animal pests.

Accordingly, the present invention also provides a method for controlling animal pests which method comprises treating the pests, their food supply, their habitat or their breeding ground or a plant, plant propagation materials, soil, area, material or environment in which the pests are growing or may grow, or the materials, plants, plant propagation materials, soils, surfaces or spaces to be protected from pest attack or infestation with a pesticidally effective amount of a compound of the formula I or a salt thereof or a composition as defined above.

Preferably, the method of the invention serves for protecting plant propagation materials, in particular seeds, and the plant which grows therefrom from animal pest attack or infestation and comprises treating the plant propagation materials, in particular the seed, with a pesticidally effective amount of a compound of the formula I or an agriculturally acceptable salt thereof as defined above or with a pesticidally effective amount of an agricultural composition as defined above and below. The method of the invention is not limited to the protection of the "substrate" (plant, plant propagation materials such as seed, soil material etc.) which has been treated according to the invention, but also has a preventive effect, thus, for ex-ample, according protection to a plant which grows from a treated plant propagation materials, the plant itself not having been treated.

In the sense of the present invention, "animal pests" are preferably selected from arthropods and nematodes, more preferably from harmful insects, arachnids and nematodes, and even more preferably from insects, acarids and nematodes.

The invention further provides an agricultural composition for combating such animal pests, which comprises such an amount of at least one compound of the general formula I or at least one agriculturally useful salt thereof and at least one inert liquid and/or solid agronomically acceptable carrier that has a pesticidal action and, if desired, at least one surfactant.

Such a composition may contain a single active compound of the formula I or a salt thereof or a mixture of several active compounds of the formula I or their salts according to the pre-sent invention. The composition according to the present invention may comprise an individual isomer or mixtures of isomers as well as individual tautomers or mixtures of tautomers.

The compounds of the formula I and the pesticidal compositions comprising them are effective agents for controlling arthropod pests and nematodes. Animal pests controlled by the compounds of formula I include for example:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica* 12-punctata, *Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* dipterans (Diptera), for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* thrips (Thysanoptera), e.g. *Dichromothrips corbetti, Frankliniella fusca, Frankliniella occidentalis, Frankliniella tritici, Scirtothrips citri, Thrips oryzae, Thrips palmi* and *Thrips tabaci;* hymenopterans (Hymenoptera), e.g. *Athalia rosae, Atta cephalotes, Atta sexdens, Atta texana, Hoplocampa minuta, Hoplocampa testudinea, Monomorium pharaonis, Solenopsis geminata* and *Solenopsis invicta;* heteropterans (Heteroptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis* and *Thyanta perditor;* homopterans (Homoptera), e.g. *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus persicae, Myzus varians, Nasonovia ribisnigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Sogatella furcifera Trialeurodes vaporariorum, Toxoptera aurantiiand,* and *Viteus vitifolii;* termites (Isoptera), e.g. *Calotermes flavicollis, Leucotermes flavipes, Reticulitermes flavipes, Reticulitermes lucifugus* and *Termes natalensis;* orthopterans (Orthoptera), e.g. *Acheta domestica, Blatta orientalis, Blattella germanica, Forficula auricularia, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;*

Arachnoidea, such as arachnids (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis;*

Siphonatera, e.g. *Xenopsylla cheopis, Ceratophyllus* spp.;

The compositions and compounds of formula I are useful for the control of nematodes, especially plant parasitic nematodes such as root knot nematodes, *Meloidogyne hapla, Meloidogyne incognita, Meloidogyne javanica,* and other *Meloidogyne* species;

cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

In a preferred embodiment of the invention the compounds of formula I are used for controlling insects or arachnids, in particular insects of the orders Lepidoptera, Coleoptera, Thysanoptera and Homoptera and arachnids of the order Acarina. The compounds of the formula I according to the present invention are particularly useful for controlling insects of the order Thysanoptera and Homoptera.

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of formula I can be converted into the customary formulations, for example solutions, emulsions, suspensions, dusts, powders, pastes and granules. The use form depends on the particular intended purpose; in each case, it should ensure a fine and even distribution of the compound according to the invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. Nos. 4,144,050, 3,920,442, 5,180,587, 5,232,701, 5,208, 030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Examples of suitable solvents are water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (N-methyl-pyrrolidone [NMP], N-octyl-pyrrolidone [NOP]), acetates (glycol diacetate), glycols, fatty acid dimethylamides, fatty acids and fatty acid esters. In principle, solvent mixtures may also be used.

Suitable emulsifiers are non-ionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants used are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sul-fonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, highly polar solvents, for example dimethyl sulfoxide, N-methylpyrrolidone or water.

Also anti-freezing agents such as glycerin, ethylene glycol, propylene glycol and bactericides such as can be added to the formulation.

Suitable antifoaming agents are for example antifoaming agents based on silicon or magnesium stearate.

A suitable preservative is e.g. dichlorophen.

Seed treatment formulations may additionally comprise binders and optionally colorants.

Binders can be added to improve the adhesion of the active materials on the seeds after treatment. Suitable binders are block copolymers EO/PO surfactants but also polyvinylalcoholsl, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®).

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound(s). In this case, the active compound(s) are employed in a purity of from 90% to 100% by weight, preferably 95% to 100% by weight (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compounds of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended pur-poses; they are intended to ensure in each case the finest possible distribution of the active compound(s) according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. However, it is also possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1% per weight.

The active compound(s) may also be used successfully in the ultra-low-volume process (ULV), it being possible to apply formulations comprising over 95% by weight of active compound, or even to apply the active compound without additives.

The following are examples of formulations:

1. Products for dilution with water for foliar applications. For seed treatment purposes, such products may be applied to the seed diluted or undiluted.

A) Water-Soluble Concentrates (SL, LS)

10 parts by weight of the active compound(s) are dissolved in 90 parts by weight of water or a water-soluble solvent. As an alternative, wetters or other auxiliaries are added. The active compound(s) dissolves upon dilution with water, whereby a formulation with 10% (w/w) of active compound(s) is obtained.

B) Dispersible Concentrates (DC)

20 parts by weight of the active compound(s) are dissolved in 70 parts by weight of cyclohexanone with addition of 10 parts by weight of a dispersant, for example polyvinylpyrrolidone. Dilution with water gives a dispersion, whereby a formulation with 20% (w/w) of active compound(s) is obtained.

C) Emulsifiable Concentrates (EC)

15 parts by weight of the active compound(s) are dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compound(s) is obtained.

D) Emulsions (EW, EO, ES)

25 parts by weight of the active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound(s) is obtained.

E) Suspensions (SC, OD, FS)

In an agitated ball mill, 20 parts by weight of the active compound(s) are comminuted with addition of 10 parts by weight of dispersants, wetters and 70 parts by weight of water or of an organic solvent to give a fine active compound(s) suspension. Dilution with water gives a stable suspension of the active compound(s), whereby a formulation with 20% (w/w) of active compound(s) is obtained.

F) Water-Dispersible Granules and Water-Soluble Granules (WG, SG)

50 parts by weight of the active compound(s) are ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound(s), whereby a formulation with 50% (w/w) of active compound(s) is obtained.

G) Water-Dispersible Powders and Water-Soluble Powders (WP, SP, SS, WS)

75 parts by weight of the active compound(s) are ground in a rotor-stator mill with addition of 25 parts by weight of dispersants, wetters and silica gel. Dilution with water gives a stable dispersion or solution of the active compound(s), whereby a formulation with 75% (w/w) of active compound(s) is obtained.

H) Gel-Formulation (GF)

In an agitated ball mill, 20 parts by weight of the active compound(s) are comminuted with addition of 10 parts by weight of dispersants, 1 part by weight of a gelling agent wetters and 70 parts by weight of water or of an organic solvent to give a fine active compound(s) suspension. Dilution with water gives a stable suspension of the active compound(s), whereby a formulation with 20% (w/w) of active compound(s) is obtained.

2. Products to be applied undiluted for foliar applications. For seed treatment purposes, such products may be applied to the seed diluted or undiluted.

I) Dustable Powders (DP, DS)

5 parts by weight of the active compound(s) are ground finely and mixed intimately with 95 parts by weight of finely divided kaolin. This gives a dustable product having 5% (w/w) of active compound(s)

J) Granules (GR, FG, GG, MG)

0.5 parts by weight of the active compound(s) is ground finely and associated with 95.5 parts by weight of carriers, whereby a formulation with 0.5% (w/w) of active compound(s) is obtained. Current methods are extrusion, spray-drying or the fluidized bed. This gives granules to be applied undiluted for foliar use.

K) ULV Solutions (UL)

10 parts by weight of the active compound(s) are dissolved in 90 parts by weight of an organic solvent, for example xylene. This gives a product having 10% (w/w) of active compound(s), which is applied undiluted for foliar use.

The compounds of formula I are also suitable for the treatment of plant propagation materials such as seeds. Conventional seed treatment formulations include for example flowable concentrates FS, solutions LS, powders for dry treatment DS, water dispersible powders for slurry treatment WS, water soluble powders SS and emulsion ES and EC and gel formulation GF. These formulations can be applied to the seed diluted or undiluted. Application to the seeds is carried out before sowing, either directly on the seeds or after having preger-minated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Other preferred FS formulations of compounds of formula I for seed treatment comprise from 0.5 to 80 wt % of the active ingredient, from 0.05 to 5 wt % of a wetter, from 0.5 to 15 wt % of a dispersing agent, from 0.1 to 5 wt % of a thickener, from 5 to 20 wt % of an anti-freeze agent, from 0.1 to 2 wt % of an anti-foam agent, from 1 to 20 wt % of a pigment and/or a dye, from 0 to 15 wt % of a sticker/adhesion agent, from 0 to 75 wt % of a filler/vehicle, and from 0.01 to 1 wt % of a preservative.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part).

For use against ants, termites, wasps, flies, mosquitos, crickets, or cockroaches, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethyl-formamide, N methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for exam-ple are N,N-diethylmetatoluamide (DEET), N,N-diethylphenylacetamide (DEPA), 1-(3-cyclohexan-1-yl-carbonyl)-2-methylpiperine, (2-hydroxymethyl-cyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant ex-tracts like limonene, eugenol, (+)-Eucamalol (1), (−)-1-epi-eucamalol or crude plant ex-tracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic ac-ids (such as such as vinyl acetate and vinyl versatate), acrylic and methacrylic esters of alcohols, such as butyl acrylate, 2-ethylhexylacrylate, and methyl acrylate, mono- and diethylenically unsaturated hydrocarbons, such as styrene, and aliphatic diens, such as butadiene.

The impregnation of curtains and bednets is done in general by dipping the textile material into emulsions or dispersions of the compound of the formula I or spraying them onto the nets.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of formula I into contact with each other, and "seed dressing" to methods of seed treatment which provide the seeds with an amount of the compounds of formula I, i.e. which generate a seed comprising the compound of formula I. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of formula I or the enantiomers or veterinarily acceptable salts thereof are in particular also suitable for being used for combating parasites in and on animals.

A further object of the present invention is thus to provide new methods for controlling parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers, diastereomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers, diastereomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers, diastereomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly, it has now been found that compounds of formula I are suitable for combating endo- and ectoparasites in and on animals.

Compounds of formula I or the enantiomers, diastereomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers, diastereomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers, diastereomers or veterinarily acceptable salts thereof and compositions comprising them are suitable for systemic and/or non-systemic control of ecto- and/or endoparasites. They are active against all or some stages of development.

The compounds of formula I, the enantiomers, diastereomers or veterinarily acceptable salts thereof are especially useful for combating ectoparasites.

The compounds of formula I, the enantiomers, diastereomers or veterinarily acceptable salts thereof are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inor-nata, Culiseta melanura, Dermatobia hominis, Fannia canicularis, Gasterophilus intes-tinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus,*

*Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the formula I and compositions containing them for combating mosquitoes is especially preferred.

The use of the compounds of formula I, the enantiomers, diastereomers or veterinarily acceptable salts thereof and compositions containing them for combat-ing flies is a further preferred embodiment of the present invention.

Furthermore, the use of the compounds of formula I, the enantiomers, diastereomers or veterinarily acceptable salts thereof and compositions containing them for combating fleas is especially preferred.

The use of the compounds of formula formula I, the enantiomers, diastereomers or veterinarily acceptable salts thereof and compositions containing them for combating ticks is a further preferred embodiment of the present invention.

The compounds of the compounds of formula I, the enantiomers, diastereomers or veterinarily acceptable salts thereof also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the compounds of formula I, the enantiomers, diastereomers or veterinarily acceptable salts thereof may be formulated as animal feeds, animal feed premixes, animal feed concentrates, pills, solutions, pastes, suspensions, drenches, gels, tablets, boluses and capsules. In addi-tion, the formula I compounds may be administered to the animals in their drinking water. For oral administration, the dosage form chosen should provide the animal with 0.01 mg/kg to 100 mg/kg of animal body weight per day of the formula I compound (and likewise the enantiomers, diastereomers or veterinarily acceptable salts thereof), preferably with 0.5 mg/kg to 100 mg/kg of animal body weight per day.

Alternatively, the compounds of formula I, the enantiomers, diastereomers or veterinarily acceptable salts thereof may be administered to animals parenterally, for example, by intraruminal, intramuscular, intravenous or subcutaneous injection. The compounds of formula I, the enantiomers, diastereomers or veterinarily acceptable salts thereof may be dispersed or dissolved in a physiologically acceptable carrier for subcutaneous injection. Alternatively, the compounds of formula I, the enantiomers, diastereomers or veterinarily acceptable salts thereof may be formulated into an implant for subcutaneous administration. In addition the compound of formula I, the enantiomers, diastereomers or veterinarily acceptable salts thereof may be transdermally administered to animals. For parenteral administration, the dosage form chosen should provide the animal with 0.01 mg/kg to 100 mg/kg of animal body weight per day of the compound of formula I (or the enantiomers, diastereomers or veterinarily acceptable salts thereof).

The compounds of formula I (and likewise the enantiomers, diastereomers or veterinarily acceptable salts thereof) may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compound of formula I. In addition, the compounds of formula I, the enantiomers, diastereomers or veterinarily acceptable salts thereof may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents are water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol monobutyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length C8-C12 or other specially selected natural fatty acids, partial glyceride mixtures of saturated or unsaturated fatty acids possibly also containing hydroxyl groups, mono- and diglycerides of the C8-C10 fatty acids, fatty acid esters such as ethyl stearate, di-n-butyryl adipate, hexyl laurate, dipropylene glycol perlargonate, esters of a branched fatty acid of medium chain length with saturated fatty alcohols of chain length C16-C18, isopropyl myristate, isopropyl palmitate, caprylic/capric acid esters of saturated fatty alcohols of chain length C12-C18, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I and/or of an acceptable salts thereof.

Generally, it is favorable to apply the compounds of formula I and/or an acceptable salts thereof in total amounts of 0.5 mg/kg to 100 mg/kg per day, preferably 1 mg/kg to 50 mg/kg per day.

Ready-to-use preparations contain the compounds of the formula I, acting against parasites, preferably ectoparasites, and/or an acceptable salts thereof, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds of the formula I, acting against ectoparasites, and/or an acceptable salts thereof, in concentrations of 0.5 to 90 percent by weight, preferably of 1 to 50 percent by weight.

Furthermore, the preparations comprise the compounds of formula I and/or an acceptable salts thereof against endoparasites in concentrations of 10 ppm to 2 per cent by weight, preferably of 0.05 to 0.9 percent by weight, very particularly preferably of 0.005 to 0.25 percent by weight.

In a preferred embodiment of the present invention, the compositions comprising the compounds of formula I and/or an acceptable salts thereof are applied dermally/topically.

In a further preferred embodiment, the topical application is conducted in the form of compound-containing shaped articles such as collars, medallions, ear tags, bands for fixing at body parts, and adhesive strips and foils.

Generally, it is favorable to apply solid formulations which release compounds of formula I and/or an acceptable salts thereof in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

Compositions to be used according to this invention may also contain other active ingredients, for example other pesticides, insecticides, herbicides, fungicides, other pesticides, or bactericides, fertilizers such as ammonium nitrate, urea, potash, and super-phosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

These agents can be admixed with the agents used according to the invention in a weight ratio of 1:10 to 10:1. Mixing the compounds of the formula I and/or an acceptable salts thereof or the compositions comprising them in the use form as pesticides with other pesticides frequently results in a broader pesticidal spectrum of action.

The following list of pesticides A (hereinafter also mixing partner A) together with which the compounds of the formula I and/or an acceptable salts thereof can be used and with which potential synergistic effects might be produced, is intended to illustrate the possible combinations, but not to impose any limitation:

A.1. Organo(thio)phosphates: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

A.2. Carbamates: aldicarb, alanycarb, bendiocarb, benfuracarb, butocarboxim, butoxy-carboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

A.3. Pyrethroids: acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, permethrin, phenothrin, prallethrin, resmethrin, RU 15525, silafluofen, tefluthrin, tetramethrin, tralomethrin, transfluthrin, ZXI 8901;

A.4. Juvenile hormone mimics: hydroprene, kinoprene, methoprene, fenoxycarb, pyriproxyfen;

A.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), thiacloprid, thiocyclam, thiosultap-sodium and AKD1022.

A.6. GABA gated chloride channel antagonist compounds: chlordane, endosulfan, gamma-HCH (lindane); acetoprole, ethiprole, fipronil, pyrafluprole, pyriprole, vaniliprole, the phenylpyrazole compound of formula A6.1

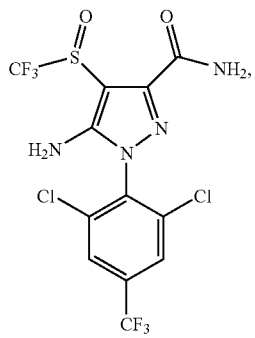

(A6.1)

A.7. Chloride channel activators: abamectin, emamectin benzoate, milbemectin, lepimectin;

A.8. METI I compounds: fenazaquin, fenpyroximate, pyrimidifen, pyridaben, tebufenpyrad, tolfenpyrad, flufenerim, rotenone;

A.9. METI II and III compounds: acequinocyl, fluacyprim, hydramethylnon;

A.10. Uncouplers of oxidative phosphorylation: chlorfenapyr, DNOC;

A.11. Inhibitors of oxidative phosphorylation: azocyclotin, cyhexatin, diafenthiuron, fenbutatin oxide, propargite, tetradifon;

A.12. Moulting disruptors: cyromazine, chromafenozide, halofenozide, methoxyfenozide, tebufenozide;

A.13. Synergists: piperonyl butoxide, tribufos;

A.14. Sodium channel blocker compounds: indoxacarb, metaflumizone;

A.15. Fumigants: methyl bromide, chloropicrin sulfuryl fluoride;

A.16. Selective feeding blockers: crylotie, pymetrozine, flonicamid;

A.17. Mite growth inhibitors: clofentezine, hexythiazox, etoxazole;

A.18. Chitin synthesis inhibitors: buprofezin, bistrifluron, chlorfluazuron, diflubenzuron, flucycloxuron, flufenoxuron, hexaflumuron, lufenuron, novaluron, noviflumuron, teflubenzuron, triflumuron;

A.19. Lipid biosynthesis inhibitors: spirodiclofen, spiromesifen, spirotetramat;

A.20. Octapaminergic agonsits: amitraz;

A.21. Ryanodine receptor modulators: flubendiamide;

A.22. Various: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulphur compounds, tartar emetic and sulfoximine compounds A22.1, A22.2 or A22.3:

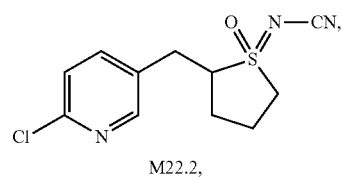

M22.2,

A22.1

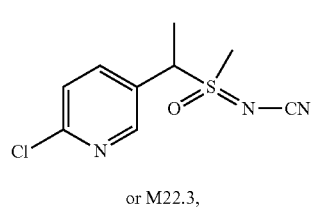

or M22.3,

A22.2

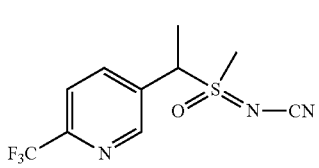

A22.3 pyrimidinyl alkynylether compounds A22.4 or thiadiazolyl alkynylether compounds A22.5,

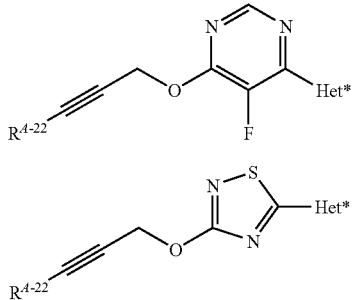

wherein $R^{A-22}$ is methyl or ethyl and Het* is 3,3-dimethylpyrrolidin-1-yl, 3-methylpiperidin-1-yl, 3,5-dimethylpiperidin-1-yl, 3-trifluormethylpiperidin-1-yl, hexahydroazepin-1-yl, 2,6-dimethylhexahydroazepin-1-yl or 2,6-dimethylmorpholin-4-yl;

A.23. N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl;

A.24. Anthranilamides: chloranthraniliprole, the compound of formula A24.1

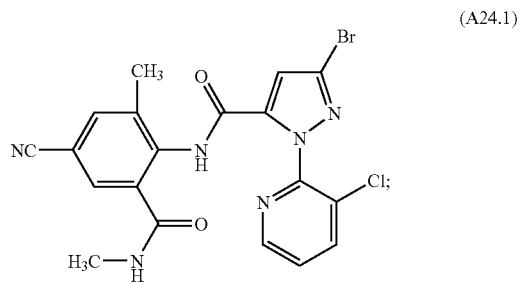

A.25. Malononitrile compounds: $CF_2HCF_2CF_2CF_2CH_2C(CN)_2CH_2CH_2CF_3$, (2-(2,2,3,3,4,4,5,5-octafluoropentyl)-2-(3,3,3-trifluoro-propyl)malononitrile), $CF_3(CH_2)_2C(CN)_2CH_2(CF_2)_5CF_2H$, (2-(2,2,3,3,4,4,5,5,6,6,7,7-Dodecafluoroheptyl)-2(3,3,3-trifluoro-propyl)-malononitrile), $CF_3(CH_2)_2C(CN)_2(CH_2)_2C(CF_3)_2F(2-(3,4,4,4-Tetrafluoro-3-trifluoromethyl-butyl)-2-(3,3,3-trifluoro-propyl)-malononitrile)$, $CF_3(CH_2)_2C(CN)_2(CH_2)_2(CF_2)_3CF_3(2-(3,3,4,4,5,5,6,6,6-Nonafluoro-hexyl)-2-(3,3,3-trifluoro-propyl)-malononitrile)$, $CF_2H(CF_2)_3CH_2C(CN)_2CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3(2-(2,2,3,3,4,4,5,5,5-Nonafluoro-pentyl)-2-(3,3,3-trifluoro-propyl)-malononitrile)$, $CF3(CF_2)_2CH_2C(CN)_2CH_2(CF_2)3CF_2H(2-(2,2,3,3,4,4,4-Heptafluoro-butyl)-2-(2,2,3,3,4,4,5,5-octafluoro-pentyl)-malononitrile)$, $CF_3CF_2CH_2C(CN)_2CH_2(CF_2)_3CF_2H(2-(2,2,3,3,4,4,5,5-Octafluoro-pentyl)-2-(2,2,3,3,3-pentafluoro-propyl)-malononitrile)$, $CF_2HCF_2CF_2CF_2CH_2C(CN)_2CH_2CH_2CF_2CF_3(2-(2,2,3,3,4,4,5,5-octafluoropentyl)-2-(3,3,4,4,4-pentafluorobutyl)-malonodinitrile)$, $CF_3(CH_2)_2C(CN)_2CH_2(CF_2)_3CF_2H(2-(2,2,3,3,4,4,5,5-octafluoro-pentyl)-2-(3,3,3-trifluoro-butyl)-malononitrile)$;

A.26. Microbial disruptors: *Bacillus thuringiensis* subsp. *Israelensis, Bacillus sphaericus, Bacillus thuringiensis* subsp. *Aizawai, Bacillus thuringiensis* subsp. *Kurstaki, Bacillus thuringiensis* subsp. *Tenebrionis*.

The commercially available compounds of the group A may be found in The Pesticide Manual, 13th Edition, British Crop Protection Council (2003) among other publications.

Thioamides of formula A6.1 and their preparation have been described in WO 98/28279. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4822779. Pyrafluprole and its preparation have been described in JP 2002193709 and in WO 01/00614. Pyriprole and its preparation have been described in WO 98/45274 and in U.S. Pat. No. 6335357. Amidoflumet and its preparation have been described in U.S. Pat. No. 6221890 and in JP 21010907. Flufenerim and its prepara-tion have been described in WO 03/007717 and in WO 03/007718. AKD 1022 and its preparation have been described in U.S. Pat. No. 6300348. Chloranthraniliprole has been described in WO 01/70671, WO 03/015519 and WO 05/118552. Anthranilamide deriva-tives of formula M24.1 have been described in WO 01/70671, WO 04/067528 and WO 05/118552. Cyflumetofen and its preparation have been described in WO 04/080180. The aminoquinazolinone compound pyrifluquinazon has been described in EP A 109 7932. Sulfoximine derivatives of for- mulae M22.1, M22.2 or M22.3 or in analogy thereof and their preparation methods have been described in WO 2006/ 060029. The alkynylether compounds M22.4 and M22.5 are described e.g. in JP 2006131529. Organic sulfur compounds have been described in WO 2007060839. The malononitrile compounds have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

The animal pest, i.e. arthropodes and nematodes, the plant, soil or water in which the plant is growing can be contacted with the present compound(s) of the formula I and/or an agriculturally acceptable salt thereof or composition(s) containing them by any application method known in the art. As such, "contacting" in-cludes both direct contact (applying the compounds/compositions directly on the animal pest or plant—typically to the foliage, stem or roots of the plant) and indirect contact (applying the compounds/compositions to the locus of the animal pest or plant).

Moreover, animal pests may be controlled by contacting the target pest, its food supply, habitat, breeding ground or its locus with a pesticidally effective amount of compounds of formula I and/or an agriculturally acceptable salt thereof. As such, the application may be carried out before or after the infection of the locus, growing crops, or harvested crops by the pest.

"Locus" means a habitat, breeding ground, plant, in particular cultivated plant, plant propagation material such as seed, soil, area, material or environ-ment in which a pest or parasite is growing or may grow.

In general "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I, the agriculturally acceptable salt thereof and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of are applied not only to the surrounding soil surface or into the underfloor soil in order to protect wooden materials but it can also be applied to lumbered articles such as surfaces of the underfloor concrete, al-cove posts, beams, plywoods, furniture, etc., wooden articles such as particle boards, half boards, etc. and vinyl articles such as coated electric wires, vinyl sheets, heat insu-lating material such as styrene foams, etc. In case of application against ants doing harm to crops or human beings, the ant controller of the present invention is applied to the crops or the surrounding soil, or is directly applied to the nest of ants or the like.

The compounds of the invention can also be applied preventively to places at which occurrence of the pests is expected.

The compounds of formula I and/or an agriculturally acceptable salt thereof may also be used to protect growing plants from attack or infestation by pests by contacting the plant with a pesticidally effective amount of compounds of formula I and/or an agriculturally acceptable salt thereof. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient (i.e. compounds of the formula I and/or an agriculturally acceptable salt thereof or mixtures thereof with mixing partner A) ranges from 0.0001 to 500 g per 100 m$^2$, preferably from 0.001 to 20 g per 100 m$^2$.

Customary application rates in the protection of materials are, for example, from 0.01 g to 1000 g of active compound (i.e. compounds of the formula I and/or an agriculturally acceptable salt thereof or mixtures thereof with mixing partner A) per m$^2$ treated material, desirably from 0.1 g to 50 g per m$^2$.

Insecticidal compositions for use in the impregnation of materials typically contain from 0.001 to 95% by weight, preferably from 0.1 to 45% by weight, and more preferably from 1 to 25% by weight of at least one repellent and/or insecticide (i.e. compounds of the formula I and/or an agriculturally acceptable salt thereof or mixtures thereof with mixing partner A).

For use in bait compositions, the typical content of active ingredient (i.e. compounds of the formula I and/or an agriculturally acceptable salt thereof or mixtures thereof with mixing partner A) is from 0.001% by weight to 15% by weight, desirably from 0.001% by weight to 5% by weight of active compound.

For use in spray compositions, the content of active ingredient (i.e. compounds of the formula I and/or an agriculturally acceptable salt thereof or mixtures thereof with mixing partner A) is from 0.001 to 80% by weight, preferably from 0.01 to 50% by weight and most preferably from 0.01 to 15% by weight.

For use in treating crop plants, the rate of application of the active ingredients (i.e. compounds of the formula I and/or an agriculturally acceptable salt thereof or mixtures thereof with mixing partner A) may be in the range of 0.1 g to 4000 g per hectare, desirably from 25 g to 600 g per hectare, more desirably from 50 g to 500 g per hectare.

In the treatment of seed, the application rates of the compounds of the present invention or mixture with mixing partners A are generally from 0.1 g to 10 kg per 100 kg of plant propagation material such as seed, preferably from 1 g to 5 kg per 100 kg of seed, in particular from 1 g to 200 g per 100 kg of plant propagation material such as seed.

The present invention is now illustrated in further detail by the following examples.

PREPARATION EXAMPLES

Example 1

Preparation of 1-(3-prop-2-ynyl-thiazolidin-2-ylidene)amino-1-(2,3-dichlorophenyl)-2-(3,5-dimethylphenyl)-ethane (compound 1)

A mixture of 1-(4,5-dihydrothiazol-2-yl)-amino-1-(2,3-dichlorophenyl)-2-(3,5-dimethylphenyl)-ethane (150 mg), potassium carbonate (80 mg) and dimethyl formamide (DMF, 10 ml) was heated up to 60° C. and a solution of propargyl bromide (57 mg) in DMF (2 ml) was added. Stirring was continued for 4 h at the same temperature and continued at room temperature overnight. Aqueous work-up by dilution in ethyl acetate, washing with an aqueous potassium carbonate solution (5% strenght) and water and drying over sodium sulphate yielded a crude product that was purified by column chromatography over silica gel to give 13 mg of the title compound.
$^1$H-NMR (CDCl$_3$): δ=2.25 (s), 2.75-3.05 (m), 3.45 (mc), 4.25 (s), 4.65 (mc), 6.8 (mc), 7.1-7.55 ppm (m).

Example 2

Preparation of 1-{3-[3-(tetrahydropyran-2-yloxy)propyl]thiazolidin-2-ylidene}amino-1-(2,3-dichlorophenyl)-2-(3,5-dimethylphenyl)-ethane (compound 2)

A mixture of 1-(4,5-dihydrothiazol-2-yl)amino-1-(2,3-dichlorophenyl)-2-(3,5-dimethylphenyl)-ethane (300 mg), potassium tert.-butanolate and tetrahydrofuran (THF, 10 ml) was treated at room temperature with 2-(3-bromo-propoxy)-tetrahydropyran (210 mg) for 3 days. Aqueous work-up by dilution in ethyl acetate, washing with an aqueous potassium carbonate solution (5% strength) and water and drying over sodium sulphate yielded a crude product that was purified by column chromatography over silica gel to give 200 mg of the title compound.
$^1$H-NMR (CDCl$_3$): δ=1.45-1.95 (m), 2.25 (s), 2.3 (d), 2.7 (mc), 3.0 (mc), 3.35-3.6 (m), 3.85 (mc), 4.55-4.7 (mc), 6.75 (s), 6.8 (s), 7.1 (t), 7.4 (mc), 7.5 ppm (mc).

Example 3

Preparation of 1-(4,5,4',5'-tetrahydro-[2,3]-bithiazolyl-2'-ylidene)amino-1-(2,2-difluoro-benzo[1,3]dioxol-4-yl)-2-(3,5-dimethyl-phenyl)-ethane (compound 3)

A solution of 1-amino-1-(2,2-difluoro-benzo[1,3]dioxol-4-yl)-2-(3,5-dimethylphenyl)-ethane (0.39 g) in diethyl ether was treated at 0° C. with 2-chloroethyl isothiocyanate (0.16 g) and stirring was continued for 5 h at this temperature. The mixture was quenched with an aqueous sodium hydroxide solution (1 M, 4 ml) and water (15 ml) and stirred for 15 minutes. The organic phase was washed with water, the aqueous phase was extracted with diethyl ether, the combined organic phases were dried over sodium sulphate and the solvent was removed in vacuo. The remainder was purified by column chromatography to yield 0.1 g of the title compound.
$^1$H-NMR (CDCl$_3$): δ=2.2 (s), 3.0-3.3 (m), 4.0 (mc), 4.2 (mc), 4.55 (mc), 6.7 (s), 6.8 (s), 6.9 (mc), 7.05 (mc), 7.3 ppm (mc).

Example 4

Preparation of 2-[1-(2,3-dichlorophenyl)-2-(3,5-dimethylphenyl)ethylimino]-thiazolidine-3-carbothioic acid (3-trifluoromethylphenyl)amide (compound 4)

A solution of 1-(4,5-dihydrothiazol-2-yl)amino-1-(2,3-dichlorophenyl)-2-(3,5-dimethylphenyl)-ethane (0.25 g) in chloroform (10 ml) was treated with 1-isothiocyanato-3-trifluoromethylbenzene (0.13 g) at room temperature overnight. The solvent was evaporated in vacuo and the remainder was purified by column chromatography to yield 0.20 g of the title compound.
$^1$H-NMR (CDCl$_3$): δ=2.1 (s), 2.85-3.2 (m), 4.55 (mc), 4.9 (mc), 5.0 (mc), 6.65 (s), 6.8 (s), 7.1-7.75 (m), 14.6 ppm (s).

Example 5

Preparation of 1-[3-(toluene-4-sulfonyl)thiazolidin-2-ylidene]-amino-1-(2,3-Dimethyl-phenyl)-2-(3-tolyl)-ethane (compound 5)

A solution of 1-(4,5-dihydro-3H-thiazol-2-yl)amino-1-(2,3-dimethyl-phenyl)-2-(3-tolyl)-ethane (0.20 g) in THF (20 ml) was treated with potassium tert.-butanolate (0.10 g) and 4-methylbenzenesulfonyl chloride (0.14 g) and the mixture was stirred for 2 h at room temperature. Aqueous work-up by dilution in ethyl acetate, washing with an aqueous potassium carbonate solution (5% strenght) and water and drying over sodium sulphate yielded a crude product that was purified by column chromatography over silica gel to give 0.20 g of the title compound. Melting point: 141.0-144.0° C.

The compounds of formula I'.1 shown in table 2 hereinafter (examples 6 to 21)

$$\text{(I'.1)}$$

have been prepared in analogy to the preparation examples shown hereinbefore.

TABLE 2

| Ex. | X | R$^1$ | R$^2$ | R$^3$ | R$^4$ | R$^5$ | R$^6$ | Physico-chemical data (m.p [° C.], $^1$H-NMR (CDCl$_3$) [ppm]) |
|---|---|---|---|---|---|---|---|---|
| 6 | S | 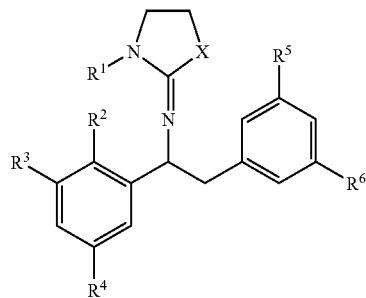 | H | H | H | Cl | H | δ = 2.95-3.15 (m), 3.95 (mc), 4.25 (mc), 4.75 (mc), 5.3 (d), 5.5 (d), 6.0 (mc), 6.9-7.3 (m) |

TABLE 2-continued
| Ex. | X | R¹ | R² | R³ | R⁴ | R⁵ | R⁶ | Physico-chemical data (m.p [° C.], ¹H-NMR (CDCl₃) [ppm]) |
|---|---|---|---|---|---|---|---|---|
| 7 | S | 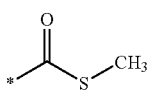 | H | H | H | Cl | H | 104.0-106.0 |
| 8 | O | 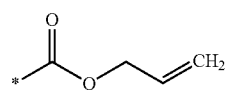 | H | H | H | Cl | H | 2.95 (mc), 3.75-4.15 (m), 4.7-4.85 (m), 5.3 (d), 5.5 (d), 6.0 (mc), 6.95-7.4 (m) |
| 9 | S | 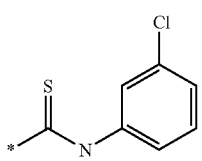 | CH₃ | CH₃ | H | CH₃ | CH₃ | 2.15 (s), 2.25 (s), 2.30 (s), 2.9-3.15 (m), 4.5 (mc), 4.7 (mc), 4.85 (mc), 6.65 (s), 6.8 (s), 7.05-7.4 (m), 7.55 (s) |
| 10 | S | 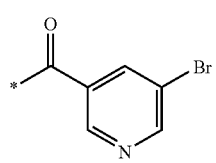 | Cl | Cl | H | CH₃ | CH₃ | 2.25 (s), 2.5 (mc), 2.75 (mc), 3.15 (mc), 4.0 (mc), 4.2 (mc), 4.75 (mc), 6.45 (mc), 6.55 (s), 7.05 (t), 7.3 (d), 8.9 (s), 8.65 (s), 8.75 (s) |
| 11 | S | 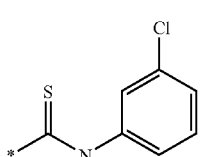 | Cl | Cl | H | CH₃ | CH₃ | 148.0-149.0 |
| 12 | S | 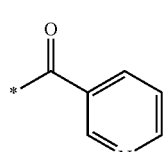 | Cl | Cl | H | CH₃ | CH₃ | 2.25 (s), 2.45 (mc), 2.75 (mc), 3.15 (mc), 4.0 (mc), 4.2 (mc), 4.65 (mc), 6.45 (mc), 6.55 (s), 6.8 (s), 6.95 (t), 8.7 (s), 8.8 (s) |
| 13 | S | 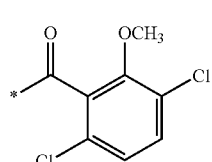 | Cl | Cl | H | CH₃ | CH₃ | 50.0-52.0 |
| 14 | S | 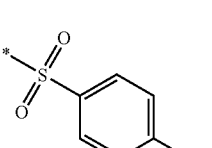 | Cl | Cl | H | CH₃ | CH₃ | 2.2 (s), 2.45 (s), 2.65 (mc), 2.9-3.1 (m), 3.9 (mc), 4.15 (mc), 4.45 (mc), 6.45 (s), 6.8 (s), 7.1 (mc), 7.2-7.35 (m), 7.95 (d) |
| 15 | S | 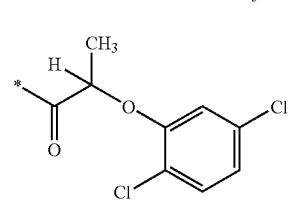 | Cl | Cl | H | CH₃ | CH₃ | 52.0-55.0 |
| 16 | S | 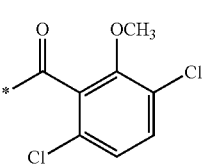 | CH₃ | CH₃ | H | CH₃ | CH₃ | 140.0-145.0 |

TABLE 2-continued

| Ex. | X | R¹ | R² | R³ | R⁴ | R⁵ | R⁶ | Physico-chemical data (m.p [° C.], $^1$H-NMR (CDCl$_3$) [ppm]) |
|---|---|---|---|---|---|---|---|---|
| 17 | S | 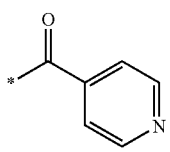 | Cl | Cl | H | CH$_3$ | CH$_3$ | 136.0-143.0 |
| 18 | S | 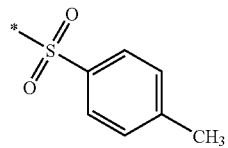 | CH$_3$ | CF$_3$ | H | CH$_3$ | CH$_3$ | 2.20 (s), 2.45 (s), 2.8 (mc), 3.1 (mc), 4.0-4.35 (m), 6.45 (s), 6.8 (s), 7.15 (mc), 7.25-7.5 (m), 7.95 (d) |
| 19 | S | 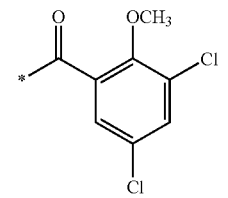 | Cl | Cl | H | CH$_3$ | CH$_3$ | 2.25 (s), 2.4-2.7 (mc), 3.0-3.15 (m), 3.7 (s), 3.95-4.45 (m), 4.65 (mc), 6.4-7.4 (m) |
| 20 | S | 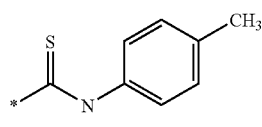 | Cl | Cl | H | CH$_3$ | CH$_3$ | 2.1 (s), 2.4 (s), 2.7-3.15 (m), 4.5 (mc), 4.8-4.95 (m), 6.65 (s), 6.8 (s), 7.15-7.4 (m), 14.3 (s) |
| 21 | S | 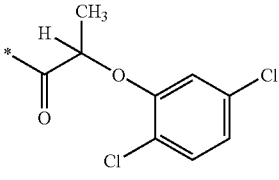 | CH$_3$ | CH$_3$ | H | CH$_3$ | H | 1.5-1.75 (m), 2.15-2.35 (m), 3.0 (mc), 3.9 (mc), 4.1 (mc), 4.7 (mc), 6.15-6.4 (m), 6.75-7.4 (m) |

Action Against Pests:

I. Cotton aphid (*Aphis gossypi*)

The active compounds were formulated in 50:50 acetone: water and 100 ppm Kinetic® surfactant.

Cotton plants in the cotyledon stage (variety 'Delta Pine') are infested with approximately 100 laboratory-reared aphids by placing infested leaf sections on top of the test plants. The leaf sections are removed after 24 hours. The cotyledons of the intact plants are dipped into gradient solutions of the test compound. Aphid mortality on the treated plants, relative to mortality on check plants, is determined after 5 days.

In this test, the compounds of examples 1 to 4, 6, 8 to 11 and 13 to 21 at 300 ppm showed over 70% mortality in comparison with untreated controls.

II. Green Peach Aphid (*Myzus persicae*)

The active compounds were formulated in 50:50 acetone: water and 100 ppm Kinetic® surfactant.

Pepper plants in the 2$^{nd}$ leaf-pair stage (variety 'California Wonder') are infested with approximately 40 laboratory-reared aphids by placing infested leaf sections on top of the test plants. The leaf sections are removed after 24 hours. The leaves of the intact plants are dipped into gradient solutions of the test compound. Aphid mortality on the treated plants, relative to mortality on check plants, is determined after 5 days.

In this test, the compounds of examples 1 to 4, 6 to 11 and 13 to 21 at 300 ppm showed over 70% mortality in comparison with untreated controls.

III. Silverleaf Whitefly

The active compounds were formulated in 50:50 acetone: water and 100 ppm Kinetic® surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were colleted using an aspirator and an 0.6 cm, non-toxic Tygon® tubing (R-3603) connected to a barrier pipette tip. The tip, containing the collected insects, was then gently inserted into the soil containing the treated plant, allowing insects to crawl out of the tip to reach the foliage for feeding. The cups were covered with a re-usable screened lid (150 micron mesh polyester screen PeCap from Tetko Inc). Test plants were maintained in the holding room at about 25° C. and 20-40% relative humid-ity for 3 days avoiding direct exposure to the fluorescent light (24 hour photoperiod) to prevent trapping of heat inside the cup. Mortality was assessed 3 days after treatment of the plants.

In this test, the compounds of examples 1 to 4, 8 to 11, 13 to 17 and 19 to 21 at 300 ppm showed over 70% mortality in comparison with untreated controls.

IV. COMPARATIVE EXAMPLES

Comparative Example 1

Action Against Silverleaf Whitefly

The action against silverleaf whitefly of the inventive compounds from preparation examples 1 and 4 has been compared with the action of compound C.3, wherein $R^1$ is hydrogen (not in accordance with the present invention)

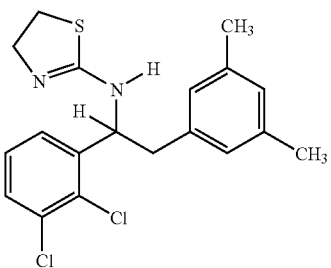

(C.3)

by evaluation of the test shown in paragraph III.). The results are compiled in table 3.

TABLE 3

| concentration [ppm] | mortality in comparison with untreated controls [%] | | |
|---|---|---|---|
| | compound C.3 | compound 1 | compound 4 |
| 300 | 100 | 100 | 100 |
| 100 | 100 | 100 | 100 |
| 10 | 0 | 100 | 50 |

The invention claimed is:
1. A compound of formula (I')

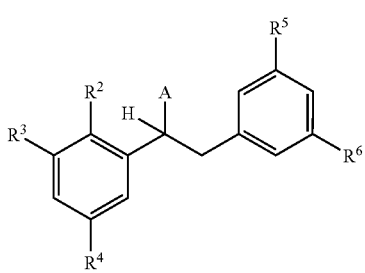

(I')

wherein
A is a radical of formulae A.1 or A.2

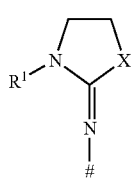

(A.1)

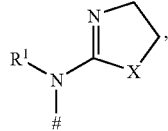

(A.2)

wherein # denotes the bond to the remaining compound of formula (I')

X is selected from the group consisting of O, S and $NR^X$, wherein
  $R^X$ is selected from the group consisting of hydrogen, cyano, nitro, $C_1$-$C_3$-alkyl, $C_1$-$C_3$-alkoxy, $C_1$-$C_3$-haloalkyl, $C_1$-$C_3$-haloalkoxy, formyl, $C_1$-$C_6$-alkylcarbonyl and $C_1$-$C_6$-alkoxycarbonyl;

R1 is selected from the group consisting of
  —C(=S)—$NR^{B1}R^{B2}$, $C_2$-$C_8$-alkenyl, $C_2$-$C_8$-alkynyl and $C_3$-$C_8$-cycloalkyl, wherein the three last mentioned groups are unsubstituted or may carry 1 to 4 substituents $R^{1e}$, B is linear or branched $C_1$-$C_4$-alkanediyl, which is unsubstituted or may carry 1, 2, 3 or 4 radicals selected from the group consisting of halogen and $C_1$-$C_3$-alkoxy;

$R^A$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^{B1}$, $R^{B2}$ are selected independently from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^{B2'}$ is selected from the group consisting of $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^C$ is selected from the group consisting of $C_1$-$C_6$-alkyl which carries 1, 2, 3 or 4 radicals selected from the group consisting of C(=O)OH, aryloxy, hetaryloxy, arylthio, hetarylthio and $C_1$-$C_4$-alkoxycarbonyl, wherein the five last mentioned radicals are unsubstituted or may carry 1, 2, 3 or 4 groups selected independently from the group consisting of CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_8$-cycloalkyl;

$R^{C_1}$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^D$, $R^E$ are selected from the group consisting of $C_2$-$C_6$-alkenyl, $C_2$-$C_6$-alkynyl, wherein the last two mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^{D_1}$, $R^{E_1}$, $R^F$, $R^G$, $R^{H1}$, $R^{H2}$ have one of the meanings given for $R^D$, $R^E$ or are selected from the group consisting of hydrogen and $C_1$-$C_6$-alkyl, which is unsubstituted or carries 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl;

$R^I$, $R^K$ are selected from the group consisting of $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^J$ is selected from the group consisting of hydrogen, $C_1$-$C_6$-alkyl, $C_2$-$C_6$-alkenyl, $C_2$-$C_6$-alkynyl, wherein the last three mentioned radicals may carry 1, 2, 3 or 4 substituents selected independently from the group consisting of halogen, $C_1$-$C_3$-alkoxy, $C_1$-$C_3$-haloalkoxy, $C_1$-$C_3$-alkylthio, $C_1$-$C_3$-haloalkylthio and $C_3$-$C_8$-cycloalkyl, $C_3$-$C_8$-cycloalkyl which is unsubstituted or may carry 1, 2, 3 or 4 substituents $R^{1e}$, phenyl which is unsubstituted or may carry 1, 2, 3 or 4 substituents $R^{1f}$, naphthyl which is unsubstituted or may carry 1, 2, 3 or 4 substituents $R^{1f}$, and hetaryl which is unsubstituted or may carry 1, 2, 3 or 4 substituents $R^{1h}$;

$R^{1a}$, $R^{1b}$, $R^{1c}$ and $R^{1d}$ is selected from the group consisting of hydrogen $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy;

$R^{1e}$, $R^{1g}$ are independently of one another selected from the group consisting of $C_1$-$C_3$-alkyl, $C_1$-$C_3$-alkoxy, $C_1$-$C_3$-haloalkyl and $C_1$-$C_3$-haloalkoxy;

$R^{1f}$, $R^{1h}$ are independently of one another selected from the group consisting of CN, $NO_2$, halogen, $C_1$-$C_3$-alkyl, $C_1$-$C_3$-alkoxy, $C_1$-$C_3$-haloalkyl, $C_1$-$C_3$-haloalkoxy and $C_3$-$C_8$-cycloalkyl;

$R^{1i}$ is selected from the group consisting of hydrogen, $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy; and $R^{1j}$ is selected from the group consisting of $C_1$-$C_3$-alkyl, $C_1$-$C_3$-alkoxy, $C_3$-$C_8$-cycloalkyl, $C_2$-$C_3$-alkenyl and $C_2$-$C_3$-alkenyloxy; and $R^2$, $R^3$, $R^4$, $R^5$ and $R^6$ are each independently hydrogen, halogen, OH, SH, $NH_2$, $SO_3H$, COOH, cyano, nitro, $C_1$-$C_6$-alkyl, $C_1$-$C_6$-alkoxy, $C_1$-$C_6$-alkylamino, di($C_1$-$C_6$-alkyl)amino, $C_1$-$C_8$-alkylthio, $C_2$-$C_6$-alkenyl, $C_2$-$C_6$-alkenyloxy, $C_2$-$C_6$-alkenylamino, $C_2$-$C_6$-alkenylthio, $C_2$-$C_6$-alkynyl, $C_2$-$C_6$-alkynyloxy, $C_2$-$C_6$-alkynylamino, $C_2$-$C_6$-alkynylthio, $C_1$-$C_6$-alkylsulfonyl, $C_1$-$C_6$-alkylsulfoxyl, $C_2$-$C_6$-alkenylsulfonyl, $C_2$-$C_6$-alkynylsulfonyl, formyl, $C_1$-$C_6$-alkylcarbonyl, $C_2$-$C_6$-alkenylcarbonyl, $C_2$-$C_6$-alkynylcarbonyl, $C_1$-$C_6$-alkoxycarbonyl, $C_2$-$C_6$-alkenyloxycarbonyl, $C_2$-$C_6$-alkynyloxycarbonyl, $C_1$-$C_6$-alkylcarbonyloxy, $C_1$-$C_6$-alkylcarbonyloxy, $C_2$-$C_6$-alkenylcarbonyloxy, $C_2$-$C_6$-alkynylcarbonyloxy, wherein the carbon atoms in the aliphatic radicals of the aforementioned groups may carry any combination of 1, 2 or 3 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, $C(O)NR^LR^M$, $(SO_2)NR^LR^M$, wherein $R^L$ and $R^M$ are each independently hydrogen, $C_1$-$C_6$-alkyl, $C_2$-$C_6$-alkenyl, or $C_2$-$C_6$-alkynyl, wherein the carbon atoms in these groups may carry any combination of 1, 2 or 3 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio, a radical Y—Ar or a radical Y-Cy, wherein Y is a single bond, oxygen, sulfur, $C_1$-$C_6$-alkanediyl or $C_1$-$C_6$-alkanediyloxy, Ar is phenyl, naphthyl or a mono- or bicyclic 5- to 10-membered heteroaromatic ring, which contains 1, 2, 3 or 4 heteroatoms selected from the group consisting of oxygen, sulfur and nitrogen as ring members, wherein Ar is unsubstituted or may carry any combination of 1, 2, 3, 4 or 5 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio; and Cy is $C_3$-$C_{12}$-cycloalkyl, which is unsubstituted or substituted with any combination of 1, 2, 3, 4 or 5 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthiol;

and wherein two radicals $R^2$, $R^3$, $R^4$, $R^5$ or $R^6$ that are bound to adjacent carbon atoms of the phenyl rings may form together with said carbon atoms a fused benzene ring, a fused saturated or partially un-saturated 5-, 6-, or 7-membered carbocycle or a fused 5-, 6-, or 7-membered heterocycle, which contains 1, 2, 3 or 4 heteroatoms selected from the group consisting of O, S and N as ring members, and wherein the fused ring is unsubstituted or may carry any combination of 1, 2, 3, or 4 radicals selected from the group consisting of halogen, cyano, nitro, hydroxy, mercapto, amino, carboxyl, $C_1$-$C_6$-alkyl, $C_1$-$C_6$-alkoxy, $C_2$-$C_6$-alkenyloxy, $C_2$-$C_6$-alkynyloxy, $C_1$-$C_6$-haloalkoxy and $C_1$-$C_6$-alkylthio;

provided that $R^2$ and $R^3$ are different from hydrogen or $R^2$ and $R^4$ are different from hydrogen, the enantiomers, diastereomers or salts thereof.

2. The compound of formula (I') according to claim 1, wherein X is S.

3. The compound of formula (I') according to claim 1, wherein $R^1$ is —C(=S)—$NR^{B1}R^{B2}$.

4. The compound of formula (I') according to claim 1, wherein $R^1$ is selected from the group consisting of $C_2$-$C_8$-alkenyl, $C_2$-$C_8$-alkynyl and $C_3$-$C_8$-cycloalkyl, which is unsubstituted or may carry 1 to 4 substituents $R^{1e}$ as defined in claim 1.

5. The compound of formula (I') according to claim 1, wherein A is a radical of formula A.1.

6. The compound according to claim 1, wherein $R^2$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy.

7. The compound according to claim 1 wherein $R^2$ together with $R^3$ forms a bivalent radical selected from —O—$CH_2$—O—, —O—$CH_2$—$CH_2$— or —O—$CF_2$—O—.

8. The compound according to claim 1, wherein $R^3$ is selected from the group consisting of hydrogen, halogen, $C_1$-$C_3$-alkyl and $C_1$-$C_3$-haloalkyl.

9. The compound according to claim 1, wherein $R^4$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy.

10. The compound according to claim 1, wherein $R^5$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy.

11. The compound according to claim 1, wherein $R^6$ is selected from the group consisting of halogen, $C_1$-$C_3$-alkyl, $C_1$-$C_3$-alkoxy, $C_1$-$C_3$-haloalkyl and $C_1$-$C_3$-haloalkoxy.

12. The compound according to claim 1, wherein $R^7$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy.

13. The compound according to claim 1, wherein $R^2$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy;

$R^3$ is selected from the group consisting of hydrogen, halogen, $C_1$-$C_3$-alkyl and $C_1$-$C_3$-haloalkyl; or $R^2$ together with $R^3$ forms a bivalent radical selected from —O—$CH_2$—$CH_2$—, —O—$CH_2$—O— or —O—$CF_2$—O—;

$R^4$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy;

$R^5$ is selected from the group consisting of hydrogen, halogen, $C_1$-$C_3$-alkyl, $C_1$-$C_3$-alkoxy, $C_1$-$C_3$-haloalkyl and $C_1$-$C_3$-haloalkoxy; and $R^6$ is selected from the group consisting of halogen, $C_1$-$C_3$-alkyl, $C_1$-$C_3$-alkoxy, $C_1$-$C_3$-haloalkyl and $C_1$-$C_3$-haloalkoxy;

or the enantiomers, diastereomers or salts thereof.

14. The compound according to claim 13, wherein A is a radical of formula A.1.

15. The compound according to claim 14, wherein X is S.

16. The compound according to claim 15, wherein $R^1$ is selected from the group consisting of $C_2$-$C_8$-alkenyl, $C_2$-$C_8$-alkynyl and $C_3$-$C_8$-cycloalkyl, which is unsubstituted or may carry 1 to 4 substituents $R^{1e}$.

17. The compound according to claim 15, wherein $R^2$ is selected from the group consisting of hydrogen, fluoro, chloro, bromo, methyl, methoxy, difluoromethyl, trifluoromethyl, difluoromethoxy and trifluoromethoxy.

18. The compound according to claim 1, wherein $R^5$ is selected from the group consisting of hydrogen, fluoro, chloro, bromo, methyl, methoxy, difluoromethyl, trifluoromethyl, difluoromethoxy and trifluoromethoxy.

19. The compound according to claim 1, wherein $R^6$ is selected from the group consisting of fluoro, chloro, bromo, methyl, methoxy, difluoromethyl, trifluoromethyl, difluoromethoxy and trifluoromethoxy.

20. An agricultural composition containing at least one compound of claim 1 or an agriculturally acceptable salt thereof and at least one liquid or solid carrier.

21. A method for controlling animal pests which method comprises treating the pests, their food supply, their habitat or their breeding ground or a plant, plant propagation material, soil, area, material or environment in which the pests are growing or may grow, or the materials, plants, plant propagation material, soils, surfaces or spaces to be protected from pest attack or infestation with a pesticidally effective amount of a compound or a salt thereof as defined in claim 1.

22. A method for protecting plant propagation material and/or the plants which grow therefrom, which method comprises treating the plant propagation material with a pesticidally effective amount of a compound or an agriculturally acceptable salt thereof as defined in claim 1.

23. A plant propagation material, comprising at least one compound as defined in claim 1 or an agriculturally acceptable salt thereof.

24. A method for treating or protecting an animal from infestation or infection by parasites which comprises bringing the animal in contact with a parasiticidally effective amount of a compound or a veterinarily acceptable salt thereof as defined in claim 1.

* * * * *

UNITED STATES PATENT AND TRADEMARK OFFICE
CERTIFICATE OF CORRECTION

| | | |
|---|---|---|
| PATENT NO. | : 8,211,924 B2 | Page 1 of 1 |
| APPLICATION NO. | : 12/667299 | |
| DATED | : July 3, 2012 | |
| INVENTOR(S) | : Markus Kordes et al. | |

It is certified that error appears in the above-identified patent and that said Letters Patent is hereby corrected as shown below:

On the cover page, item (86), § 371 (c)(1), (2), (4) Date is: December 30, 2009

Signed and Sealed this
Sixth Day of November, 2012

David J. Kappos
*Director of the United States Patent and Trademark Office*